(12) United States Patent
Haines

(10) Patent No.: US 9,421,022 B2
(45) Date of Patent: *Aug. 23, 2016

(54) METHOD AND APPARATUS FOR TOTAL KNEE ARTHROPLASTY

(71) Applicant: Puget BioBentures LLC, Seattle, WA (US)

(72) Inventor: Timothy G. Haines, Seattle, WA (US)

(73) Assignee: Puget BioVentures LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,534

(22) Filed: Nov. 23, 2015

(65) Prior Publication Data

US 2016/0089168 A1    Mar. 31, 2016

Related U.S. Application Data

(63) Continuation of application No. 14/753,857, filed on Jun. 29, 2015, now Pat. No. 9,192,391, which is a continuation of application No. 13/169,728, filed on Jun. 27, 2011, now Pat. No. 9,066,804, which is a continuation of application No. 10/977,365, filed on Oct. 29, 2004, now Pat. No. 7,967,822, which is a continuation of application No. 10/756,817, filed on Jan. 13, 2004, now Pat. No. 7,344,541, which is a continuation of application No. 09/799,325, filed on Mar. 5, 2001, now Pat. No. 6,695,848.

(51) Int. Cl.
| | |
|---|---|
| *A61B 17/58* | (2006.01) |
| *A61B 17/17* | (2006.01) |
| *A61B 17/15* | (2006.01) |
| *A61B 17/16* | (2006.01) |
| *A61B 17/02* | (2006.01) |
| *A61F 2/38* | (2006.01) |
| *A61F 2/46* | (2006.01) |

(52) U.S. Cl.
CPC .......... *A61B 17/1764* (2013.01); *A61B 17/155* (2013.01); *A61B 17/157* (2013.01); *A61B 17/1675* (2013.01); *A61B 2017/0268* (2013.01); *A61B 2017/1602* (2013.01); *A61F 2/38* (2013.01); *A61F 2/4684* (2013.01)

(58) Field of Classification Search
CPC .. A61B 17/154; A61B 17/155; A61B 17/157; A61B 17/15; A61B 17/1675; A61B 17/1764; A61B 17/148

See application file for complete search history.

(56) References Cited

U.S. PATENT DOCUMENTS

| | | |
|---|---|---|
| 2,697,433 A | 12/1954 | Zehnder |
| 3,457,922 A | 7/1969 | Ray |

(Continued)

FOREIGN PATENT DOCUMENTS

| | | |
|---|---|---|
| EP | 0104732 A1 | 4/1984 |
| EP | 0121142 A1 | 10/1984 |

(Continued)

OTHER PUBLICATIONS

USPTO Correspondence entitled Order Granting/Denying Request for Inter Partes Reexamination, U.S. Appl. No. 95/001,469, Patent No. Under Reexammation: 7,344,541 dated Nov. 10, 2010, 15 pages.

(Continued)

*Primary Examiner* — Mary Hoffman
(74) *Attorney, Agent, or Firm* — Patterson Thuente Pedersen, P.A.

(57) ABSTRACT

The apparatus of the present invention includes a number of components including tibial and femoral alignment guides, tibial and femoral cutting guides and tibial and femoral implants for total knee arthroplasty procedures.

25 Claims, 75 Drawing Sheets

(56) References Cited

U.S. PATENT DOCUMENTS

| | | |
|---|---|---|
| 3,739,662 A | 6/1973 | Windelman et al. |
| 3,748,662 A | 7/1973 | Helfet |
| 3,774,244 A | 11/1973 | Walker |
| 3,798,679 A | 3/1974 | Ewald |
| 3,816,855 A | 6/1974 | Saleh |
| 3,906,550 A | 9/1975 | Rostoker et al. |
| 3,943,934 A | 3/1976 | Bent |
| 3,953,899 A | 5/1976 | Charnley |
| 3,958,278 A | 5/1976 | Lee et al. |
| 3,977,289 A | 8/1976 | Tuke |
| 4,016,606 A | 4/1977 | Murray et al. |
| 4,069,824 A | 1/1978 | Weinstock |
| 4,178,641 A | 12/1979 | Grundei et al. |
| 4,207,627 A | 6/1980 | Cloutier |
| 4,213,209 A | 7/1980 | Insall et al. |
| 4,249,270 A | 2/1981 | Bahler et al. |
| 4,340,978 A | 7/1982 | Buechel et al. |
| 4,349,058 A | 9/1982 | Comparetto |
| 4,353,135 A | 10/1982 | Forte et al. |
| 4,358,859 A | 11/1982 | Schurman et al. |
| 4,421,112 A | 12/1983 | Mains et al. |
| 4,457,307 A | 7/1984 | Stillwell |
| 4,474,177 A | 10/1984 | Whiteside |
| 4,479,271 A | 10/1984 | Bolesky et al. |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,885 A | 2/1986 | Androphy |
| 4,567,886 A | 2/1986 | Petersen |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna et al. |
| 4,659,331 A | 4/1987 | Matthews et al. |
| 4,662,889 A | 5/1987 | Zichner et al. |
| 4,693,721 A | 9/1987 | Ducheyne |
| 4,703,751 A | 11/1987 | Pohl |
| 4,709,699 A | 12/1987 | Michael et al. |
| 4,711,639 A | 12/1987 | Grundei |
| 4,714,472 A | 12/1987 | Averill et al. |
| 4,714,473 A | 12/1987 | Bloebaum |
| 4,718,413 A | 1/1988 | Johnson |
| 4,721,104 A | 1/1988 | Kaufman et al. |
| 4,722,330 A | 2/1988 | Russell et al. |
| 4,731,086 A | 3/1988 | Whiteside et al. |
| 4,736,086 A | 4/1988 | Obara |
| 4,736,737 A | 4/1988 | Fargie et al. |
| 4,738,256 A | 4/1988 | Freeman et al. |
| 4,759,350 A | 7/1988 | Dunn et al. |
| 4,770,663 A | 9/1988 | Hanslik et al. |
| 4,787,383 A | 11/1988 | Kenna |
| 4,822,365 A | 4/1989 | Walker et al. |
| 4,834,758 A | 5/1989 | Lane et al. |
| 4,841,975 A | 6/1989 | Woolson |
| 4,880,429 A | 11/1989 | Stone |
| 4,892,093 A | 1/1990 | Zarnowski et al. |
| 4,893,619 A | 1/1990 | Dale et al. |
| 4,896,663 A | 1/1990 | Vandewalls |
| 4,919,667 A | 4/1990 | Richmond |
| 4,926,847 A | 5/1990 | Luckman |
| 4,935,023 A | 6/1990 | Whiteside et al. |
| 4,936,853 A | 6/1990 | Fabian et al. |
| 4,938,762 A | 7/1990 | Wehrli |
| 4,938,769 A | 7/1990 | Shaw |
| 4,944,757 A | 7/1990 | Martinez et al. |
| 4,950,298 A | 8/1990 | Gustilo et al. |
| 4,952,213 A | 8/1990 | Bowman et al. |
| 4,963,152 A | 10/1990 | Hofmann et al. |
| 4,963,153 A | 10/1990 | Noesberger et al. |
| 4,971,075 A | 11/1990 | Lee |
| 4,979,949 A | 12/1990 | Matsen, III et al. |
| 5,002,545 A | 3/1991 | Whiteside et al. |
| 5,002,547 A | 3/1991 | Poggie et al. |
| 5,007,933 A | 4/1991 | Sidebotham et al. |
| 5,007,934 A | 4/1991 | Stone |
| 5,021,056 A | 6/1991 | Hofmann et al. |
| 5,021,061 A | 6/1991 | Wevers et al. |
| 5,032,134 A | 7/1991 | Lindwer |
| 5,041,138 A | 8/1991 | Vacanti et al. |
| 5,047,032 A | 9/1991 | Jellicoe |
| 5,049,149 A | 9/1991 | Schmidt |
| 5,053,037 A | 10/1991 | Lackey |
| 5,059,037 A | 10/1991 | Albert |
| 5,062,852 A | 11/1991 | Dorr et al. |
| 5,080,675 A | 1/1992 | Lawes et al. |
| 5,092,869 A | 3/1992 | Waldron |
| 5,098,436 A | 3/1992 | Ferrante et al. |
| 5,100,409 A | 3/1992 | Coates et al. |
| 5,112,336 A | 5/1992 | Krevolin et al. |
| 5,116,375 A | 5/1992 | Hofmann |
| 5,122,144 A | 6/1992 | Bert et al. |
| 5,129,909 A | 7/1992 | Sutherland |
| 5,133,758 A | 7/1992 | Hollister |
| 5,133,759 A | 7/1992 | Turner |
| 5,137,536 A | 8/1992 | Koshino |
| 5,147,364 A | 9/1992 | Comparetto |
| 5,147,365 A | 9/1992 | Whitlock et al. |
| 5,147,405 A | 9/1992 | Van Zile et al. |
| 5,176,710 A | 1/1993 | Hahn et al. |
| 5,178,626 A | 1/1993 | Pappas |
| 5,190,547 A | 3/1993 | Barber, Jr. et al. |
| 5,197,944 A | 3/1993 | Steele |
| 5,201,881 A | 4/1993 | Evans |
| 5,203,807 A | 4/1993 | Evans et al. |
| 5,206,023 A | 4/1993 | Hunziker |
| 5,219,362 A | 6/1993 | Tuke et al. |
| 5,226,916 A | 7/1993 | Goodfellow et al. |
| 5,228,459 A | 7/1993 | Caspari et al. |
| 5,234,432 A | 8/1993 | Brown |
| 5,234,433 A | 8/1993 | Bert et al. |
| 5,236,432 A | 8/1993 | Matsen, III et al. |
| 5,236,461 A | 8/1993 | Forte |
| 5,236,875 A | 8/1993 | Trigg et al. |
| 5,250,050 A | 10/1993 | Poggie et al. |
| 5,263,498 A | 11/1993 | Caspari et al. |
| 5,263,956 A | 11/1993 | Nobles |
| 5,269,786 A | 12/1993 | Morgan |
| 5,275,603 A | 1/1994 | Ferrante et al. |
| 5,279,575 A | 1/1994 | Sugarbaker |
| 5,282,803 A | 2/1994 | Lackey |
| 5,282,867 A | 2/1994 | Mikhail |
| 5,284,482 A | 2/1994 | Mikhail |
| 5,304,181 A | 4/1994 | Caspari et al. |
| 5,306,276 A | 4/1994 | Johnson et al. |
| 5,314,482 A | 5/1994 | Goodfellow et al. |
| 5,326,358 A | 7/1994 | Aubriot et al. |
| 5,330,533 A | 7/1994 | Walker |
| 5,330,534 A | 7/1994 | Herrington et al. |
| 5,342,368 A | 8/1994 | Petersen |
| 5,358,527 A | 10/1994 | Forte |
| 5,358,529 A | 10/1994 | Davidson |
| 5,358,531 A | 10/1994 | Goodfellow et al. |
| 5,364,401 A | 11/1994 | Ferrante et al. |
| 5,364,402 A | 11/1994 | Mumme et al. |
| 5,370,699 A | 12/1994 | Hood et al. |
| 5,370,701 A | 12/1994 | Finn |
| 5,391,170 A | 2/1995 | McGuire et al. |
| 5,397,330 A | 3/1995 | Mikhail |
| 5,405,349 A | 4/1995 | Burkinshaw et al. |
| 5,413,604 A | 5/1995 | Hodge |
| 5,415,663 A | 5/1995 | Luckman et al. |
| 5,417,694 A | 5/1995 | Marik et al. |
| 5,417,695 A | 5/1995 | Axelson, Jr. |
| 5,443,464 A | 8/1995 | Russell et al. |
| 5,454,816 A | 10/1995 | Ashby |
| 5,462,551 A | 10/1995 | Bailey et al. |
| 5,470,335 A | 11/1995 | Du Toit |
| 5,474,559 A | 12/1995 | Bertin et al. |
| 5,480,446 A | 1/1996 | Goodfellow et al. |
| 5,514,136 A | 5/1996 | Richelsoph |
| 5,514,139 A | 5/1996 | Goldstein et al. |

(56) References Cited

U.S. PATENT DOCUMENTS

| | | |
|---|---|---|
| 5,514,143 A | 5/1996 | Bonutti et al. |
| 5,520,694 A | 5/1996 | Dance et al. |
| 5,520,695 A | 5/1996 | Luckman |
| 5,540,695 A | 7/1996 | Levy |
| 5,542,947 A | 8/1996 | Treacy |
| 5,549,683 A | 8/1996 | Bonutti |
| 5,549,684 A | 8/1996 | Amino et al. |
| 5,549,688 A | 8/1996 | Ries et al. |
| 5,551,429 A | 9/1996 | Fitzpatrick et al. |
| 5,562,674 A | 10/1996 | Stalcup et al. |
| 5,569,262 A | 10/1996 | Carney |
| 5,571,100 A | 11/1996 | Goble et al. |
| 5,578,039 A | 11/1996 | Vendrely et al. |
| 5,593,411 A | 1/1997 | Stalcup et al. |
| 5,597,379 A | 1/1997 | Haines et al. |
| 5,597,397 A | 1/1997 | Funk et al. |
| 5,601,563 A | 2/1997 | Burke et al. |
| 5,601,566 A | 2/1997 | Dance et al. |
| 5,609,645 A | 3/1997 | Vinciguerra |
| 5,611,802 A | 3/1997 | Samuelson et al. |
| 5,613,969 A | 3/1997 | Jenkins, Jr. |
| 5,628,749 A | 5/1997 | Vendrely et al. |
| 5,639,279 A | 6/1997 | Burkinshaw et al. |
| 5,643,272 A | 7/1997 | Haines et al. |
| 5,649,928 A | 7/1997 | Grundei |
| 5,653,714 A | 8/1997 | Dietz et al. |
| 5,658,293 A | 8/1997 | Vanlaningham |
| 5,667,511 A | 9/1997 | Vendrely et al. |
| 5,681,354 A | 10/1997 | Eckhoff |
| 5,682,886 A | 11/1997 | Delp et al. |
| 5,690,632 A | 11/1997 | Schwartz et al. |
| 5,690,635 A | 11/1997 | Matsen, III et al. |
| 5,690,637 A | 11/1997 | Wen et al. |
| 5,697,935 A | 12/1997 | Moran et al. |
| 5,702,458 A | 12/1997 | Burstein et al. |
| 5,723,016 A | 3/1998 | Minns et al. |
| 5,725,530 A | 3/1998 | Popken |
| 5,728,162 A | 3/1998 | Eckhoff |
| 5,755,801 A | 5/1998 | Walker et al. |
| 5,755,803 A | 5/1998 | Haines et al. |
| 5,755,804 A | 5/1998 | Schmotzer et al. |
| 5,766,257 A | 6/1998 | Goodman et al. |
| 5,768,134 A | 6/1998 | Swaelens et al. |
| 5,769,855 A | 6/1998 | Bertin et al. |
| 5,769,899 A | 6/1998 | Schwartz et al. |
| 5,776,200 A | 7/1998 | Johnson et al. |
| 5,782,921 A | 7/1998 | Colleran et al. |
| 5,782,925 A | 7/1998 | Collazo et al. |
| 5,799,055 A | 8/1998 | Peshkin et al. |
| 5,800,552 A | 9/1998 | Forte |
| 5,810,827 A | 9/1998 | Haines et al. |
| 5,824,100 A | 10/1998 | Kester et al. |
| 5,824,102 A | 10/1998 | Buscayret |
| 5,824,105 A | 10/1998 | Ries et al. |
| 5,871,545 A | 2/1999 | Goodfellow et al. |
| 5,871,546 A | 2/1999 | Colleran et al. |
| 5,879,354 A | 3/1999 | Haines et al. |
| 5,879,392 A | 3/1999 | McMinn |
| 5,906,643 A | 5/1999 | Walker |
| 5,908,424 A | 6/1999 | Bertin et al. |
| 5,925,049 A | 7/1999 | Gustilo et al. |
| 5,935,173 A | 8/1999 | Roger et al. |
| 5,954,770 A | 9/1999 | Schmotzer et al. |
| 5,980,526 A | 11/1999 | Johnson et al. |
| 5,986,169 A | 11/1999 | Gjunter |
| 5,997,577 A | 12/1999 | Herrington et al. |
| 6,039,764 A | 3/2000 | Pottenger et al. |
| 6,056,754 A | 5/2000 | Haines et al. |
| 6,059,788 A | 5/2000 | Katz |
| 6,068,658 A | 5/2000 | Insall et al. |
| 6,080,195 A | 6/2000 | Colleran et al. |
| 6,099,570 A | 8/2000 | Livet et al. |
| 6,110,182 A | 8/2000 | Mowlai-Ashtiani |
| 6,120,543 A | 9/2000 | Kubein-Meesenburg et al. |
| 6,132,468 A | 10/2000 | Mansmann |
| 6,139,581 A | 10/2000 | Engh et al. |
| 6,165,223 A | 12/2000 | Metzger et al. |
| 6,171,340 B1 | 1/2001 | McDowell |
| 6,195,577 B1 | 2/2001 | Truwit et al. |
| 6,197,064 B1 | 3/2001 | Haines et al. |
| 6,203,576 B1 | 3/2001 | Afriat et al. |
| 6,206,926 B1 | 3/2001 | Pappas |
| 6,210,443 B1 | 4/2001 | Marceaux et al. |
| 6,235,060 B1 | 5/2001 | Kubein-Meesenburg et al. |
| 6,236,875 B1 | 5/2001 | Bucholz et al. |
| 6,264,697 B1 | 7/2001 | Walker |
| 6,285,902 B1 | 9/2001 | Kienzle, III et al. |
| 6,306,146 B1 | 10/2001 | Dinkler |
| 6,306,172 B1 | 10/2001 | O'Neil et al. |
| 6,325,828 B1 | 12/2001 | Dennis et al. |
| 6,340,363 B1 | 1/2002 | Bolger et al. |
| 6,342,075 B1 | 1/2002 | MacArthur |
| 6,348,058 B1 | 2/2002 | Melkent et al. |
| 6,361,564 B1 | 3/2002 | Marceaux et al. |
| 6,368,353 B1 | 4/2002 | Arcand |
| 6,375,658 B1 | 4/2002 | Hangody et al. |
| 6,379,388 B1 | 4/2002 | Ensign et al. |
| 6,401,346 B1 | 6/2002 | Roberts |
| 6,406,497 B2 | 6/2002 | Takei |
| 6,413,279 B1 | 7/2002 | Metzger et al. |
| 6,430,434 B1 | 8/2002 | Mittelstadt |
| 6,436,145 B1 | 8/2002 | Miller |
| 6,443,991 B1 | 9/2002 | Running |
| 6,458,128 B1 | 10/2002 | Schulze |
| 6,470,207 B1 | 10/2002 | Simon et al. |
| 6,475,241 B2 | 11/2002 | Pappas |
| 6,477,400 B1 | 11/2002 | Barrick |
| 6,482,409 B1 | 11/2002 | Lobb et al. |
| 6,485,519 B2 | 11/2002 | Meyers et al. |
| 6,491,699 B1 | 12/2002 | Henderson et al. |
| 6,491,726 B2 | 12/2002 | Pappas |
| 6,500,208 B1 | 12/2002 | Metzger et al. |
| 6,506,215 B1 | 1/2003 | Letot et al. |
| 6,520,964 B2 | 2/2003 | Tallarida et al. |
| 6,554,838 B2 | 4/2003 | McGovern et al. |
| 6,575,980 B1 | 6/2003 | Robie et al. |
| 6,579,290 B1 | 6/2003 | Hardcastle et al. |
| 6,595,997 B2 | 7/2003 | Axelson, Jr. |
| 6,620,198 B2 | 9/2003 | Burstein et al. |
| 6,623,526 B1 | 9/2003 | Lloyd |
| 6,645,251 B2 | 11/2003 | Salehi et al. |
| 6,679,917 B2 | 1/2004 | Ek |
| 6,685,711 B2 | 2/2004 | Axelson, Jr. et al. |
| 6,694,168 B2 | 2/2004 | Traxel et al. |
| 6,695,848 B2 | 2/2004 | Haines |
| 6,697,664 B2 | 2/2004 | Kienzle III et al. |
| 6,697,768 B2 | 2/2004 | Jones et al. |
| 6,701,174 B1 | 3/2004 | Krause et al. |
| 6,702,821 B2 | 3/2004 | Bonutti |
| 6,711,432 B1 | 3/2004 | Weiss et al. |
| 6,725,080 B2 | 4/2004 | Melkent et al. |
| 6,755,563 B2 | 6/2004 | Wahlig et al. |
| 6,755,864 B2 | 6/2004 | Brack et al. |
| 6,764,516 B2 | 7/2004 | Pappas |
| 6,770,097 B2 | 8/2004 | Leclercq |
| 6,773,461 B2 | 8/2004 | Meyers et al. |
| 6,783,550 B2 | 8/2004 | MacArthur |
| 6,796,988 B2 | 9/2004 | Melkent et al. |
| 6,827,723 B2 | 12/2004 | Carson |
| 6,858,032 B2 | 2/2005 | Chow et al. |
| 6,866,684 B2 | 3/2005 | Fell et al. |
| 6,875,222 B2 | 4/2005 | Long et al. |
| 6,898,858 B1 | 5/2005 | Spell |
| 6,911,044 B2 | 6/2005 | Fell et al. |
| 6,916,324 B2 | 7/2005 | Sanford et al. |
| 6,916,340 B2 | 7/2005 | Metzger et al. |
| 6,942,627 B2 | 9/2005 | Huitema |
| 6,942,694 B2 | 9/2005 | Liddicoat et al. |
| 7,018,418 B2 | 3/2006 | Amrich et al. |
| 7,029,477 B2 | 4/2006 | Grimm |
| 7,048,741 B2 | 5/2006 | Swanson |
| 7,077,867 B1 | 7/2006 | Pope et al. |
| 7,104,996 B2 | 9/2006 | Bonutti |
| 7,141,053 B2 | 11/2006 | Rosa et al. |

(56) References Cited

U.S. PATENT DOCUMENTS

| | | |
|---|---|---|
| 7,172,596 B2 | 2/2007 | Coon et al. |
| 7,175,630 B2 | 2/2007 | Farling et al. |
| 7,241,298 B2 | 7/2007 | Nemec et al. |
| 7,326,252 B2 | 2/2008 | Otto et al. |
| 7,344,541 B2 | 3/2008 | Haines et al. |
| 7,371,240 B2 | 5/2008 | Pinczewski et al. |
| 7,422,605 B2 | 9/2008 | Burstein et al. |
| 7,491,235 B2 | 2/2009 | Fell |
| 7,922,771 B2 | 4/2011 | Otto et al. |
| 7,967,822 B2 | 6/2011 | Haines et al. |
| 9,066,804 B2 | 6/2015 | Haines |
| 9,192,391 B2 | 11/2015 | Haines |
| 2001/0018615 A1 | 8/2001 | Biegun et al. |
| 2001/0044627 A1 | 11/2001 | Justin |
| 2001/0049558 A1 | 12/2001 | Liddicoat et al. |
| 2002/0029038 A1 | 3/2002 | Haines |
| 2002/0055784 A1 | 5/2002 | Burstein et al. |
| 2002/0103541 A1 | 8/2002 | Meyers et al. |
| 2002/0107576 A1 | 8/2002 | Meyers et al. |
| 2002/0120340 A1 | 8/2002 | Metzger et al. |
| 2002/0161447 A1 | 10/2002 | Salehi et al. |
| 2003/0028196 A1 | 2/2003 | Bonutti |
| 2003/0055501 A1 | 3/2003 | Fell et al. |
| 2003/0055509 A1 | 3/2003 | McCue et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0069585 A1 | 4/2003 | Axelson, Jr. et al. |
| 2003/0069591 A1 | 4/2003 | Carson et al. |
| 2003/0093156 A1 | 5/2003 | Metzger et al. |
| 2003/0130665 A1 | 7/2003 | Pinczewski et al. |
| 2003/0171757 A1 | 9/2003 | Coon et al. |
| 2003/0181986 A1 | 9/2003 | Buchholz |
| 2003/0208122 A1 | 11/2003 | Melkent et al. |
| 2003/0212413 A1 | 11/2003 | Wilk |
| 2004/0039396 A1 | 2/2004 | Couture et al. |
| 2004/0044414 A1 | 3/2004 | Nowakowski |
| 2004/0122305 A1 | 6/2004 | Grimm et al. |
| 2004/0152970 A1 | 8/2004 | Hunter et al. |
| 2004/0153066 A1 | 8/2004 | Coon et al. |
| 2004/0199249 A1 | 10/2004 | Fell |
| 2004/0199250 A1 | 10/2004 | Fell |
| 2004/0243244 A1 | 12/2004 | Otto et al. |
| 2004/0249467 A1 | 12/2004 | Meyers et al. |
| 2004/0249471 A1 | 12/2004 | Bindseil et al. |
| 2004/0267363 A1 | 12/2004 | Fell et al. |
| 2005/0033424 A1 | 2/2005 | Fell |
| 2005/0055028 A1 | 3/2005 | Haines |
| 2005/0149038 A1 | 7/2005 | Haines et al. |
| 2005/0149039 A1 | 7/2005 | Haines et al. |
| 2005/0149040 A1 | 7/2005 | Haines et al. |
| 2005/0171604 A1 | 8/2005 | Michalow |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero et al. |
| 2006/0058882 A1 | 3/2006 | Haines |
| 2007/0078517 A1 | 4/2007 | Engh et al. |
| 2007/0179607 A1 | 8/2007 | Hodorek et al. |
| 2008/0172054 A1 | 7/2008 | Claypool et al. |
| 2009/0076514 A1 | 3/2009 | Haines |
| 2009/0082773 A1 | 3/2009 | Haines |
| 2009/0138018 A1 | 5/2009 | Haines |
| 2011/0257654 A1 | 10/2011 | Haines et al. |

FOREIGN PATENT DOCUMENTS

| | | |
|---|---|---|
| EP | 0 189 253 A2 | 7/1986 |
| EP | 0243109 B1 | 10/1987 |
| EP | 0327249 A2 | 8/1989 |
| EP | 0337901 A1 | 10/1989 |
| EP | 0380451 A2 | 8/1990 |
| EP | 0415837 A2 | 3/1991 |
| EP | 0 466 659 A2 | 1/1992 |
| EP | 0474320 A1 | 3/1992 |
| EP | 0 538 153 A1 | 4/1993 |
| EP | 0555003 A1 | 8/1993 |
| EP | 0556998 A1 | 8/1993 |
| EP | 0682916 A2 | 11/1995 |
| EP | 0761242 A1 | 3/1997 |
| EP | 0923916 A1 | 6/1999 |
| EP | 0941719 A2 | 9/1999 |
| EP | 0970667 A1 | 1/2000 |
| EP | 0988840 A1 | 3/2000 |
| EP | 0916321 B1 | 6/2003 |
| FR | 2635675 A1 | 3/1990 |
| FR | 2664157 A1 | 1/1992 |
| FR | 2701387 A1 | 8/1994 |
| FR | 2710258 A1 | 3/1995 |
| FR | 2760352 A1 | 9/1998 |
| GB | 1409150 | 10/1975 |
| GB | 2007980 B | 7/1982 |
| GB | 2296443 A | 7/1996 |
| GB | 2324249 A | 10/1998 |
| GB | 2335145 A | 9/1999 |
| JP | 02-501806 A | 1/1983 |
| JP | 58-209343 A | 12/1983 |
| JP | 61-170453 A | 8/1986 |
| JP | 62-133948 A | 6/1987 |
| JP | 62-254750 A | 6/1987 |
| JP | 01-119244 A | 5/1989 |
| JP | 01-126957 A | 5/1989 |
| JP | 01-209055 A | 8/1989 |
| JP | 02-057247 A | 2/1990 |
| JP | 02-234756 A | 9/1990 |
| JP | 02-234757 A | 9/1990 |
| JP | 02-239861 A | 9/1990 |
| JP | 02-243143 A | 9/1990 |
| JP | 02-246971 A | 10/1990 |
| JP | 02274214 A | 11/1990 |
| JP | 03-032663 A | 2/1991 |
| JP | 04-297254 A | 10/1992 |
| JP | 04-361746 A | 12/1992 |
| JP | 05-03880 A | 1/1993 |
| JP | 5-41510 A | 2/1993 |
| JP | 05-502814 A | 5/1993 |
| JP | 05-269140 A | 10/1993 |
| JP | 05-277130 A | 10/1993 |
| JP | 06-08033 A | 1/1994 |
| JP | 06-38971 A | 2/1994 |
| JP | 6-217984 A | 8/1994 |
| JP | 06-233775 A | 8/1994 |
| JP | 06-237941 A | 8/1994 |
| JP | 7-501966 | 3/1995 |
| JP | 7-116185 A | 5/1995 |
| JP | 7-136200 A | 5/1995 |
| RU | 577020 T | 10/1977 |
| RU | 2121319 C1 | 11/1998 |
| SE | 382155 | 1/1976 |
| WO | WO 81/03122 A1 | 11/1981 |
| WO | WO 91/00061 A1 | 1/1991 |
| WO | WO 91/10408 A1 | 7/1991 |
| WO | WO 93/22990 A1 | 11/1993 |
| WO | WO 93/25157 A1 | 12/1993 |
| WO | WO 94/05212 A1 | 3/1994 |
| WO | WO 94/08528 A1 | 4/1994 |
| WO | WO 94/09730 A1 | 5/1994 |
| WO | WO 94/14366 A2 | 7/1994 |
| WO | WO 94/22397 A1 | 10/1994 |
| WO | WO 96/01588 A1 | 1/1996 |
| WO | WO 96/07361 A1 | 3/1996 |
| WO | WO 96/24295 A1 | 8/1996 |
| WO | WO 97/05827 A1 | 2/1997 |
| WO | WO 97/29703 A1 | 8/1997 |

(56) References Cited

FOREIGN PATENT DOCUMENTS

| WO | WO 97/29704 A1 | 8/1997 |
|---|---|---|
| WO | WO 98/20817 A1 | 5/1998 |
| WO | WO 99/27872 A1 | 6/1999 |
| WO | WO 99/30649 A1 | 6/1999 |
| WO | WO 01/13825 A1 | 3/2001 |
| WO | WO 02/34310 A2 | 5/2002 |
| WO | WO 2004/069036 A2 | 8/2004 |
| WO | WO 2004/070580 A2 | 8/2004 |
| WO | WO 2004/100758 A2 | 11/2004 |
| WO | WO 2004/100839 A1 | 11/2004 |

OTHER PUBLICATIONS

Freeman Samuelson, Total Knee System, published by Biomet, Inc., 1994 ("Biomet Brochure") (Attached as Exhibit F).
Freeman, Mark II Total Knee Replacement System, published 1985 (Attached as Exhibit G).
Protek F/S Modular Total Knee Replacement System, pp. 1-57, published by Protek in Jan. 1991 (Attached as Exhibit H).
U.S. Pat. No. 5,611,802, Inventor: Samuelson et al., Issued Mar. 18, 1997 (Attached as Exhibit L).
U.S. Pat. No. 5,630,820. Inventor: Todd, Issued May 20, 1997 (Attached as Exhibit M).
Low Contact Stress Meniscal Bearing Unicompartmental Knee Replacement: Long-Term Evaluation of Cemented and Cementless Results, Journal of Orthopaedic Rheumatology (presented at the 57.sup.th Annual American Academy of Orthpaedic Surgeons Meetings, New Orleans, LA, Feb. 11, 1990), Bates No. DEP00004096-DEP00004107.
N. J. Unicompartmental Knee, Dated Sep. 15, 1989, Bates No. DEP00004108-DEP00004116.
Buechel, Frederick F., NJ LCS Unicompartmental Knee System with Porocoat, dated Oct. 24, 1994, Bates No. DEP000004117-DEP00004130.
Buechel, Frederick F. NJ LCS Unicompartmental Knee System with Porocoat, 1994, Bates No. DEP00004131-DEP00004141.
Buechel, Frederick F. NJ LCS Unicompartmental Knee System with Porocoat, 1994, Bates No. DEP00004142-DEP00004152.
Engh, et al., The AMK Total Knee System, Design Rationale and Surgical Procedure, dated 1989, Bates No. DEP00004153-DEP00004201.
Advertising Proteck Mark II PCR Total Knee Replacement System, Journal of Bone and Joint Surgery. 1987, Bates No. DEP00004202-DEP00004230.
Protek, Parts Brochure for Mark II Proteck, 1987, Bates No. DEP00004231-DEP00004235.
Chapman, Michael W., Operative Orthopaedics, vol. 1, Published by J.B. Lipponcott Co., Philadelphia, dated 1988, Bates No. DEP00004236-DEP00004247.
American Academy of Orthopaedic Surgeons, Flyer from 57.sup.th Annual American Academy of Orthopaedic Surgeons Meeting, Feb. 13, 1990, Bates No. DEP00004248-DEP00004251.
Crossett et al., AMK Congruency Instrument System, Surgical Technique, dated 1997, Bates No. DEP00004252-DEP00004267.
Engh et al., AMK Surgical Technique, Bates No. DEP00004268-DEP00004298, dated 1989.
Engh et al., AMK Surgical Technique, Bates No. DEP00004299-DEP0004329, dated 1989.
Crenshaw, A.H., Campbell's Operative Orthopaedics, 4.sup.Edition, vol. 1, Bates No. DEP00004330-DEP00004333, dated 1963.
Biomet, Oxford Brochure: Consistent Instrumentation, Bates No. DEP00004334-EP00004336, undated.
Howmedica, Duraconcept, Design Concepts of the Duracon Total Knee System, Bates No. DEP00004337-DEP00004337, 1993.
Freeman et al., Total Knee System, Bates No. DEP00004350-DEP00004361, Published prior to Jun. 7, 1994.
Freeman et al., F/S Modular Total Knee Replacement System—SICOT, 90 Edition, Bates No. DEP00004362-DEP00004373, dated 1990.
Buechel, Frederick F., Howmedica Product Catalog, Bates No. DEP00004374-DEP00004375, dated 1994.
Massarella, Antony, Interax Bulletin, No. 6, Tibial Intramedullary Alignment Surgical Technique, Bates No. DEP00004387-DEP0000-4390, dated Feb. 23, 1994.
Desjardins et al., Interax Operative Technique, Bates No. DEP00004391-DEP00004411, dated 1994.
Desjardins et al., Interax Total Knee Operative Technique: Monogram Total Knee Instruments, Bates No. DEP00004412-DEP00004432, dated 1993.
Howmedica, Interax Tibial IM, Bates No. DEP00004433-DEP00004433, dated 1994.
Depuy, LCS Uni PMA Data from FDA Website, Bates No. DEP00004434-DEP00004434, dated 1991.
Depuy, *LCS Uni Lateral Resection Guide*, Bates No. DEP00004435-DEP00004451, dated Mar. 1991.
Briard et al., LCS Uni Unicompartmental Knee System with Porocoat, Bates No. DEP00004452-DEP00004462, dated 1991.
Freeman et al., Mark II Total Knee Replacement System, Bates No. DEP00004463-DEP00004492, dated 1985.
Buechel, Frederick F., NJ LCS Unicompartmental Knee System with Porocoat, Bates No. DEP00004493-DEP00004503, dated 1994.
Chapman, Michael W. Operative Orthopaedics, vol. 3, 2.sup.nd Edition, Published by J.B. Lipponcott Co., Bates No. DEP00004504-DEP00004508, dated 1993.
Biomet, Oxford Meniscal Knee Phase II Unicompartmental Replacement, Bates No. DEP00004509-DEP00004515, Published prior to Jun. 7, 1994.
Scott et al., P.F.C. Sigma Unicompartmental Knee System, Bates No. DEP00004531-DEP00004539, dated 1998.
Freeman et al., F/S Modular Total Knee Replacement System, Bates No. DEP00004540-DEP00004596, dated 1990.
Photos of Miller-Galante Zimmer Instruments, Bates No. DEP00004597-DEP00004598, Sep. 27, 2010.
Photos of Interax Knee Instruments, Bates No. DEP00004666-DEP00004671, Sep. 27, 2010.
Broughton et al., Unicompartmental Replacement and High Tibial Osteotomy Osteoarthritis of the Knee, Journal of Bone and Joint Surgery, vol. 68-B, No. 3, May 1, 1986, pp. 447-452, Bates No. DEP00004752-DEP00004763.
Scott et al., Uncondylar Unicompartmental Replacement for Osteoarthrisit of the Knee, Journal of Bone and Joint Surgery, vol. 63-A, No. 4, Apr. 1, 1981, Bates No. DEP00004764-DEP00004775.
Thornhill, Thomas S., Unicompartmental Knee Arthroplasty Clinical Orthopaedics and Related Research, No. 205, Apr. 1, 1986, pp. 121-131, Bates No. DEP00004776-DEP00004791.
Forst et al., A Special jg for Tibial Resection for the Implantation of GSB-Knee-Prostheses in Problematic cases, pp. 162-166, dated Jun. 1, 1984, Bates No. DEP00004838-DEP00004842.
Ingillis et al., Revision Total Knee Replacement Technique in Orthopedics, dated Apr. 1, 1990, Bates No. DEP00005583-DEP00005592.
Appendix A, 31 pages, Chart regarding U.S. Pat. No. 7,344,541, undated.
Appendix B, 66 pages, undated.
Appendix C, 799 pages, undated.
Request for Inter Partes Reexamination of U.S. Pat. No. 7,344,541, Issued Mar. 18, 2008, 889 pages.
*Hudson Surgical Design, Inc.* vs. *Depuy Orthopaedics, Inc.*, Defendant Depuy Orthopaedics, Inc.'s Local Patent Rule 2.3 Initial Non-Infringement, Invalidity, and Unenforceability Contentions, Civil Action No. 10-CV-02103, Dated Sep. 27, 2010, 13 pages.
Whiteside Ortholoc: Total Knee System, Dow Corning Wright, Jun. 1985, 12 pages.
Insall/Burstein II: Modular Knee System, Zimmer, Inc., .COPYRGT. 1989, 20 pages.
T.D.V. Cooke et al., Universal Bone Cutting Device for Precision Knee Replacement Arthroplasty and Osteotomy, & J. Biomed. Eng'g 45, 47, col. 2, II. 52-57 (1985).
Goble et al., "Minimally Invasive Total Knee Replacement: Principles and.Technique", Orthopedic Clinics of North America, pp. 235-245. (2004).

(56) References Cited

OTHER PUBLICATIONS

*Hudson Surgical Design v. Zimmer Holdings, Inc., Zimmer, Inc., Rush System For Health* and *Rush University Medical Center*, Revised Final Claim Construction Chart, Mar. 11, 2009, 18 pages.
*Hudson Surgical Design v. Zimmer Holdings, Inc., et al., Zimmer, Inc.'s and Zimmer Holdings, Inc.'s* Supplemental Responses to Hudson Surgical Design, Inc.'s First Set of Interrogatories (Nos. 1-18) to Each of Them, 59 pages, Aug. 1, 2008.
Third Party Requester's Written Comments Under 37 C.F.R. .sctn. 1.947 in Response to Patent Owner's Response Under 37 C.F.R. .sctn. 1.945, Inter Partes Reexamination of U.S. Pat. No. 7,344,541, 48 pages, filed Feb. 23, 2011, U.S. Appl. No. 95/001,469.
*Hudson Surgical Design, Inc. v. Biomet, Inc.*, Complaint, Case: 1:10-cv-04459, Document 1 (includes Document 1, 1-1 and 1-2), Filed Jul. 19, 2010, 74 pages.
*Hudson Surgical Design, Inc. v. Biomet, Inc.*, Answer, Affirmative Defenses, and Counterclaim of Biomet, Inc., Case: 1:10-cv-04459, Document 14, Filed Aug. 31, 2010, PageID # 89-104.
*Hudson Surgical Design, Inc. v. Biomet Orthopedics, LLC and Biomet Manufacturing Corporation*, Answer, Affirmative Defenses, and Counterclaim of Biomet Orthopedics, LLC and Biomet Manufacturing Corporation to the First Amended Complaint, Case: 1:10-cv-04459, Document 19, Filed Sep. 28, 2010 PageID# 194-207.
*Hudson Surgical Design, Inc. v. Biomet Orthopedics, LLC and Biomet Manufacturing Corporation*, Hudson Surgical Design Inc.'s Answer to Counterclaims of Biomet Orthopedics, LLC and Biomet Manufacturing Corporation, Case: 1:10-cv-04459, Document 27, Filed Oct. 11, 2010, PageID# 245-249.
*Hudson Surgical Design, Inc. v. Biomet Orthopedics, LLC and Biomet Manufacturing Corporation*, First Amended Complaint, Case: 1:10-cv-04459, Document 17, Filed Sep. 14, 2010, PageID# 108-183.
Reexamination Control No. 95/001,469, U.S. Pat. No. 7,344,541, Patent Owner's Response Under 37 C.F.R 1.945 filed Jan. 24, 2011, 74 pages.
Case 1:08-cv-01566, Document No. 83-3, Exhibit 1, Anatomical Terms, Filed Nov. 17, 2008, 2 pages.
Case 1:08-cv-01566, Document No. 83-4 Exhibit 2, Spatial Terms, Filed Nov. 17, 2008, 2 pages.
Case 1:08-cv-01566, Document No. 83-5, Exhibit 3, *Healthy* vs. *Arthritic Knee*, Filed Nov. 17, 2008, 2 pages.
Case 1:08-ev-01566, Document No. 83-6, Exhibit 4, Post TKA Knee Joint, Filed Nov. 17, 2008, 2 pages.
Case 1:08-cv-01566, Document No. 83-7, Exhibit 5, Knee Implants, Filed Nov. 17, 2008, 2 pages.
Case 1:08-cv-01566, Document No. 83-8, Exhibit 6, *Traditional* vs. *Minimally Invasive*, Nov. 17, 2008, 2 pages.
Case 1:08-cv-01566, Document No. 83-9, Exhibit 7, Filed Nov. 17, 2008, 2 pages.
Case 1:08-cv-01566, Document No. 83-10, Exhibit 8, Total Knee Replacement, Filed Nov. 17, 2008, .COPYRGT. 2000, Swarm Interactive, www.swarminteractive.com, 2 pages.
Case 1:08-cv-01566, Document No. 83-13, Exhibit 11, Deferred Prosecution Agreement, Filed Nov. 17, 2008, 26 pages.
Case 1:08-cv-01566, Document No. 83-16, Exhibit 14, *Hudson Surgical Design, Inc. vs. Zimmer Holdings, Inc.; Zimmer, Inc.; Rush System for Health; and Rush University Medical Center*, Hudson Surgical Design, Inc.'s Oct. 20, 2008, Supplemental Answers to Defendant Rush University Medical Center's First Set of Interrogatories, Filed Nov. 17, 2008, 23 pages.
Case 1:08-cv-01566, Document No. 83-17, Exhibit 15, *Hudson Surgical Design Inc. vs. Zimmer Holdings, Inc.; Zimmer, Inc.; Rush System for Health; and Rush University Medical Center*, Hudson Surgical Design's Oct. 20, 2008, Supplemental Answers to Zimmer, Inc.'s First Set of Interrogatories, Filed Nov. 17, 2008, 21 pages.
Case 1:08-cv-01566, Document No. 83-18, Exhibit 16, Part 1, Zimmer Computer Assisted Solutions Electromagnetic Quad-Spring, Surgical Technique, Filed Nov. 17, 2008, 3 pages.
Case 1:08-cv-01566, Document No. 83-19, Exhibit 16, Part 2, Zimmer Computer Assisted Solutions Electromagnetic Quad-Spring, Surgical Technique, Filed Nov. 17, 2008, 4 pages.
Case 1:08-cv-01566, Document No. 83-20, Exhibit 16, Part 3, Zimmer Computer Assisted Solutions Electromagnetic Quad-Spring, Surgical Technique, Filed Nov. 17, 2008, 4 pages.
Case 1:08-cv-01566, Document No. 83-23, Exhibit 19, Haines Family Tree for '541 Patent, Filed Nov. 17, 2008, 2 pages.
Case 1:08-cv-01566, Document No. 83-24, Exhibit 20, *Hudson Surgical Design, Inc. vs. Zimmer Holdings, Inc.; Zimmer, Inc.; Rush System for Health; and Rush University Medical Center*, Joint Claim Construction Chart, Filed Nov. 17, 2008, 14 pages.
Case 1:08-cv-001566, Document No. 83-25, Exhibit 21, Filed Nov. 17, 2008, 2 pages.
Case 1:08-cv-01566, Document No. 83-29, Exhibit 25, Webster's Ninth New Collegiate Dictionary (includes p. 905), Filed Nov. 17, 2008, .COPYRGT. 1985, 5 pages.
Case 1:08-cv-01566, Document No. 83-30, Exhibit 26, Figure 18 of Patent No. 7,334,541, Filed Nov. 17, 2008 , 2 pages.
Case 1:08-cv-01566, Document No. 83-31, Exhibit 27, Langenscheidt Merriam-Webster Medical Dictionary, Filed Nov. 17, 2008, .COPYRGT. 2006, 6 pages.
Case 1:08-cv-01566, Document No. 83-33, Exhibit 29, Claim 21 of U.S. Patent No. 7,334,541, Filed Nov. 17, 2008, 2 pages.
Case 1:08-cv-01566, Document No. 83-34, Exhibit 30, Webster's Ninth New Collegiate Dictionary (includes pp. 56 & 73 of the dictionary), Filed Nov. 17, 2008, .COPYRGT. 1985, 6 pages.
Case 1:08-cv-01566, Document No. 83-35, Exhibit 31, Mosby's Medical Dictionary 7.sup.th Edition, Filed Nov. 17, 2008 .COPYRGT. 2006, 6 pages.
Case 1:08-cv-01566, Document No. 83-2, *Hudson Surgical Design, Inc. vs Zimmer Holdings, Inc.; Zimmer, Inc.; Rush System for Health; and Rush University Medical Center*, Index of Exhibits (Exhibit Nos. 1-31) to Hudson Surgical Design, Inc.'s Opening Brief on Claim Construction, Filed Nov. 17, 2008, 2 pages.
Case 1:08-cv-01566, Document No. 95-9, Exhibit 8, *Hudson Surgical Design, Inc. vs. Zimmer Holdings, Inc.; Zimmer, Inc.; Rush System for Health; and Rush University Medical Center*, Joint Claim Construction Chart Filed dated Oct. 24, 2008, 14 pages.
*Hudson Surgical Design, Inc. v. Zimmer Holdings, Inc., Zimmer Inc., Rush System for Health and Rush University Medical Center*, Defendant's Responsive Claim Construction Brief, Case No. 1:08-cv-01566, Document No. 95, Filed Dec. 8, 2008, pp. 1-40 (also included is Exhibit 1-8).
T.D.V. Cooke et al., Universal Bone Cutting Device for Precision Knee Replacement Arthoplasty and Osteotomy, 7 J. Biomed. Eng'g 45, 47, col. 2, ll. 52-57 (1985).
Globe, E. Marlow and Justin, Daniel F., Minimally Invasive Total Knee Replacement: Principles and Technique, Orthop. Clin. N. Am. 35 (2004) 235-245.
Whiteside Ortholoc Total Knee System: Surgical Procedure, Dow Corning Wright, pp. WMT00001-WMT000040, Jun. 1985.
Zimmer, Insall/Burstein II, Constrained Condylar: Modular Knee System, Surgical Technique, copyright 1989.
Zimmer, The Miller/Galante Advantage: Total Knee System, pp. ZH000159653-ZH000159668.
Whiteside Ortholoc Total Knee System, Dow Corning Wright, pp. ZH000109679-ZH000109690.
Zimmer, Insall/Burnstein II, Modular Knee System, Surgical Technique, pp. ZH000109691-ZH000109710.
*Hudson Surgical Design, Inc. v. Zimmer Holdings. Inc., Zimmer, Inc., Rush System for Health and Rush University Medical Center*, First Amended Complaint, Filed Apr. 11, 2008, Case: 1:08-cv-01566, pp. 1-8.
*Hudson Surgical Design, Inc. v. Zimmer Holdings, Inc., Zimmer, Inc., Rush System for Health and Rush University Medical Center*. Answer, Affirmative Defenses and Counterclaims of Zimmer Holdings, Inc. and Zimmer, Inc. Filed May 9, 2008, Case: 1:08-cv-01566, pp. 1-10.
*Hudson Surgical Design Inc. v. Zimmer Holdings, Inc., Zimmer, Inc., Rush System for Health and Rush University Medical Center*. Rush

(56) References Cited

OTHER PUBLICATIONS

System for Health's and Rush University Medical Center' Answer to First Amended Complaint, Filed May 9, 2008, Case: 1:08-cv-01566, pp. 1-7.
*Hudson Surgical Design, Inc. v. Zimmer Holdings, Inc., Zimmer, Inc., Rush System for Health and Rush University Medical Center*. Plaintiffs Reply to Counterclaims of Defendants Zimmer Holdings, Inc. and Zimmer, Inc., Case:1:08-cv-01566, Filed May 19, 2008 pp. 1-5.
Documents labeled ZHG000157188-ZHG000157198 disclosed in *HSO, Inc.* v. *Zimmer et al.*, 11 pages.
Documents labeled ZHG000157226-ZHG000157253 disclosed in *HSO, Inc.* v. *Zimmer et al.*, 28 pages.
Documents labeled ZHG000157254-ZHG000157270 disclosed in *HSO, Inc.* v. *Zimmer et al.*, 17 pages.
*Hudson Surgical Design, Inc. v. Zimmer Holdings, Inc., Zimmer, Inc., Rush System for Health and Rush University Medical Center*, Case No. 1:08-cv-01566, Civil Action No. 08C1566, Document 83, Filed Nov. 17, 2008, 40 pages.
*Hudson Surgical Design, Inc. v. Zimmer Holdings, Inc., Zimmer Inc., Rush System for Health and Rush-Presbyterian-St. Luke's Medical Center, Inc.*, Civil Action No. 08C1566, Zimmer, Inc 's and Zimmer Holdings, Inc.'s Supplemental Responses to Hudson Surgical Design, Inc.'s First Set of Interrogatories (Nos. 1-18) to each of them.
*Hudson Surgical Design, Inc. v. Zimmer Holdings, Inc., Zimmer, Inc. Rush System for Health and Rush University Medical Center*, Civil Action No. 08C1566, Statement of Thomas D. Petersen, M.D. (including Exhibit A-G), Dated Sep. 2, 2009.
*Hudson Surgical Design, Inc. v. Zimmer Holdings, Inc. et al.*, Notification of Docket Entry, Filed Sep. 21, 2009, Document 138, Case No. 1:08-cv-01566, 1 page.
*Hudson Surgical Design, Inc. v Zimmer Holdings, Inc.*, et. al, Case No. 1:08-cv01566, Jan. 27, 2009, vol. 1-A, Transcript of Markman Hearing Before the Honorable Virginia M. Kendal United States District Judge, pp. 1-66 & index pp. 1-12.
*Hudson Surgical Design, Inc. v Zimmer Holdings, Inc.*, et. al, Case No. 1:08-cv-01566, Jan. 27, 2009, vol. 1-B, Transcript of Markman Hearing Before the Honorable Virginia M. Kendal United States District Judge, pp. 67-133, & index pp. 1-13.
*Hudson Surgical Design, Inc. v. Zimmer Holdings, Inc., Zimmer, Inc., Rush System for Health and Rush University Medical Center*, Hudson Surgical Design, Inc.'s Reply Brief on Claim Construction, Civil Action No. 08C1566 Document No. 97, Filed Dec. 19, 2008, pp. 1-28.
*Hudson Surgical Design, Inc. v. Zimmer Holdings, Inc., Zimmer Inc. Rush System for Health and Rush University Medical Center*, Civil Action No. 08C1566, Statement of Dr. E Marlowe Goble (including Exhibit A-1).
Demand for Arbitration, *Smith & Nephew, Inc.* vs. *Hudson Surgical Design, Inc.*, 21 pages, dated Aug. 16, 2011.
Application and File History for U.S. Appl. No. 13/169,728, filed Jun. 27, 2011, Inventor: Haines et al.
Application and File History for U.S. Appl. No. 10/977,365, filed Oct. 29, 2004, Inventor: Haines et al.
Application and File History for U.S. Appl. No. 08/300,379, filed Sep. 2, 1994, Inventor: Haines et al.
Application and File History for U.S. Appl. No. 08/342,143, filed Nov. 18, 1994, Inventor: Haines et al.
Application and File History for U.S. Appl. No. 08/479,363, filed Jun. 7, 1995, Inventor: Haines et al.
Application and File History for U.S. Appl. No. 08/603,582, filed Feb. 20, 1996, Inventor: Haines et al.
Application and File History for U.S. Appl. No. 08/649,465, filed May 17, 1996, Inventor: Haines et al.
Application and File History for U.S. Appl. No. 08/892,286, filed Jul. 14, 1997; Inventor: Haines et al.
Application and File History for U.S. Appl. No. 09/156,161, filed Sep. 17, 1998, Inventor: Haines et al.
Application and File History for U.S. Appl. No. 09/261,528, filed Mar. 3, 1999, Inventor: Haines et al.
Application and File History for U.S. Appl. No. 09/799,325, filed Mar. 5, 2001, Inventor: Haines et al.
Application and File History for U.S. Appl. No. 10/756,817, filed Jan. 13, 2004, Inventor: Haines.
Application and File History for U.S. Appl. No. 10/958,203, filed Oct. 4, 2004, Inventor: Haines et al.
Application and File History for U.S. Appl. No. 10/967,673, filed Oct. 22, 2004, Inventor: Haines.
Application and File History for U.S. Appl. No. 11/933,298, filed Oct. 31, 2007, Inventor: Haines.
Application and File History for U.S. Appl. No. 12/638,692, filed Dec. 15, 2009, Inventor: Haines.
Application and File History for U.S. Appl. No. 13/291,701, filed Nov. 8, 2011, Inventor: Haines.
Application and File History for U.S. Appl. No. 12/757,778, filed Apr. 9, 2010, Inventor: Haines.
Application and File History for U.S. Appl. No. 13/311,798, filed Dec. 6. 2011, Inventor: Haines.
Application and File History for U.S. Appl. No. 14/753,857, filed Jun. 29, 2015, Inventor: Haines.
*Hudson Surgical Design, Inc.* v. *Zimmer Holdings, Inc. Zimmer Inc., Rush System for Health and Rush University Medical Center*, Hudson Surgical Design, Inc's Opening Brief on Claim Construction Case No. 1:08-cv-01566, Civil Action No. 08C1566, Document No. 83, Filed Nov. 17, 2008, pp. 1-40 (also includes Exhibits 1-40).
Uvehammer et al., "In Vivo Kinematics of Total Knee Arthroplasty: Concave Versus Posterior-Stabilised Tibial Joint Surface", vol. 82-B, No. 4, May 2000, pp. 499-505.
Control No. 95/002,152, Third Party Requester's Written Comments Under 37 C.F.R 1.947 and Declaration of David Alan Fischer, M.D., as filed Jan. 30, 2013 with the U.S. Patent and Trademark Office, 120 pages.
Reexamination Control No. 95/002,152 re: U.S. Pat. No. 7,967,822, Request for Inter Partes Reexamination, filed Sep. 7, 2012, 574 pages.
Reexamination Control No. 95/002,152 re: U.S. Pat. No. 7,967,822, Supplemental/Corrected Patent Owner's Response Under 37 CFR 1.945, 60 pages, as filed Jan. 10, 2013.
Reexamination Control No. 95/002,152 re: U.S. Pat. No. 7,967,822, Order Granting/Denying Request for Inter Partes ReExamination, Oct. 26, 2012, 35 pages.
Reexamination Control No. 95/002,152 re: U.S. Pat. No. 7,967,822, Office Action in Inter Partes Reexamination, dated Oct. 29, 2012, 15 pages.
Control No. 95/001,469 re: U.S. Pat. No. 7,344,541, Respondent Brief, as filed Dec. 3, 2012, 34 pages.
Control No. 95/001,469 re: U.S. Pat. No. 7,344,541, Third Party Requesters' Respondent Brief Under 37 CFR 41.68, as filed Nov. 21, 2012, 27 pages.
Control No. 95/001,469 re: U.S. Pat. No. 7,344,541, Third Party Requester's Cross Appeal Brief Under 37 CFR 41.67, as filed Nov. 1, 2012, 51 pages.
Control No. 95/001,469 re: U.S. Pat. No. 7,344,541, Appellant's Brief (revised), filed Oct. 23, 2012, 1471 pages.
Control No. 95/001,469 re: U.S. Pat. No. 7,344,541, Appellant's Brief , filed Sep. 13, 2012, 92 pages.
Control No. 95/001,469 re: U.S. Pat. No. 7,344,541, Right of Notice of Appeal Notice, mailed May 21, 2012.
Control No. 95/001,469 re: U.S. Pat. No. 7,344,541, Third Party Requester's Written Comments Under 37 CFR 1.951(b) in Response to Patent Owner's Response, as filed Oct. 31, 2011, 57 pages.
Control No. 95/001,469 re: U.S. Pat. No. 7,344,541, Patent Owner Comments/Amendments Under 37 CFR 1.951, as filed Sep. 29, 2011, 85 pages.
Control No. 95/001,469 re: U.S. Pat. No. 7,344,541, Third Party Requester's Written Comments in Response to Patent Owner's Response to Notice of Defective Paper, as filed May 23, 2011, 11 pages.
Control No. 95/001,469 re: U.S. Pat. No. 7,344,541, Patent Owner's Response to Notice of Defective Paper, as filed Apr. 22, 2011, 51 pages.

(56) References Cited

OTHER PUBLICATIONS

Control No. 95/001,469 re: U.S. Pat. No. 7,344,541, Third Party Requester's Written Comments in Response to Patent Owners Response, as filed Feb. 23, 2011, 48 pages.
Control No. 95/001,469 re: U.S. Pat. No. 7,344,541, Patent Owner's Response Under 37 CFR 1.945, as filed Jan. 24, 2011, 74 pages.
Control No. 95/001,469 re: U.S. Pat. No. 7,344,541, Non Final Action. mailed Nov. 23, 2010.
Control No. 95/001,469 re: U.S. Pat. No. 7,344,541, Determination—Reexam Ordered, mailed Nov. 10, 2010.
Klaus Radermacher et al., Computer-Integrated Orthopedic Surgery: Connection of Planning and Execution in Surgical Intervention, in Computer-Integrated Surgery, (Russell H. Taylor et al. eds., 1996), 15 pages.
Zimmer Holdings, Inc and Zimmer, Inc., Casey total knee, 1976, 22 pages.
Zimmer Holdings, Inc. and Zimmer, Inc., NexGen.RTM. Complete Knee Solution, 1996, 31 pages.
Comments on Third Party Requester's Request for Rehearing, Filed in Inter Partes Reexamination Control No. 95/001,469, on Jun. 12, 2014.
Third Party Requester's Comments in Opposition to Owner's Request for Rehearing Under 37 C.F.R. .sctn. 41.79, Filed in Inter Partes Reexamination Control No. 95/001,469, on Jun. 9, 2014.
Third Party Requester's Request for Rehearing Under 37 C.F.R. .sctn. 41.79, Filed in Inter Partes Reexamination Control No. 95/001,469, May 30, 2014.
Request for Rehearing, Filed in Inter Partes Reexamination Control No. 95/001,469, on May 9, 2014.
Patent Trial and Appeal Board Decision on Appeal, Filed in Inter Partes Reexamination Control No. 95/001,469 on Apr. 30, 2014.
Notice of Cross Appeal by Third Party Requester, Filed in Inter Partes Reexamination Control No. 95/002,152, on Oct. 30, 2014.
Notice of Appeal, Filed in Inter Partes Reexamination Control No. 95/002,152, on Oct. 22, 2014.
Right of Appeal Notice (RAN), Filed in Inter Partes Reexamination Control No. 95/002,152, on Sep. 23, 2014.
Action Closing Prosecution, Filed in Inter Partes Reexamination Control No. 95/002,152, on Jun. 27, 2014.
Third Party Requester's Written Comments Under 37 C.F.R. .sctn. 1.947, Filed in Inter Partes Reexamination Control No. 95/002,152, on Mar. 21, 2014.
Patent Owner's Response to Second Office Action Under 37 CFR 1.945, Filed in Inter Partes Reexamination Control No. 95/002,152, on Feb. 20, 2014.
Affidavit/Declaration (Timothy G. Haines) Pursuant to 37 C.F.R. .sctn..sctn. 1.116(e) and 1.132, Filed in Inter Partes Reexamination Control No. 95/002,152, on Feb. 20, 2014.
Second Declaration (G. Klaud Miller, M.D.) Pursuant to 37 C.F.R. .sctn..sctn. 1.116(e) and 1.132, Filed in Inter Partes Reexamination Control No. 95/002,152, on Feb. 20, 2014.
Non-Final Office Action in Inter Partes Reexamination Control No. 95/002,152, Mailed Dec. 20, 2013.
Affidavit/Declaration (David Alan Fisher, M.D.), Filed in Inter Partes Reexamination Control No. 95/002,152, on Oct. 2, 2013.
Third Party Requester's Written Comments Under 37 C.F.R. .sctn. 1.947, Filed in Inter Partes Reexamination Control No. 95/002,152, on Oct. 2, 2013.
Declaration (G. Klaud Miller, M.D.) Pursuant to 37 C.F.R. .sctn..sctn. 1.116(e) and 1.132, Filed in Inter Partes Reexamination Control No. 95/002,152, on Sep. 3, 2013.
Supplemental/Corrected Patent Owner's Response under 37 CFR 1.945, filed in Inter Partes Reexamination Control No. 95/002,153, on Sep. 3, 2013.
Application and File History for Control No. 95/002,152, filed Sep. 7, 2012. Inventors: Haines.
Application and File History for Control No. 95/001,469, filed Oct. 15, 2010. Inventors: Haines.
U.S . Court of Appeals for the Federal Circuit, *Biomet Orthopedics, LLC* v. *Puget Bioventures, LLC* formerly Hudson Surgical Design, Inc., Opening Brief for Appellant, filed May 18, 2015.
U.S. Court of Appeals for the Federal Circuit, *Biomet Orthopedics, LLC* v. *Puget Bioventures, LLC* formerly Hudson Surgical Design, Inc., Response Brief of Appellee, filed Jul. 1, 2015.
U.S. Court of Appeals for the Federal Circuit, *Biomet Orthopedics, LLC* v. *Puget Bioventures, LLC* formerly Hudson Surgical Design, Inc., Reply Brief for Appellant, filed Jul. 20, 2015.
Reexamination Control No. 95/002,152, Appellant's Brief, filed Dec. 22, 2014.
Reexamination Control No. 95/002,152, Third Party Requester's Respondent's Brief, filed Jan. 22, 2015.
Reexamination Control No. 95/002,152, Appellant's Rebuttal Brief, filed Sep. 30, 2015.
Reexamination Control No. 95/002,152, Third Party Requester's Appellant's Brief, filed Dec. 30, 2014.
File History for Control No. 95/002,152, filed Sep. 7, 2012.
File History for Control No. 95/001,469, filed Oct. 15, 2010.

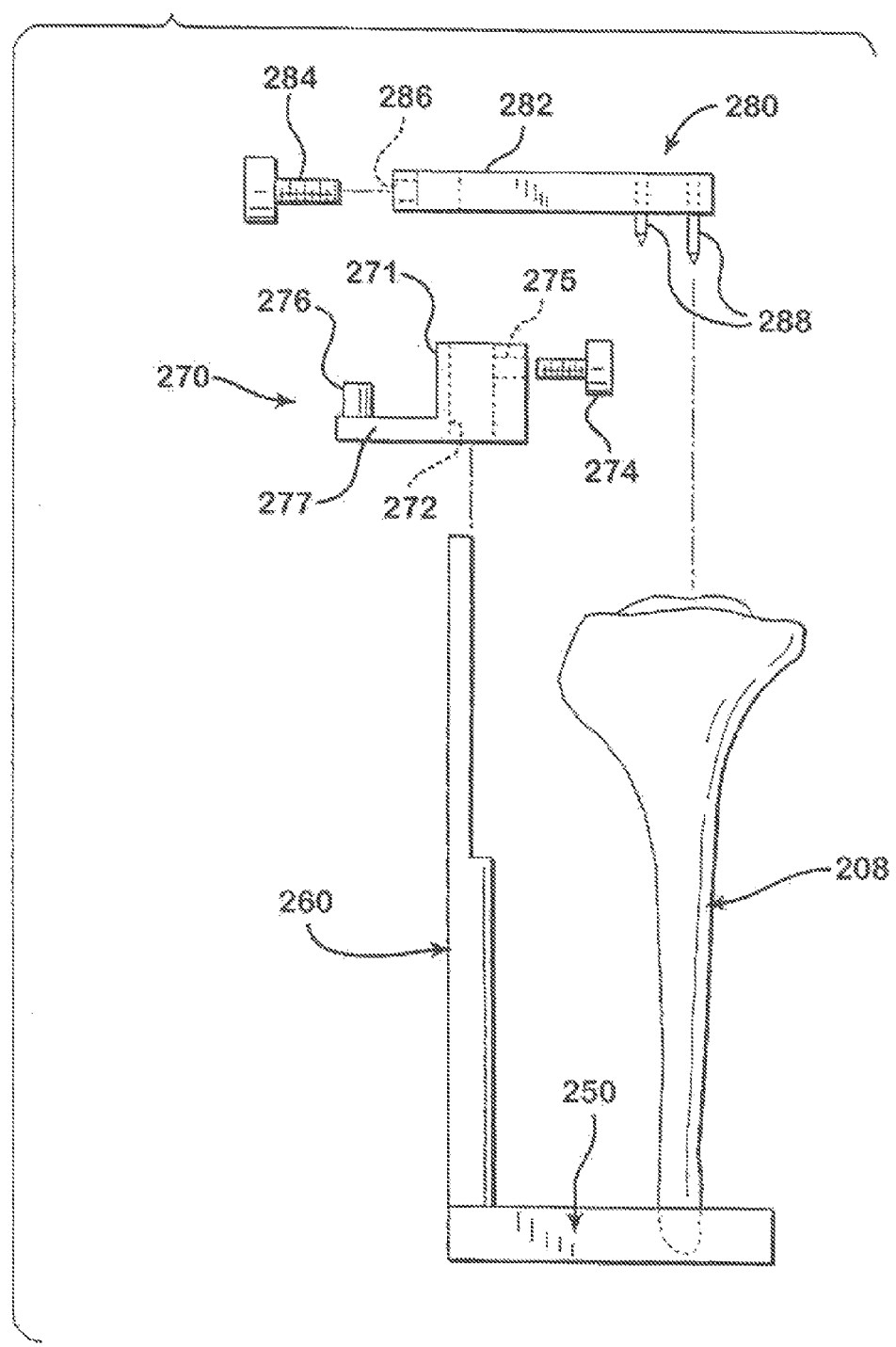

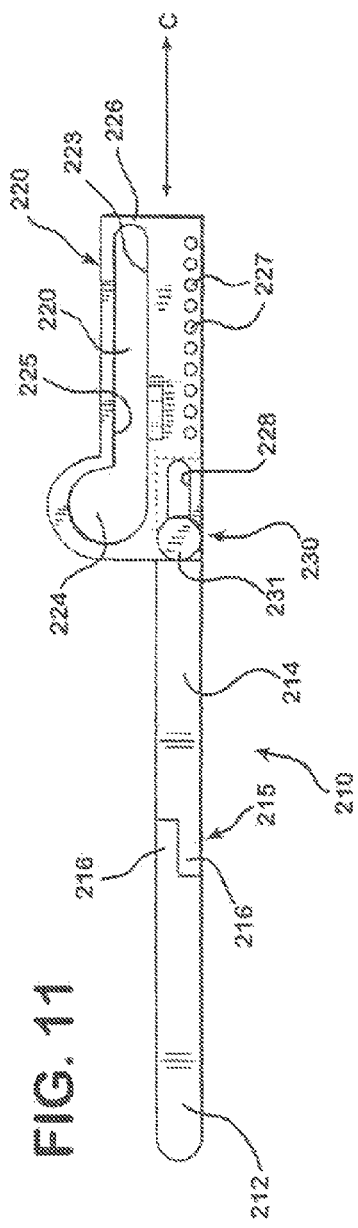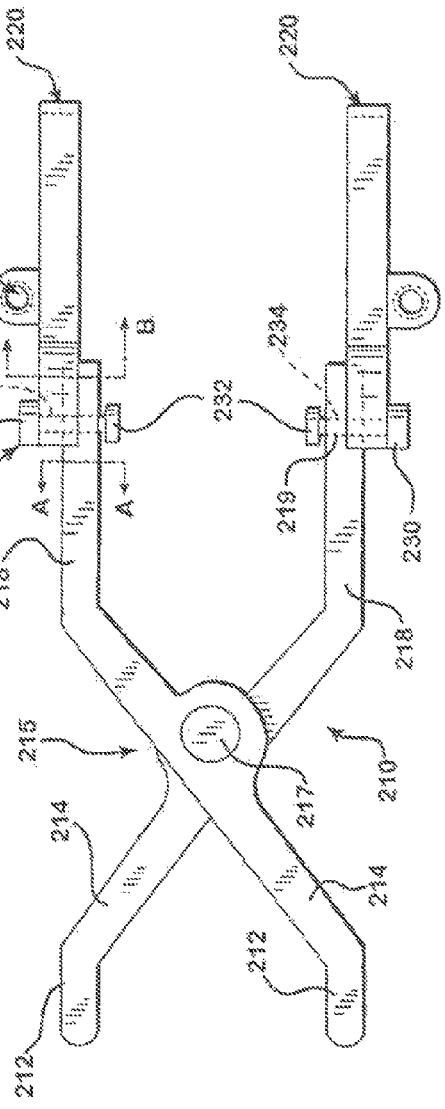

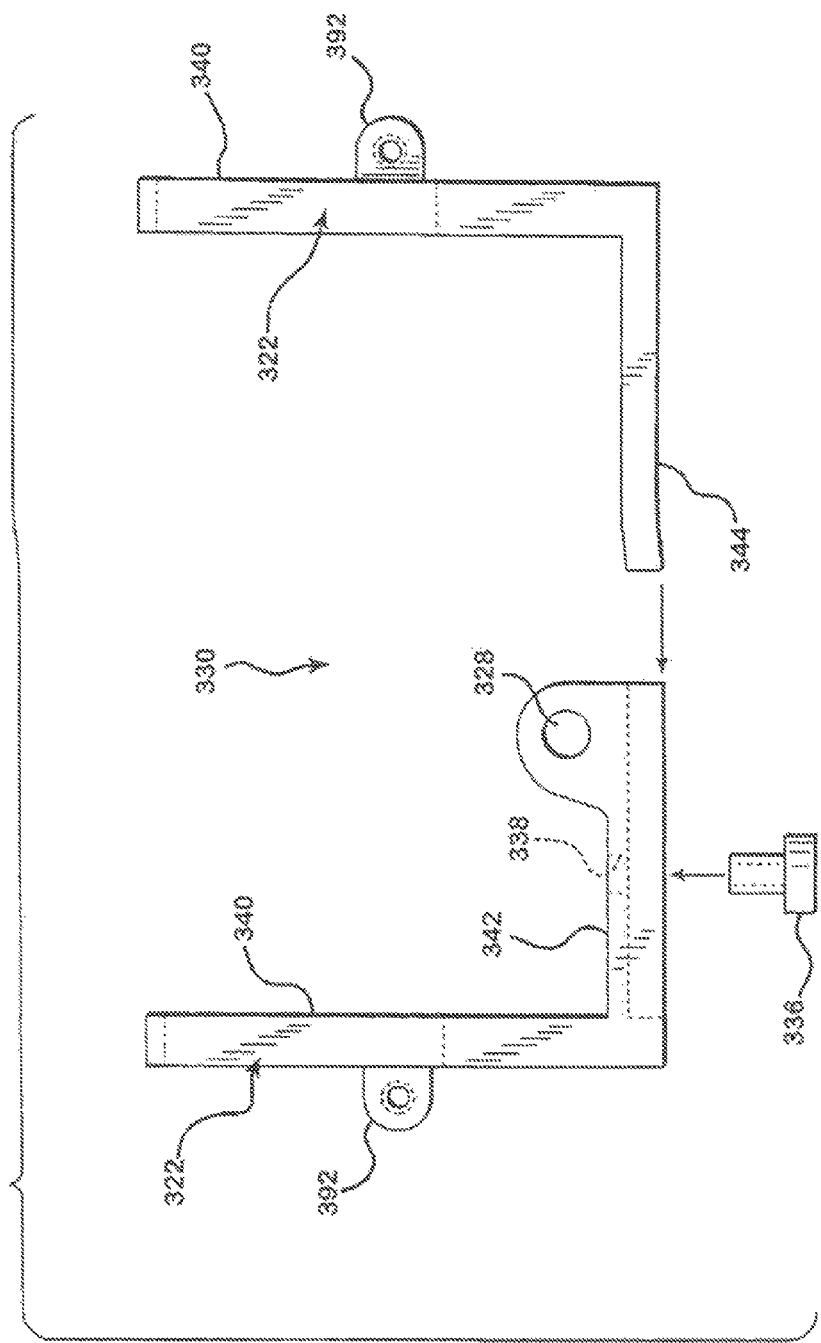

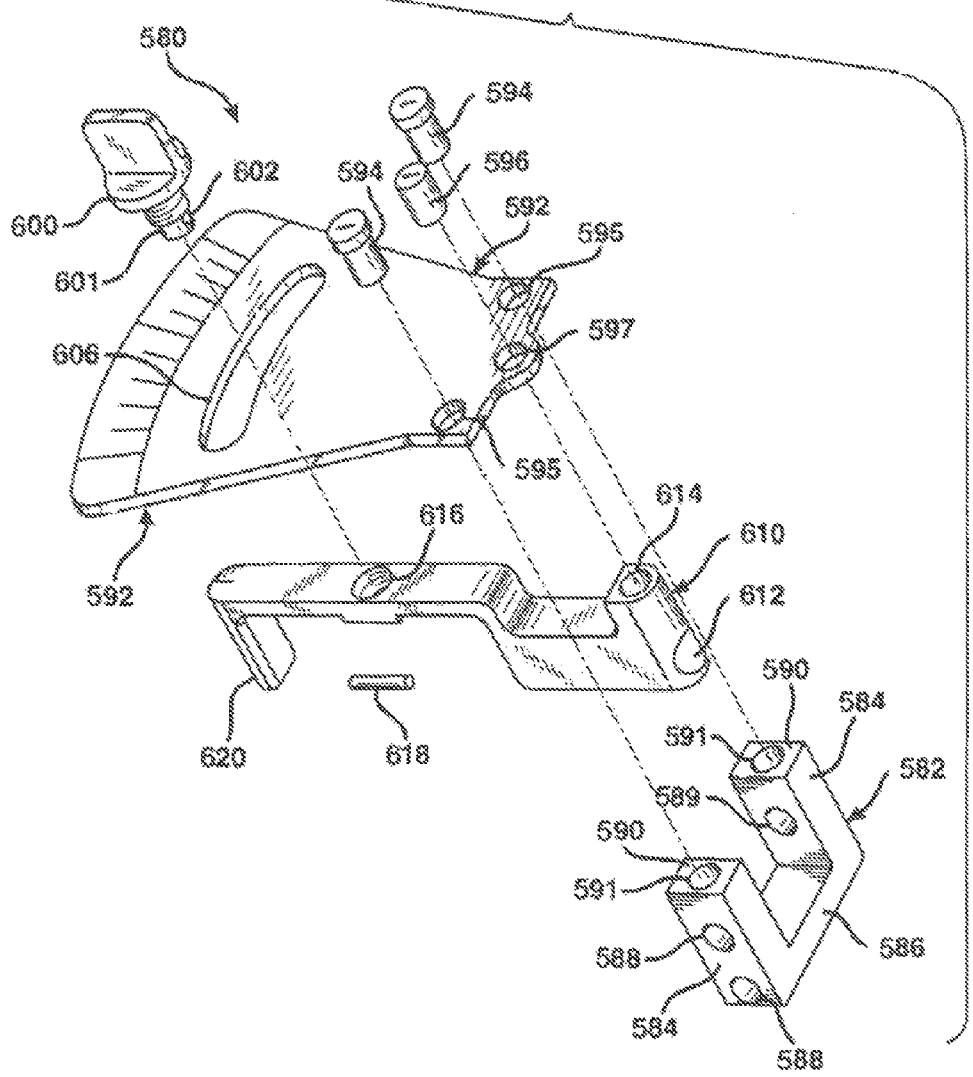

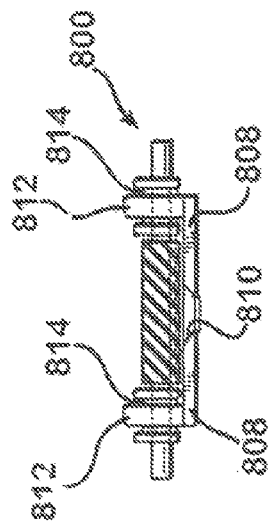
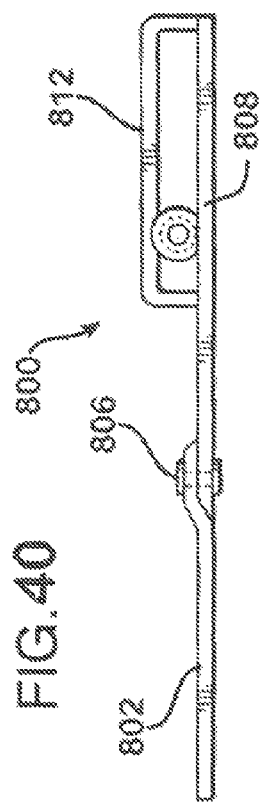
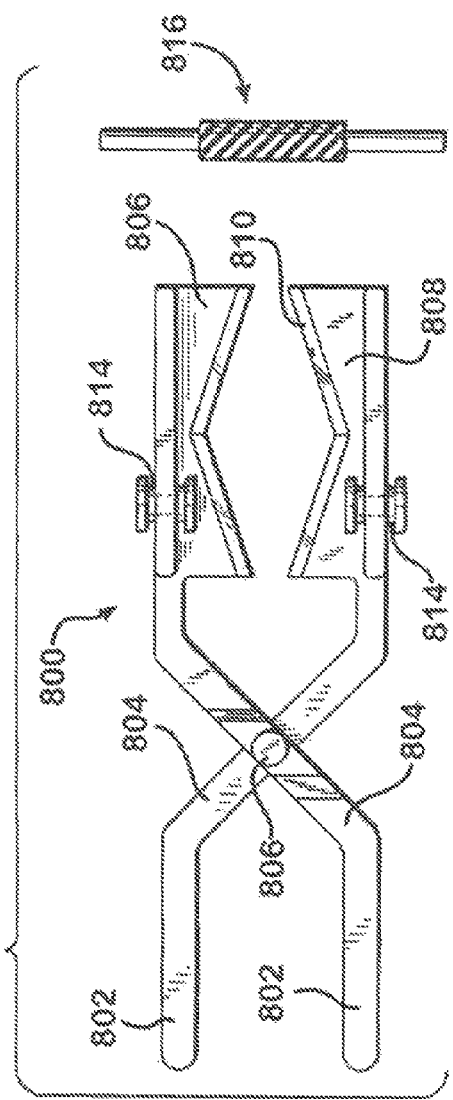
FIG. 40
FIG. 41
FIG. 42

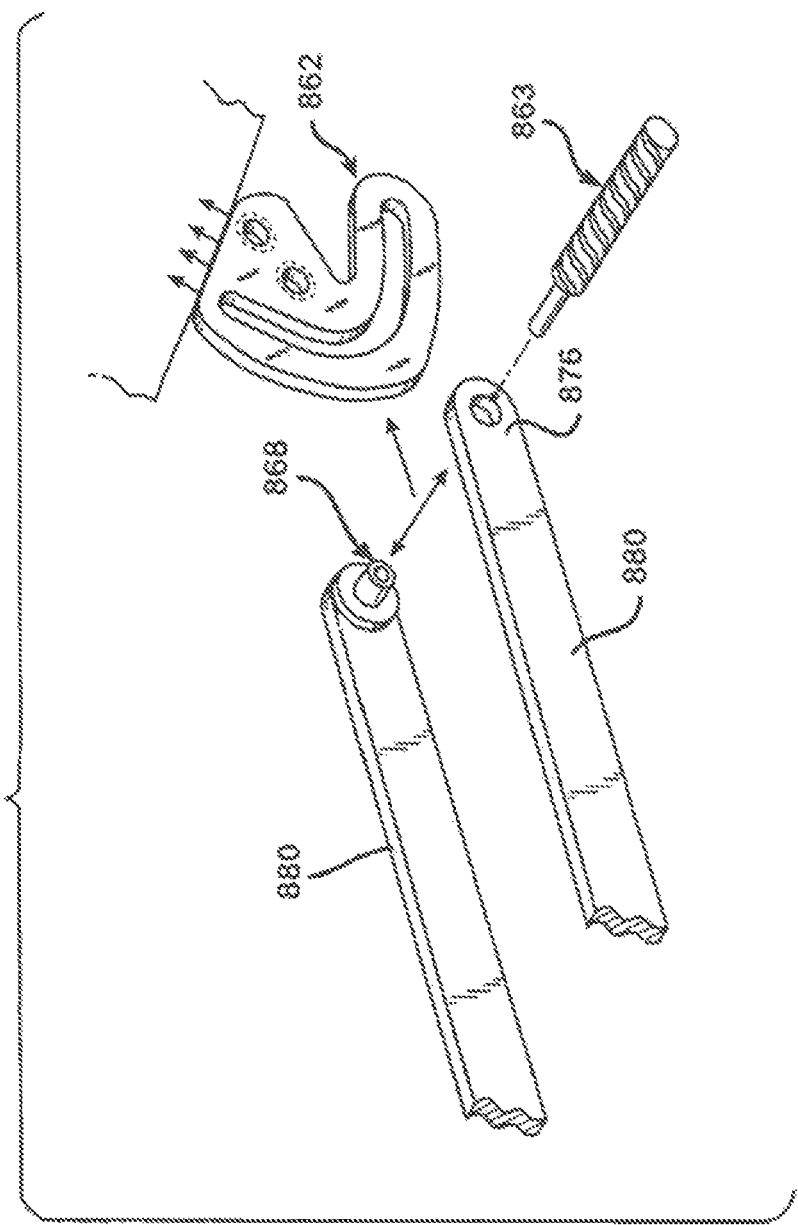

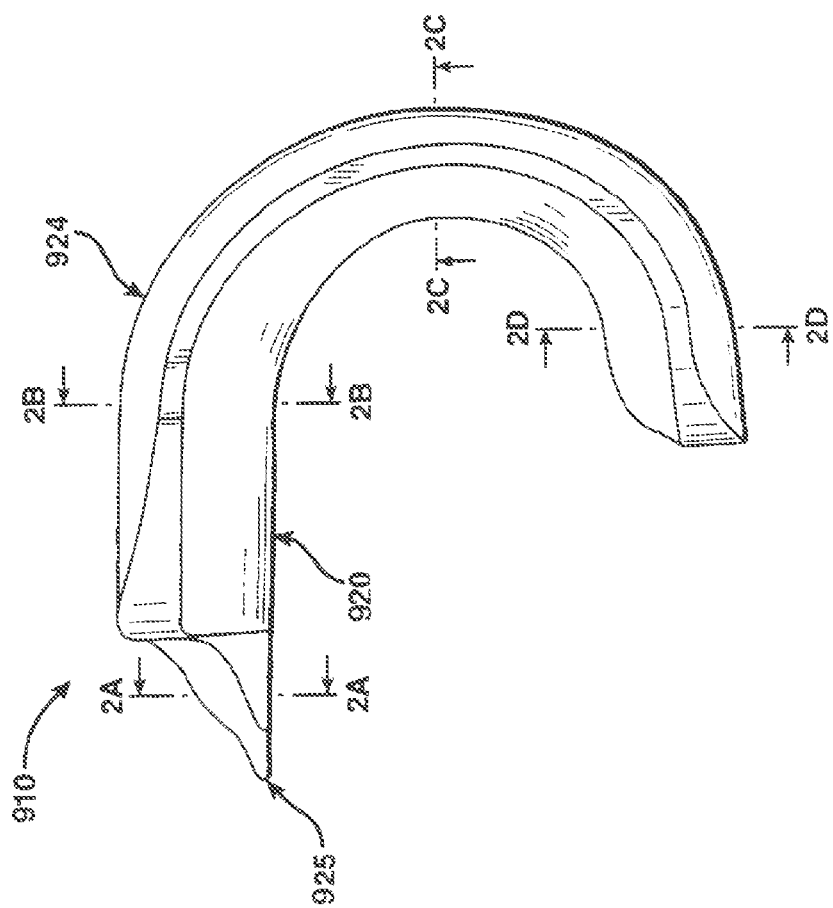

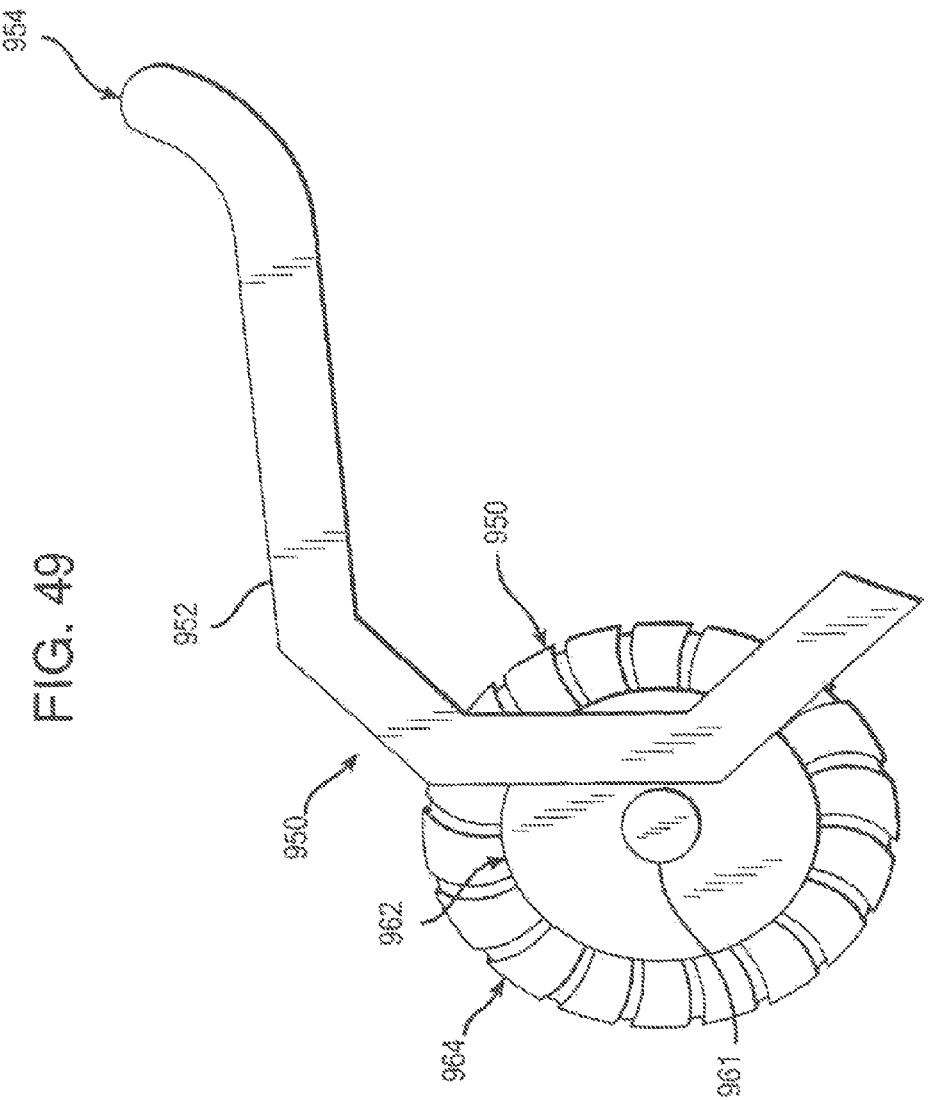

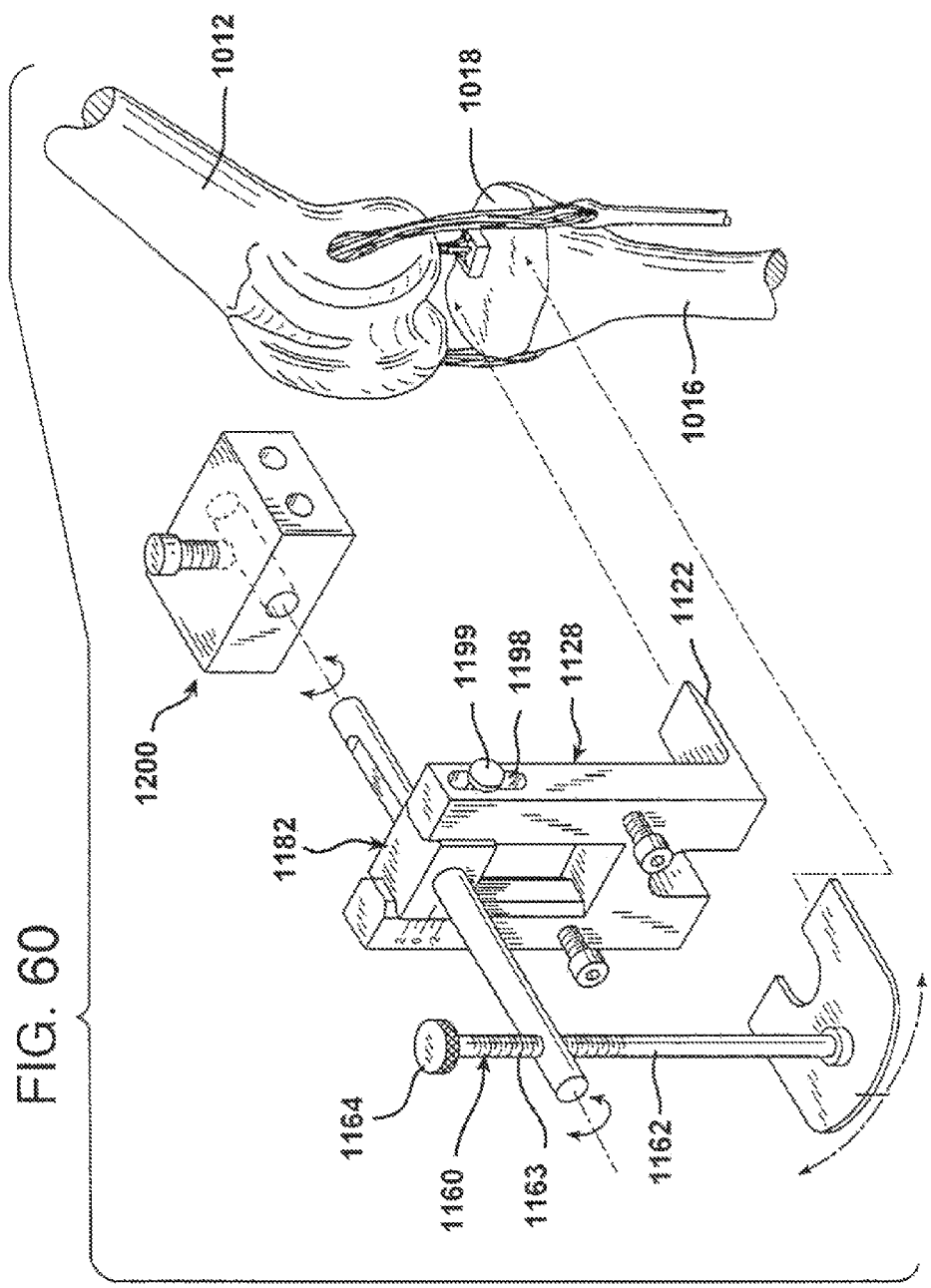

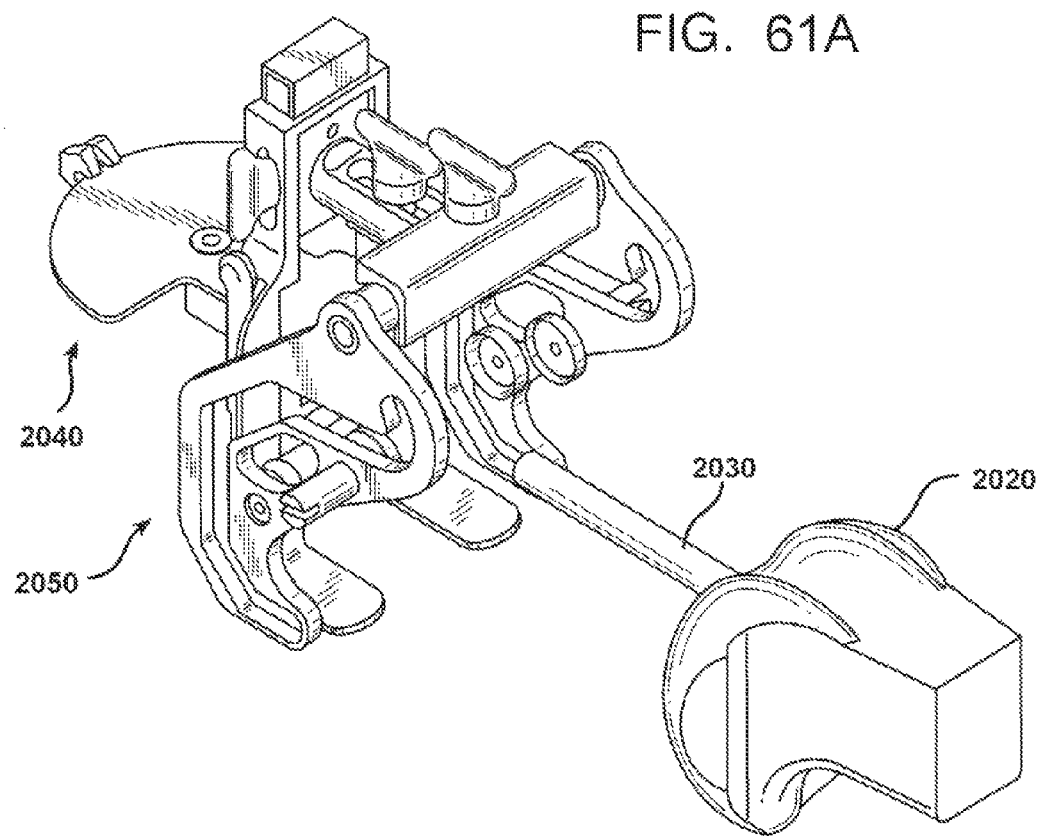

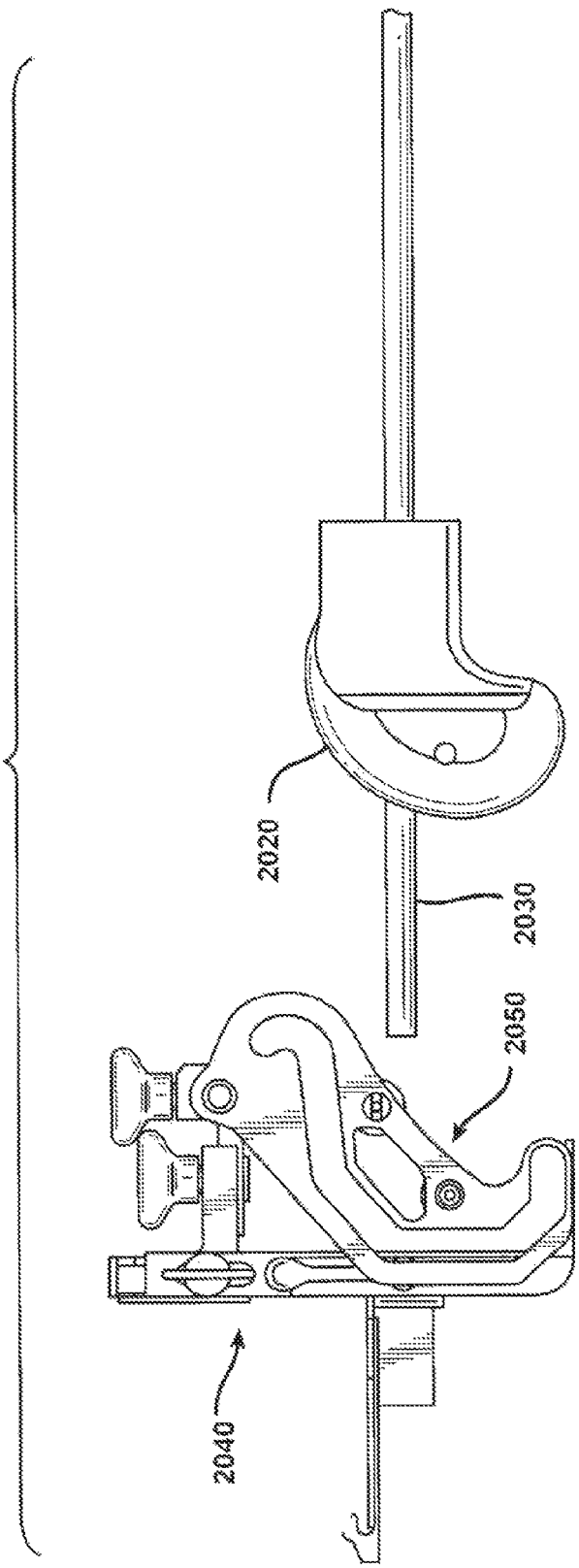

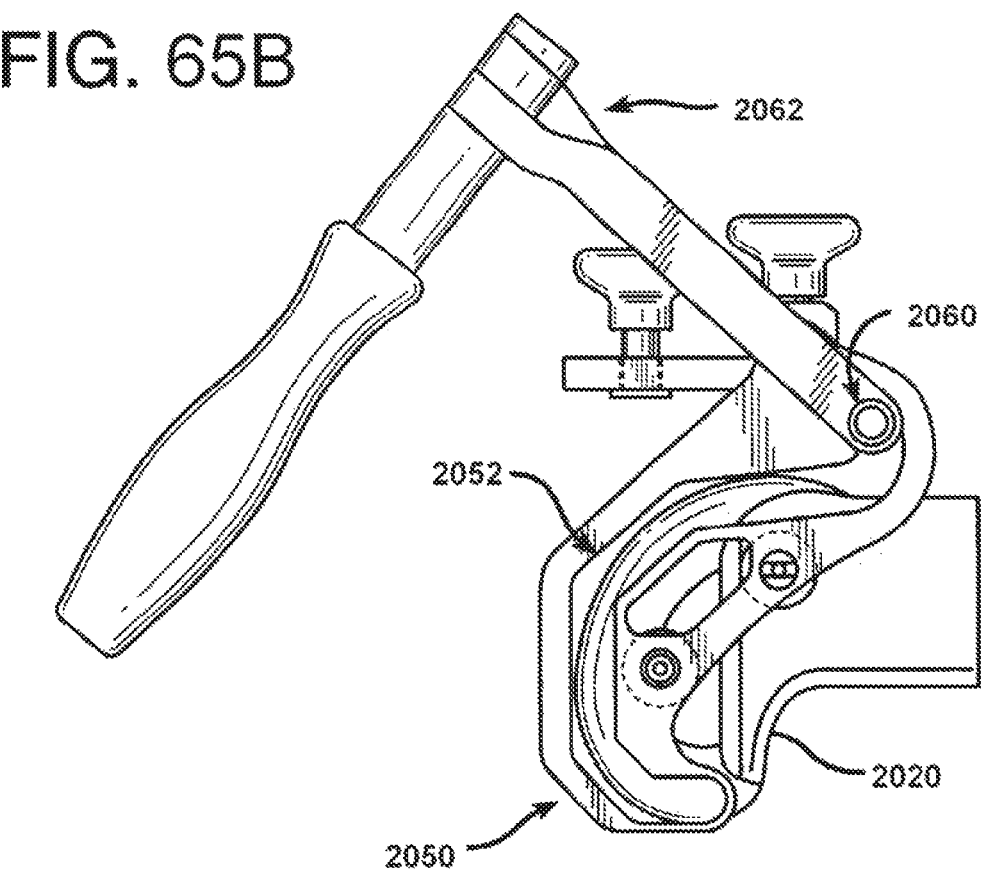

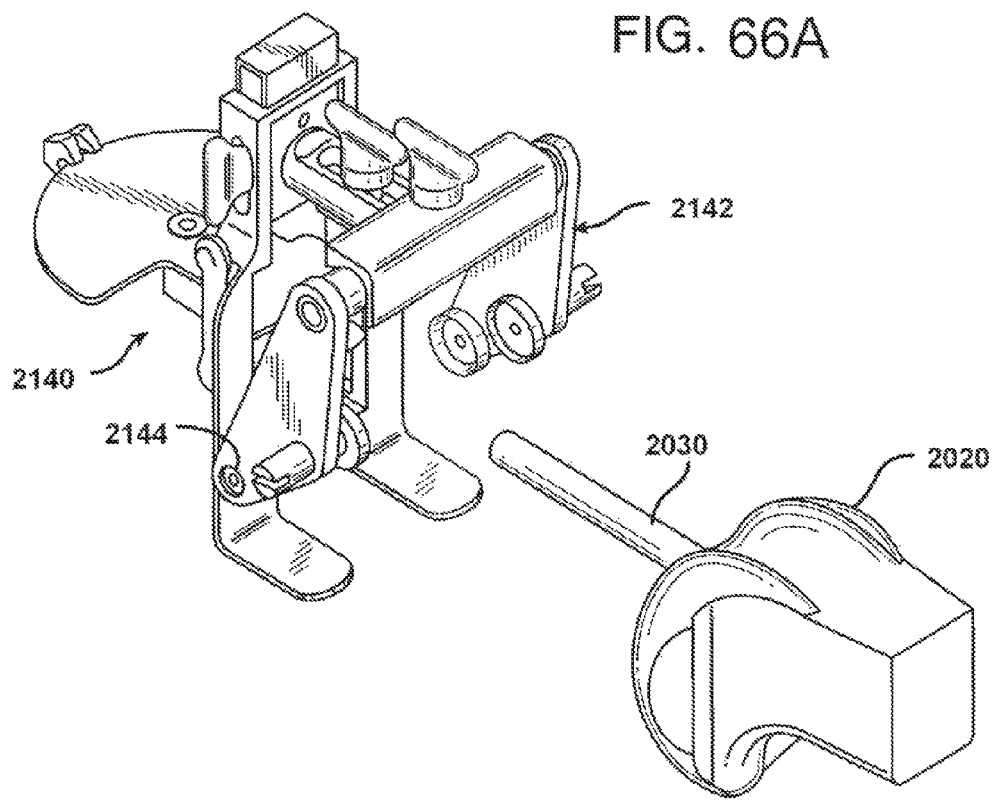

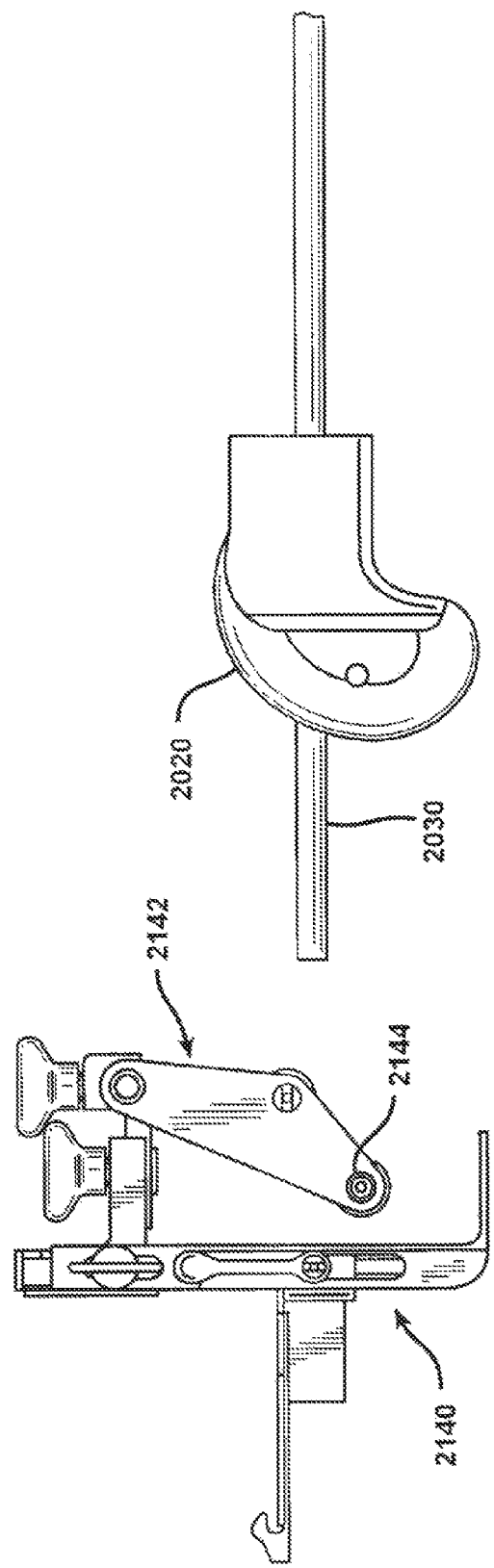

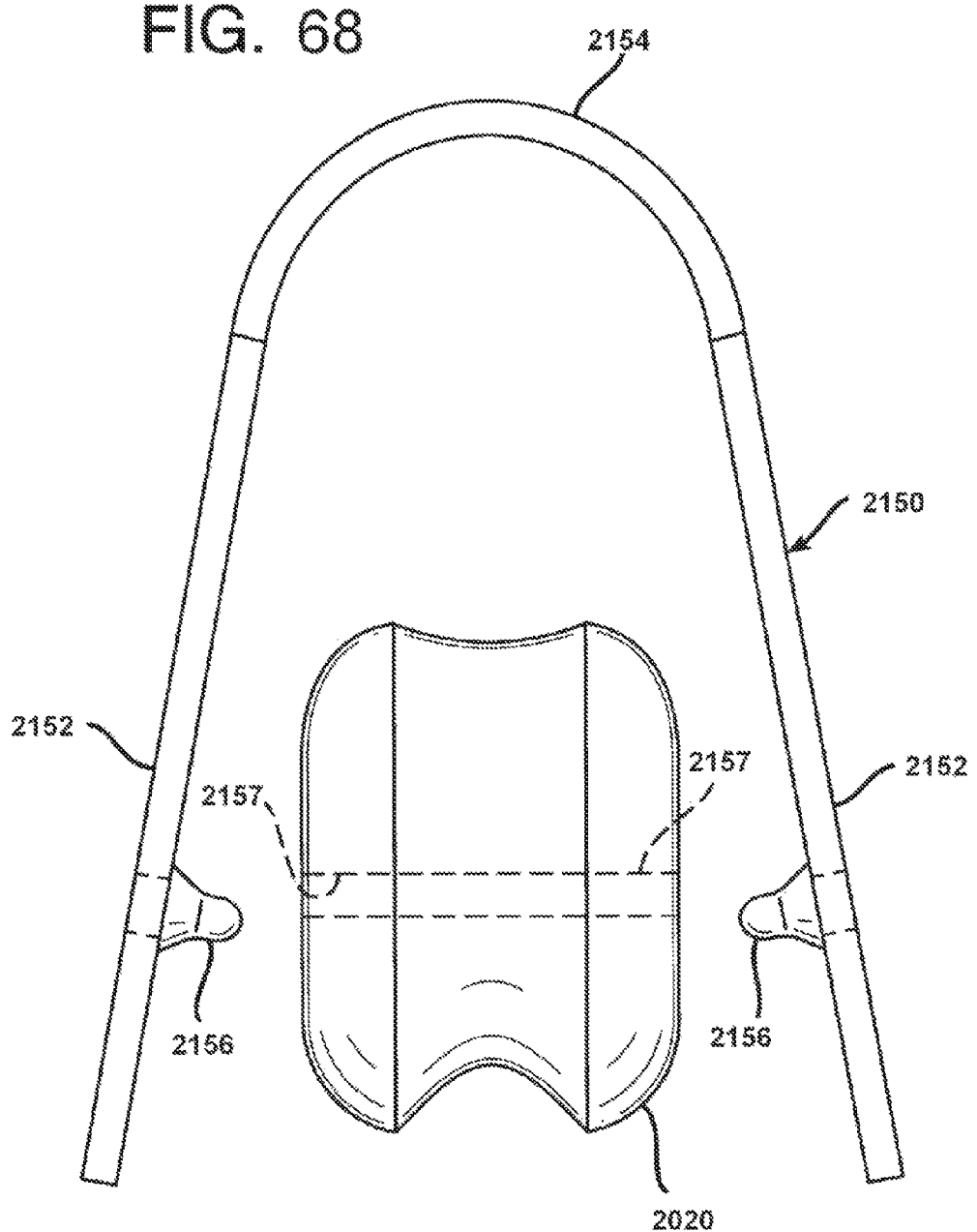

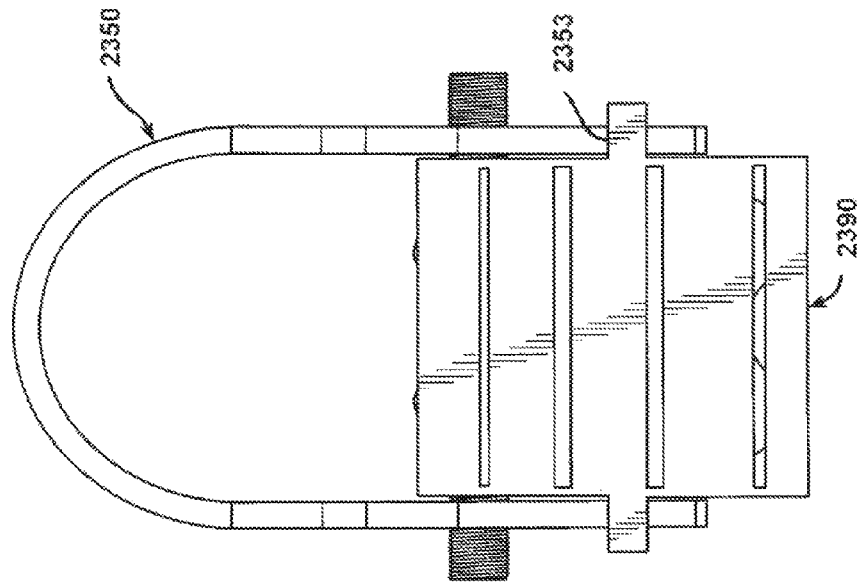
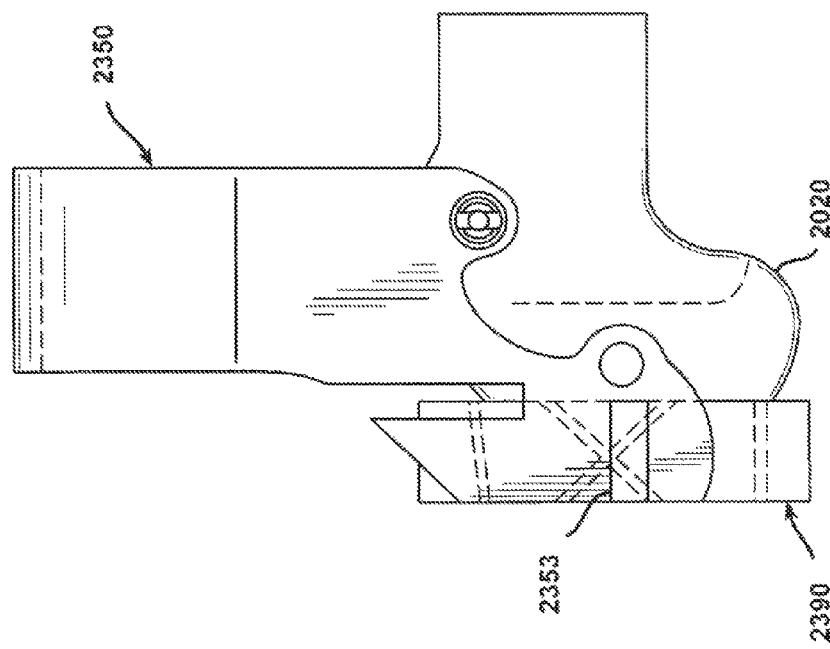

METHOD AND APPARATUS FOR TOTAL KNEE ARTHROPLASTY

RELATED APPLICATIONS

This application is a continuation of U.S. application Ser. No. 14/753,857 filed Jun. 29, 2015, now U.S. Pat. No. 9,192, 391, which is a continuation of U.S. application Ser. No. 13/169,728 filed Jun. 27, 2011, now U.S. Pat. No. 9,066,804, which is a continuation of U.S. application Ser. No. 10/977, 365 filed Oct. 29, 2004, now U.S. Pat. No. 7,967,822, which in turn is a continuation of U.S. application Ser. No. 10/756, 817 filed Jan. 13, 2004 now U.S. Pat. No. 7,344,541, which is a continuation of U.S. application Ser. No. 09/799,325 filed Mar. 5, 2001, now U.S. Pat. No. 6,695,848. The entire disclosures of each of the above-listed related applications are expressly incorporated herein by reference. Also incorporated by reference herein are U.S. application Ser. No. 09/261,528, filed Mar. 3, 1999, now U.S. Pat. No. 6,197,064, which was a continuation of U.S. application Ser. No. 08/892, 286, filed Jul. 14, 1997, now U.S. Pat. No. 5,879,354, which was a divisional of U.S. application Ser. No. 08/649,465, filed May 17, 1996, now U.S. Pat. No. 5,755,803, which was a continuation-in-part application of U.S. application Ser. No. 08/603,582, filed Feb. 20, 1996, now U.S. Pat. No. 5,810,827, which was a continuation-in-part of U.S. application Ser. No. 08/300,379, filed Sep. 2, 1994, now U.S. Pat. No. 5,514,139 and which was also a continuation-in-part application of U.S. application Ser. No. 08/479,363 filed Jun. 7, 1995, now U.S. Pat. No. 5,643,272, which is a continuation-in-part of U.S. application Ser. No. 08/342,143, filed Nov. 18, 1994, now U.S. Pat. No. 5,597,379, which is a continuation-in-part application of U.S. application Ser. No. 08/300,379, filed Sep. 2, 1994, now U.S. Pat. No. 5,514,139.

BACKGROUND OF THE INVENTION

1. Field of the Invention

This invention generally relates to methods and apparatus for orthopedic surgical navigation and alignment techniques and instruments.

2. Related Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, a series of planar and/or curvilinear surfaces, or "resections," are created to allow for the attachment of prosthetic or other devices to the femur, tibia, and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating sawblade based resection systems has been the standard in total knee replacement for over 30 years. Due to their use of this sub-optimal cutting tool, the instrumentation systems all possess certain limitations and liabilities.

Perhaps the most critical factor in the clinical success of TKA is the accuracy of the implant's placement. This can be described by the degrees of freedom associated with each implant; for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of ⅛ or 3/16 inch diameter pin or drill placement in the anterior or distal faces of the femur for placement of cutting guides. In the case of posterior referencing systems, the distal resection cutting guide is positioned by drilling two long drill bits into the anterior cortex. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking," inherent in the use of multiple alignment guides and cutting guides. Another error inherent in these systems further adding to mal-alignment is deflection of the oscillating sawblade during the cutting process. The use of an oscillating sawblade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA for more than 30 years, orthopedic salespeople still report incidences where poor cuts result in significant gaps in the fit between the implant and the bone.

It is an often repeated rule of thumb for orthopedic surgeons that a "Well placed, but poorly designed implant will perform well clinically, while a poorly placed, well designed implant will perform poorly clinically." One of the primary goals of the invention described herein is to eliminate errors of this kind to create more reproducible, consistently excellent clinical results in a manner that requires minimal manual skill on the part of the surgeon.

None of the previous efforts of others disclose all of the benefits and advantages of the present invention, nor do the previous efforts of others teach or suggest all the elements of the present invention.

OBJECTS AND SUMMARY OF THE INVENTION

Many of the specific applications of the method and apparatus of the present invention described herein apply to total knee replacement, a surgical procedure wherein planar surfaces and/or curvilinear surfaces must be created in or on bone to allow for proper attachment or implantation of prosthetic devices. However, it should be noted that it is within the scope of the present invention to apply the methods and apparatus herein described to the removal of any kind of material from bones in any other application where it is necessary, desirable, or useful to remove material from bones.

The apparatus of the present invention comprises a number of components including a positioning apparatus, a pattern apparatus, and a cutting apparatus.

The pattern apparatus is oriented and located by the use of the positioning apparatus which references the geometry of a bone to be resected and/or other anatomic landmarks. When used to resect a distal femur, the positioning apparatus also references the long axis of the femur. Once the positioning apparatus has been properly located, aligned, and initially fixed in place, the pattern apparatus may be attached thereto, and then adjusted according to the preferences of the surgeon utilizing the apparatus, and then the pattern apparatus can be rigidly fixed to a bone to be resected. This ensures the pattern apparatus is properly located and oriented prior to the use of the cutting apparatus to remove material from the bone.

More specifically, when the method and apparatus of the present invention are used in connection with resecting a distal femur, the positioning apparatus is located and aligned utilizing the intramedullary canal of the femur, (thereby approximating the long axis of the femur), the distal surfaces of the femoral condyles, the anterior surface of the distal femur, and the posterior surfaces of the femoral condyles, which are referenced to indicate the appropriate location and orientation of the pattern apparatus. Fixation means may be used to fix the positioning apparatus, as well as the pattern apparatus to the distal femur. Means may be present in the positioning apparatus and/or pattern device for allowing the following additional adjustments in the location and orientation of the pattern device:
1. internal and external rotational adjustment;
2. varus and valgus angular adjustment;
3. anterior and posterior location adjustments;
4. proximal and distal location adjustment; and
5. flexion and extension angular adjustment.

Cannulated screws, fixation nails or other fixation means may then be used to firmly fix the pattern apparatus to the distal femur. The positioning apparatus may then be disconnected from the pattern apparatus and removed from the distal femur. Thus, the location and orientation of the pattern apparatus is established.

The pattern device possesses slot-like features, or a cutting path, having geometry that matches or relates to the desired geometry of the cut. When used in connection with resecting a knee, the cutting path resembles the interior profile of the distal femoral prosthesis. The cutting path guides the cutting apparatus to precisely and accurately remove material from the distal femur. Thus, the distal femur is thereby properly prepared to accept a properly aligned and located distal prosthesis.

In preparing a patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

The apparatus of the present invention comprises a number of components including an ankle clamp, an alignment rod, a fixation head, cutting guide clamps having an integral attachment mechanism, and a milling bit.

The method of present invention includes the steps of attaching the ankle clamp about the ankle, interconnecting the distal end of the alignment rod with the ankle clamp, interconnecting the fixation head with the proximal end of the alignment rod, partially attaching the fixation head to the proximal tibia, aligning the alignment rod, completely attaching the fixation head to the proximal tibia, interconnecting the cutting guide clamps with the alignment rod, positioning the cutting guide clamps about the proximal tibia, securing the cutting guide clamps to the tibia at a proper location, removing the fixation head, and cutting the proximal tibia with the milling bit.

The implant of the present invention has an outer bearing surface and an inner attachment surface. The outer bearing surface functions as a joint contact surface for the reconstructed bone. The inner attachment surface contacts a bone and is attached thereto. The inner attachment surface of the implant is curvilinear from an anterior to a posterior area of the femur, as is conventionally known, and is also curvilinear from a medial to a lateral area of the femur to approximate the shape of natural femur. The resection of the femur for accommodating the implant can be properly performed by a milling device employing one or more curvilinear milling bits.

There are numerous advantages associated with the curvilinear implant of the present invention. First, it will allow for a very thin implant cross-section and therefore necessitate the removal of the least amount of viable osseous tissue. Accordingly, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs.

This curvilinear implant of the present invention could also result in a less expensive femoral implant because of the reduced amount of material needed for the implant, as well as an improved, more natural, and even stronger knee replacement. The cross-section of the implant could be varied to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces.

The resected surfaces of a femur or other bone to accept the implant of the present invention could be prepared by the apparatus and method for resection shown and described in the prior related applications set forth herein, the entire disclosures of which are expressly incorporated herein by reference.

The apparatus of the present invention comprises a number of components including a positioning and drill guide, a cutting guide and a cutting apparatus. The drill guide is used to create holes in the medial and lateral sides of the femur that correspond to the fixation features of the cutting guide. The cutting guide is oriented and located by inserting fixation nubs connected to the cutting guide into the medial and lateral holes in the femur. The cutting guide can then be further affixed to the femur. The cutting apparatus can then be used with the cutting guide to resect the femur. A conventional cutting block used with a conventional oscillating saw can also be positioned and interconnected with a femur in a similar manner using the drill guide of the present invention to create medial and lateral holes. A cutting guide can then be attached to the holes. A conventional cutting block can be interconnected with the cutting guide for attachment of the block to the femur. This invention can also be used in connection with a cortical milling system, i.e., a cutting system for providing a curvilinear cutting path and curvilinear cutting profile. Likewise, a tibial cutting guide can similarly be positioned on a tibia with a drill guide.

It is a primary object of the present invention to provide an apparatus for properly resecting the distal human femur.

It is also an object of this invention to provide an apparatus for properly orienting a resection of the distal human femur.

It is an additional object of the resection apparatus of the present invention to properly locate the resection apparatus with respect to the distal human femur.

It is even another object of the resection apparatus of the present invention to properly orient the resection apparatus with respect to the distal human femur.

It is another object of the resection apparatus of the present invention to provide a guide device for establishing the location and orientation of the resection apparatus with respect to the distal human femur.

It is still a further object of the resection apparatus of the present invention to lessen the chances of fatty embolisms.

It is even a further object of this invention is to provide a resection apparatus capable of forming some or all of the resected surfaces of the distal human femur.

It is another object of the resection apparatus of the present invention to provide an apparatus which is simple in design and precise and accurate in operation.

It is also an intention of the resection apparatus of the present invention to provide a guide device for determining the location of the long axis of the femur while lessening the chances of fatty embolism.

It is also an object of the resection apparatus of the present invention to provide a device to physically remove material from the distal femur in a pattern dictated by the pattern device.

It is even another object of the resection apparatus of the present invention to provide a circular cutting blade for removing bone from the distal human femur to resection the distal human femur.

It is also an object of the present invention to provide a method for easily and accurately resecting a distal human femur.

These objects and others are met by the resection method and apparatus of the present invention.

It is a primary object of the present invention to provide methods and apparatus for femoral and tibial resection.

It is another object of the present invention to provide a method and apparatus for properly, accurately, and quickly resecting a bone.

It is also an object of this invention to provide a method and apparatus for properly orienting and locating a resection of a bone.

It is a further object of the present invention to provide a method and apparatus to properly locate and orient the resection apparatus with respect to a bone.

It is another object of the present invention to provide methods and apparatus for femoral and tibial resection which are simple in design and precise and accurate in operation.

It is an additional object of the present invention to provide a method and apparatus to physically remove material from a bone in a pattern dictated by a pattern device and/or the geometry of a cutting device.

It is a further object of the present invention to provide methods and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is a further object of the present invention to provide methods and apparatus for femoral and tibial resection wherein the apparatus can be located on a bone to be cut in a quick, safe, and accurate manner.

It is a primary object of the present invention to provide a method and apparatus for properly resecting the proximal human tibia in connection with knee replacement surgery.

It is also an object of the present invention to provide a method and apparatus for resecting the proximal human tibia which minimizes the skill necessary to complete the procedure.

It is another object of the present invention to provide a method and apparatus for resecting the proximal human tibia which properly orients the resection of the proximal tibia.

It is even another object of the present invention to provide a method and apparatus for resecting the proximal human tibia which is easy to use.

It is yet another object of the present invention to provide a method and apparatus for resecting the proximal human tibia which orients the resection in accordance with what is desired in the art.

It is still yet another object of the present invention to provide a method and apparatus for resecting the proximal human tibia which minimizes the amount of bone cut.

It is a further object of the present invention to provide a method and apparatus for resecting the proximal human tibia which allows one to visually inspect the location of the cut prior to making the cut.

It is even a further object of the present invention to provide a method and apparatus for resecting the proximal human tibia which is simple in design and precise and accurate in operation.

It is yet a further object of the present invention to provide a method and apparatus for resecting the proximal human tibia which physically removes material from the proximal tibia along a surface dictated by a guide device.

It is still a further object of the present invention to provide a method and apparatus for resecting the proximal human tibia which employs a milling bit for removing material from the proximal tibia.

It is also an object of the present invention to provide a method and apparatus for resecting the proximal human tibia which includes a component which is operated, and looks and functions, like pliers or clamps.

It is even another object of the present invention to provide an alternate embodiment of the method and apparatus for resecting the proximal human tibia which includes a component that resembles a U-shaped device for placing about the tibia.

It is even a further object of the present invention to provide an alternate embodiment of the method and apparatus for resecting the proximal human tibia which includes a component that resembles an adjustable, square, U-shaped device for placing about the tibia.

These objects and others are met and accomplished by the method and apparatus of the present invention for resecting the proximal tibia.

It is a primary object of the present invention to provide a method and apparatus for removing material from bones.

It is another object of the present invention to provide a method and apparatus for properly resecting bone.

It is also an object of this invention to provide a method and apparatus for properly orienting a resection of a bone.

It is a further object of the present invention to provide a method and apparatus to properly orient the resection apparatus with respect to a bone.

It is an additional object of the present invention to provide a method and apparatus for properly locating a bone resection.

It is a further object of the present invention to provide a method and apparatus to properly locate the resection apparatus with respect to a bone.

It is even another object of the resection apparatus of the present invention to provide a guide device and method of use thereof for establishing the location and orientation of the resection apparatus with respect to a bone.

It is an additional object of the present invention to provide a method and apparatus for making a curvilinear bone resection.

It is still a further object of the resection apparatus of the present invention to lessen the chances of fatty embolisms.

It is even further object of this invention to provide a method and apparatus capable of forming or re-forming some or all of the surfaces or resected surfaces of a bone.

It is another object of the present invention to provide a method and apparatus which is simple in design and precise and accurate in operation.

It is also an intention of the present invention to provide a method and apparatus for determining the location of the long axis of a bone while lessening the chances of fatty embolisms.

It is also an object of the present invention to provide a method and apparatus to physically remove material from a bone in a pattern.

It is an additional object of the present invention to provide a method and apparatus to physically remove material from a bone in a pattern dictated by a pattern device and/or the geometry of a cutting device.

It is even another object of the resection apparatus of the present invention to provide a cylindrical or semi-cylindrical cutting device and method of use thereof for removing material from a bone.

It is also an object of the present invention to provide a method and apparatus for easily and accurately resecting a bone.

It is also an object of the present invention to provide a method and apparatus for resecting a bone which minimizes the manual skill necessary to complete the procedure.

It is even another object of the present invention to provide a method and apparatus for resecting a bone which is easy to use.

It is still yet another object of the present invention to provide a method and apparatus for resecting a bone which minimizes the amount of bone removed.

It is a further object of the present invention to provide a method and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is even another object of the present invention to provide a method and apparatus for removing material from a bone such that both the cutting path and cutting profile are predominantly curvilinear.

It is a primary object of the present invention to provide an apparatus to properly replace damaged bony tissues.

It is also an object of this invention to provide an apparatus to properly replace damaged bony tissues in joint replacement surgery.

It is also an object of the present invention to provide an implant for the attachment to a distal femur in the context of knee replacement surgery.

It is an additional object of the present invention to provide a method and apparatus for making a curvilinear implant.

It is another object of the present invention to provide an implant having a reduced thickness to reduce the amount of material required to make the implant.

It is even another object of the present invention to provide an implant having curvilinear fixation surfaces for increasing the strength of the implant.

It is another object of the present invention to provide an implant having a fixation surface that is anterior-posterior curvilinear and mediolateral curvilinear.

It is another object of the present invention to provide an implant that has a fixation surface that is shaped to resemble a natural distal femur.

It is also an object of the present invention to provide an implant apparatus for allowing proper patellofemoral articulation.

It is a further object of the present invention to provide for minimal stress shielding of living bone through reduction of flexural rigidity.

It is an additional object of the present invention to provide an implant apparatus having internal fixation surfaces which allow for minimal bony material removal.

It is another object of the present invention to provide an implant apparatus with internal fixation surfaces that minimize stress risers.

It is another object of the present invention to provide an implant apparatus having internal fixation surfaces for precise fixation to curvilinear body resections.

It is another object of the present invention to provide an implant apparatus having internal fixation surfaces for precise apposition to curvilinear body resections.

It is another object of the present invention to provide an implant apparatus having internal fixation surfaces for curvilinear interior fixation geometries closely resembling the geometry of the external or articular geometry of the implant apparatus.

It is also an object of this invention to provide a method and apparatus for properly locating and orienting a prosthetic implant with respect to a bone.

It is another object of the present invention to provide an implant which is simple in design and precise and accurate in operation.

It is also an object of the present invention to provide an implant which minimizes the manual skill necessary to complete the procedure.

It is still yet another object of the present invention to provide an implant which minimizes the amount of bone removed.

It is even another object of the present invention to provide a method and apparatus for removing material from a bone such that both the cutting path and cutting profile are predominantly curvilinear.

BRIEF DESCRIPTION OF THE DRAWINGS

Other important objects and features of the invention will be apparent from the following detailed description of the invention taken in connection with the accompanying drawings in which:

FIG. 10 is a partially exploded side plan view of another embodiment of the tibial resection apparatus shown in FIG. 8, wherein the cutting guide clamps interconnect with the alignment rod by means of a cutting guide clamp linkage.

FIG. 11 is a side plan view of an embodiment of the cutting guide clamps shown in FIG. 8, wherein the cutting guide clamps are adjustable.

FIG. 12 is a top plan view of the cutting guide clamps shown in FIG. 11.

FIG. 17 is a top plan view of another alternate embodiment of a square U-shaped cutting guide for use in the present invention.

FIG. 27 is an exploded perspective view of the protractor rod guide assembly portion of the positioning apparatus shown in FIG. 24.

FIG. 40 is a side plan view of another embodiment of the pattern apparatus and positioning apparatus of the present invention for resecting a patella.

FIG. 41 is a top plan view of the patella resection apparatus shown in FIG. 40.

FIG. 42 is a front plan view of the patella resection apparatus shown in FIG. 40.

FIG. 46 is a partially exploded perspective view of the interconnection of a handle with milling bit for use in connection with pattern plate shown in FIG. 45.

FIG. 49 is a side plan view of the curvilinear milling bit and resection guide shown in FIG. 35.

FIG. 60 is a partially exploded perspective view of the apparatus shown in FIG. 57.

FIG. 61A is a perspective view of an embodiment of a femoral resection apparatus having cutting guides, and FIG. 61B is a side view thereof.

FIG. 65B is a side view thereof.

FIG. 66A is a perspective view of the positioning and drill guide apparatus of the present invention, along with a femur to be resected having a intramedullary rod inserted therein, and FIG. 66B is a side view thereof.

FIG. 68 is a front view of a cutting guide of the present invention positioned for attachment to a femur to be resected.

DETAILED DESCRIPTION OF THE PREFERRED EMBODIMENTS

As shown generally in FIGS. 1-6, the resecting apparatus of the present invention comprises a number of components, namely positioning apparatus generally indicated at 10 comprising positioning body generally indicated at 12, angular adjustment block generally indicated at 32, rotational alignment device generally indicated at 50, pattern device generally indicated at 59 and cutting means generally indicated at 90.

Figure 1:
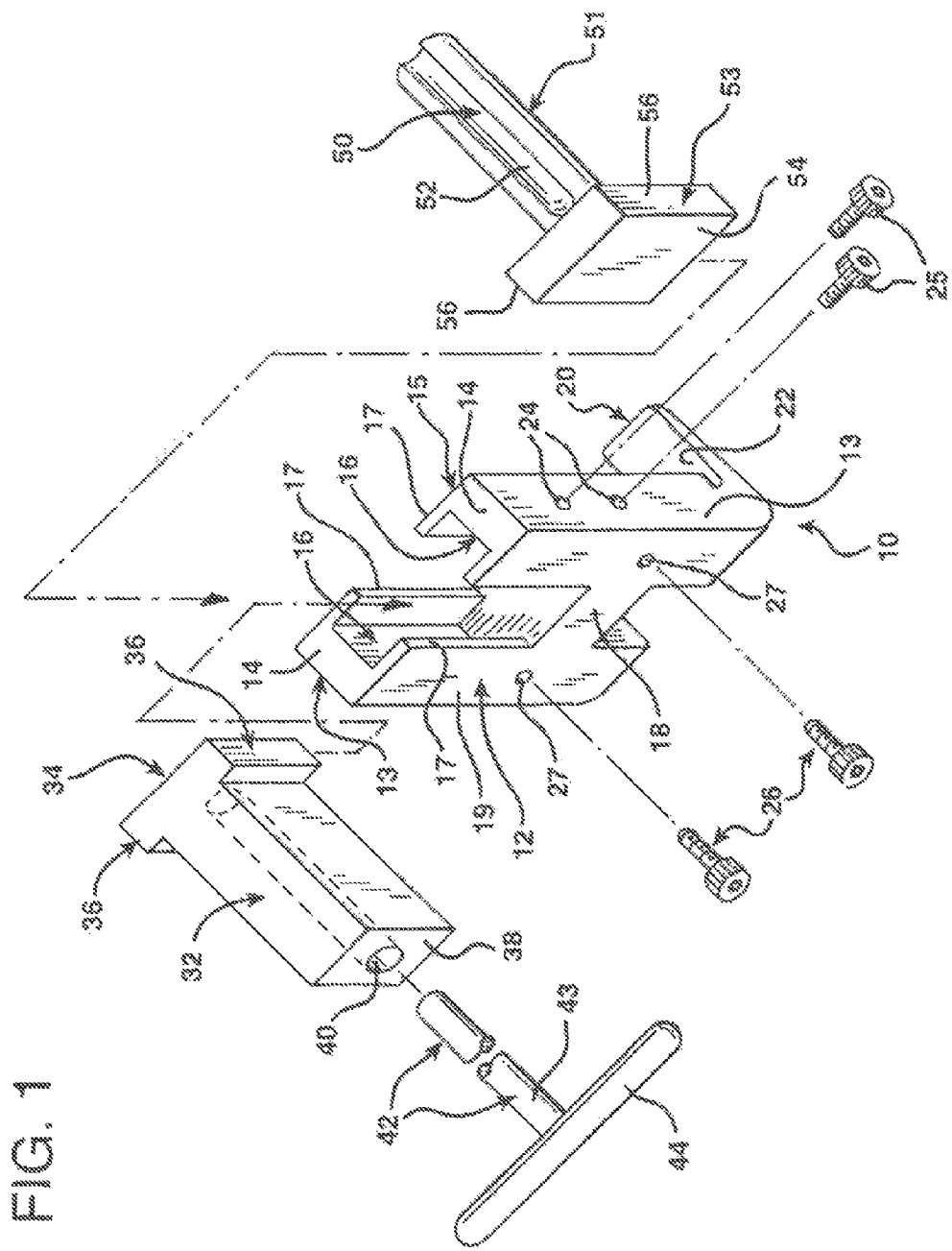
FIG. 1. is an exploded view of the resection apparatus of the present invention showing the positioning apparatus body, the angular adjustment component and the rotational alignment component.

As shown in detail in FIG. 1, the positioning apparatus, generally indicated at 10, includes a positioning body generally indicated at 12 having sides 13, top surface 14, front surface 15, back surface 19 and cross member 18. Extending from a lower end of the positioning body 12 is positioning tongue 20 having an upper surface 22. Extending into the positioning body 12 from top surface 14 to the cross member 18 and through the front and back surfaces 15 and 19, is a gap generally defined by slots 16 and partial slot walls 17. Sides 13 include apertures 24 for receiving locking screws 25. Also extending through the body 12 from the back surface 19 to the front surface 15 are apertures 27 for receiving fixation screws 26.

The positioning apparatus 10 receives and holds angular adjustment block generally indicated at 32. Angular adjustment block 32 includes a front surface 34 having wings 36 sized to be received by the slots 16 in the positioning body 12 to hold the angular adjustment block 32. The angular adjustment block 32 is locked into place in the positioning body 12 by means of locking screws 25, which extend through apertures 24 in the positioning body 12 and contact the wings 36 of the angular adjustment block 32 to secure the angular adjustment block 32 to the positioning body 12. The angular adjustment block 32 establishes the angular alignment and anterior/posterior location of the positioning apparatus 10.

The angular adjustment block 32 also includes back surface 38 and an aperture 40 extending from the back surface 38 through the angular adjustment block 32 to the front surface 34. The aperture 40 receives an intermedullary rod 42 therethrough. The intermedullary rod 42 comprises a shaft 43 and a handle 44. The shaft 43 extends through the angular adjustment block 32 and into the intermedullary canal which extends along the axis of the femur to aid in establishing the orientation of the resection apparatus of the present invention as hereinafter described.

The rotational alignment device, generally indicated at 50, includes a shaft 51 having a groove 52 therealong and a block 53 having a back surface 54 and wings 56. The rotational alignment device 50 is interconnected with the positioning body 12 by means of the wings 56 received in slots 16 of the positioning body 12. The rotational alignment device 50 may be secured to the positioning body 12 by means of locking screws 25 which extend through apertures 24 in the positioning body 12 to contact the wings 56. The locking screws 25 may be made of various configurations depending upon their specific function. Importantly, the locking screws 25 are used to rigidly affix one component or device to another to ensure that the relative locations and orientations are maintained despite the rigors of surgery.

Figure 2:
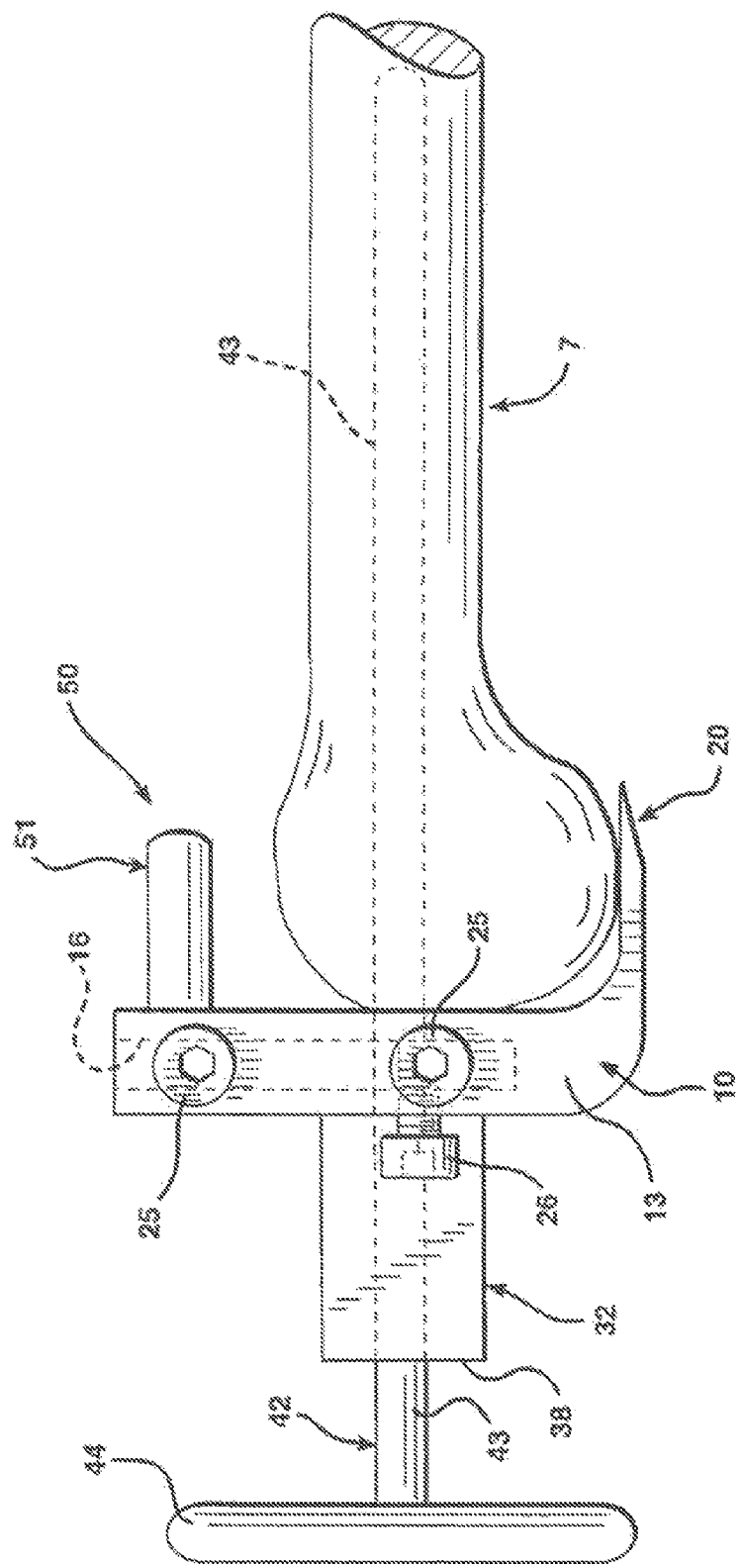
FIG. 2 is a side plan view of the guide device of the resection apparatus of FIG. 1 attached to a distal human femur.
Figure 7:
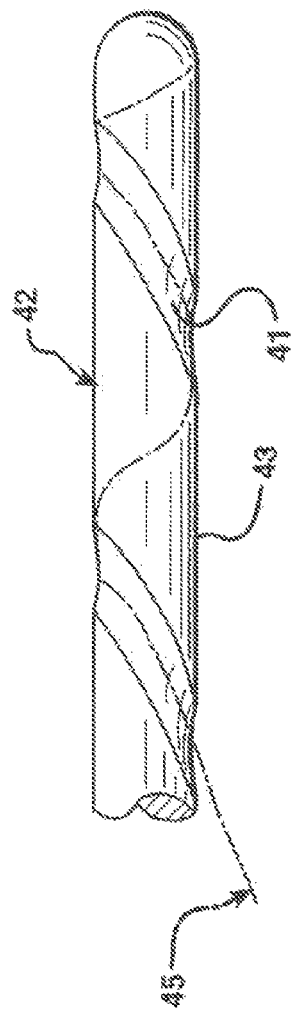
FIG. 7 is a side plan view of an intermedullary rod having a helical groove for use with the resection apparatus shown in FIG. 1.

As shown in FIG. 2, wherein the positioning body 12 is fitted with the angular adjustment block 32 and the rotational alignment device 50, the entire positioning apparatus 10 is connected to a human femur 7 by means of the shaft 43 of the intermedullary rod 42. The shaft 43 extends through the angular adjustment block 32, and thereby through the positioning body 12 into the intermedullary canal which extends along the axis of the femur 7. The intermedullary rod 42, shown in FIG. 7, has a groove 41 transversing a helical path 45 along the axis of the shaft 43. The groove 41 relieves intermedullary pressure that leads to fatty embolisms. The basic concept of the intermedullary rod 42 with the groove 41, is that as it is inserted into the femur, which contains liquid fatty tissue, the liquid fatty tissue is drawn up the groove 41 of the intermedullary rod 42 to draw the fatty liquid tissue out of the femur. Preferably, the intermedullary rod would have a hexagonal head, (not shown) to permit it to be driven by a powered device such as an electrical hand held tool. Importantly, the groove 41 does not have a cutting edge, which would risk perforation of the femoral cortex. Accordingly, the device does not cut solid material, but removes liquid material from the intermedullary canal. Therefore, the risk of fatty embolism is reduced.

After positioning body 12 is properly located against the femur 7 by means of the intermedullary rod 42 and the angular adjustment block 32, fixation screws 26 may be advanced through the apertures 27 in the positioning body 12 until they make contact with the distal femoral condyles of the femur 7, and are then driven into the distal femoral condyles of the femur 7 to initially affix the positioning apparatus to the distal femur 7. It should be noted that the fixation screws 26 may also be advanced and adjusted to make up for deficiencies in the distal femoral condyles. Accordingly, the positioning body 12 is positioned such that the front surface 15 is put into contact with the distal femoral condyles by direct contact, and the tongue 20 is positioned under the femur 7 and in contact therewith.

As can be seen in FIG. 2, the shaft 51 of the rotational alignment device 50 extends above the femur 7 and allows for rotation of the pattern device 59, hereinafter described, about the distal femur 7. Additionally, the rotational alignment device 50 allows for the anterior/posterior positioning of the pattern device 59 with respect to the femur 7. Importantly, the configurations of the positioning body 12, the angular adjustment block 32, and the rotational alignment device 50 are not limited to the structure set forth herein, but may be of different shapes and may interconnect in different ways. These components may even be formed as a unitary or partially unitary device.

Figure 3:
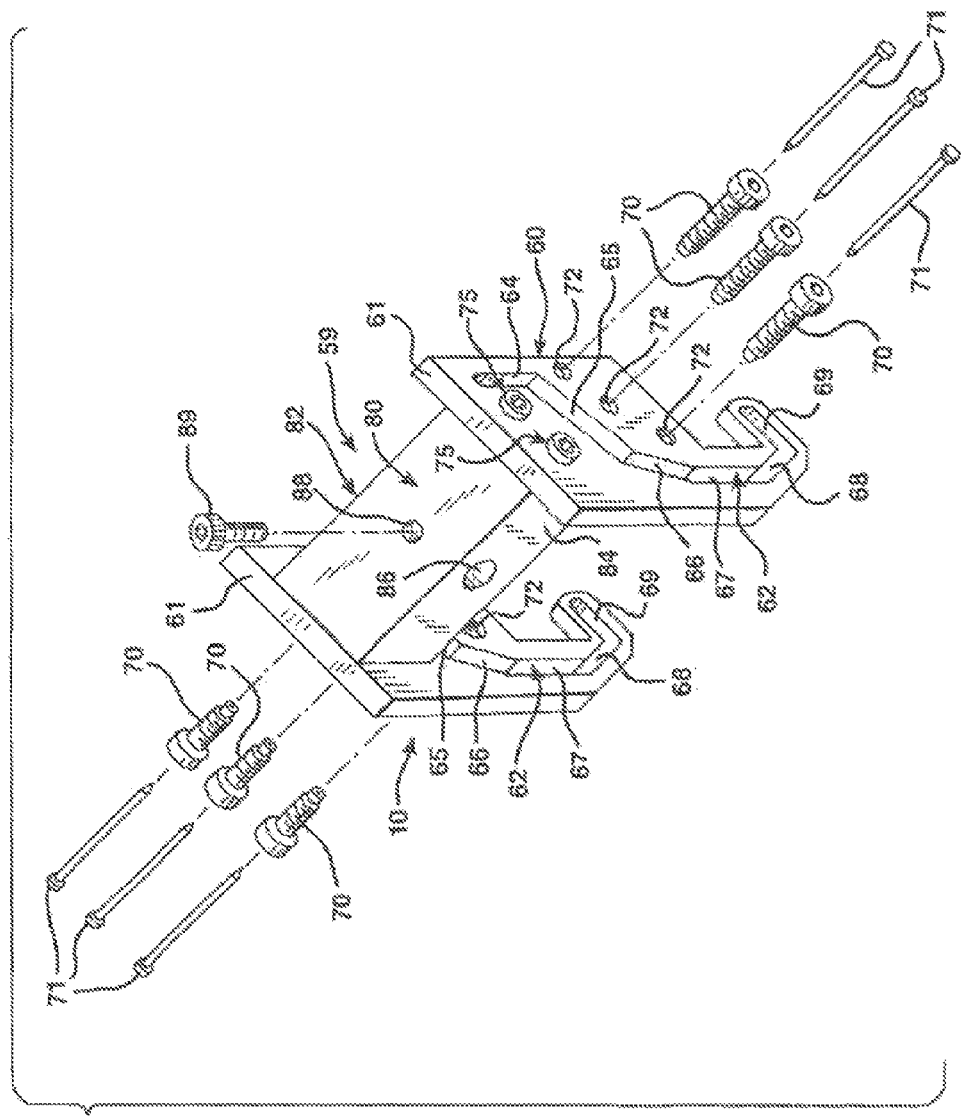
FIG. 3 is an exploded view of the pattern device of the resection apparatus of the present invention.

As shown in FIG. 3, the pattern device 59 includes pattern plates 60 having tops 61, and cutting paths, generally indicated at 62, extending therethrough. The cutting paths 62 outline the desired resection shape of the distal femur 7. Generally, the cutting paths 62 could include a first vertical path 64, extending to a first diagonal path 65, extending to a second diagonal path 66, extending to a second vertical path 67, extending to a third diagonal path 68, and then extending to a horizontal path 69. Alternatively, the cutting paths 62 could describe any desired resection shape for the femur 7. The pattern plates 60 also include locking screws 75 for interconnecting the pattern plates 60 with a crossbar 80.

The pattern device 59 of the present invention preferably includes two pattern plates 60 held in a spaced apart relationship by crossbar 80. The crossbar 80 separates the pattern plates 60 sufficiently to permit the pattern plates 60 to extend along the sides of the distal femur 7. The crossbar 80 includes a front surface 82, back surface 84, a top surface 83, a central aperture 86 extending from the front surface 82 to the back surface 84, a lock aperture 88 extending through the top surface 83, and a lock screw 89. The central aperture 86 of the crossbar 80 receives the shaft 51 of the rotational alignment device 50. Accordingly, the pattern device 59 is interconnected with the positioning apparatus 10 so that the pattern device 59 is properly oriented with respect to the femur 7. Upon proper positioning of the crossbar 80, with respect to the shaft 51 of the rotational alignment device 50, lock screw 89 is extended through lock aperture 88 to contact the shaft 51 to lock the crossbar 80 and, accordingly, the pattern device 59, onto the shaft 51 of the rotational alignment device 50, and accordingly, to positioning apparatus 10. This completed assembly is attached to the femur 7, as shown in FIG. 4.

Figure 4:
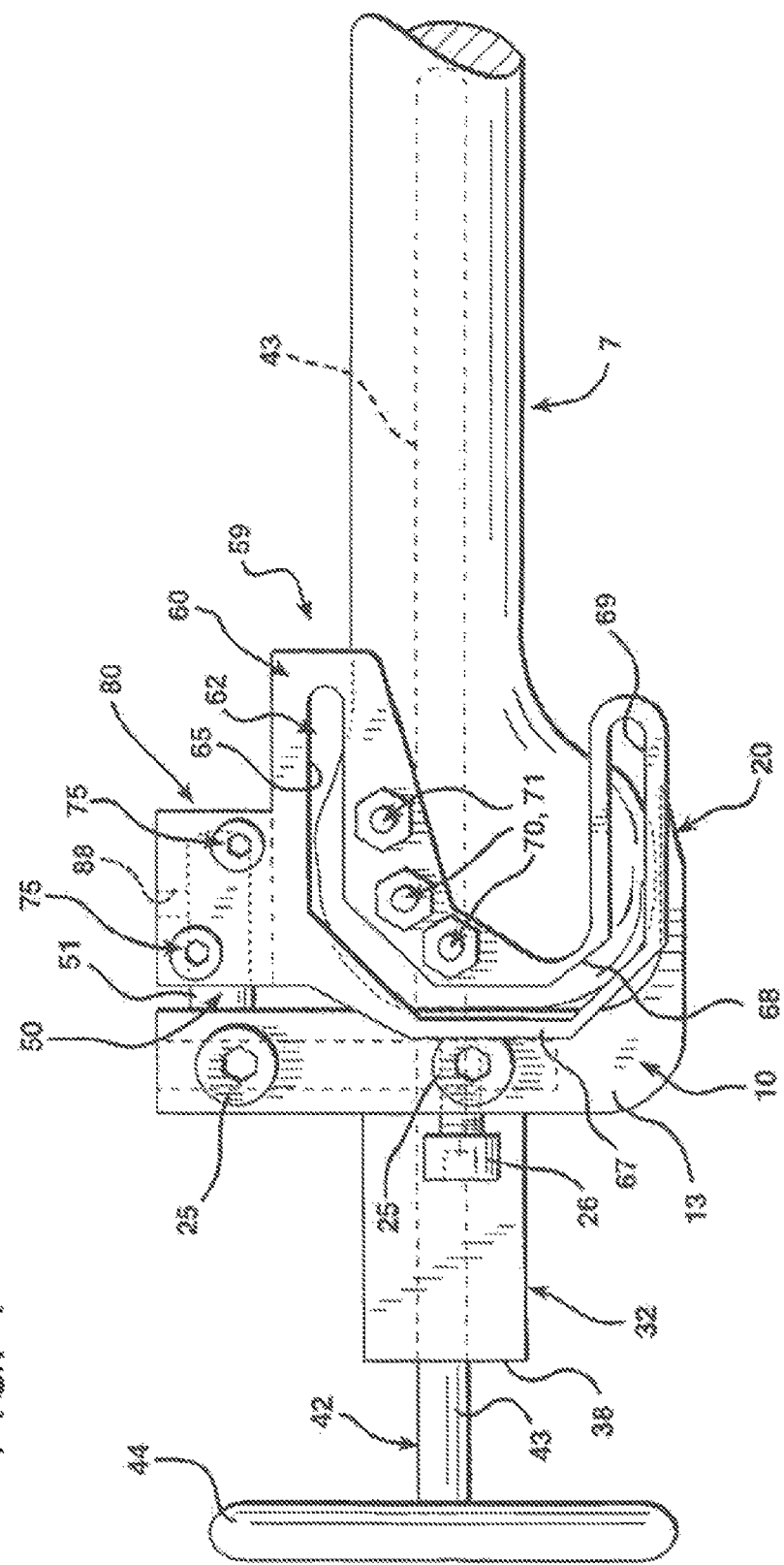
FIG. 4 is a side plan view of the resection apparatus shown in FIG. 2 with the pattern device fixed to the distal human femur.

As additionally shown in FIGS. 3 and 4, the pattern plates 60 include plate apertures 72 for receiving cannulated screws 70 which have apertures extending therethrough for receiving fixation nails 71 therethrough. Accordingly, after the pattern device 59 is interconnected with the positioning apparatus 10, and properly located and oriented with respect to the femur 7, the cannulated screws 70 are extended through the plate aperture 72 to contact the sides of the distal femur 7. Then, in order to fix the pattern plates 60 with respect to the femur 7, the fixation nails 71 are driven into the distal femur 7 to lock the pattern plate 60 into position on the distal femur 7. The cannulated screws 70 have sharp leading edges for allowing decisive purchase in the distal femur 7 before the introduction of the fixation nails 71 to complete fixation of the pattern device 59 to the distal femur 7.

The pattern plates 60 by virtue of the cutting paths 62, dictate the shape of the resection of the femur 7. The cutting paths 62 are essentially channels through the pattern plates 60. The cutting paths 62 receive the cutting device and guide it as it resects the surface of the distal femur 7. The pattern plates 60 straddle the distal femur 7 mediolaterally and are suspended by the crossbar 80. Likewise, crossbar 80 maintains the proper relationship between the pattern plates 60 before and during the resection of the distal femur 7. The location of the crossbar 80 and accordingly, the pattern plates 60, may be adjusted with respect to the positioning apparatus 10 by adjusting the position of the block 53 of the rotational alignment device 50 within the slots 16 of the positioning body 12, and locking the same with locking screws 25.

Figure 5:
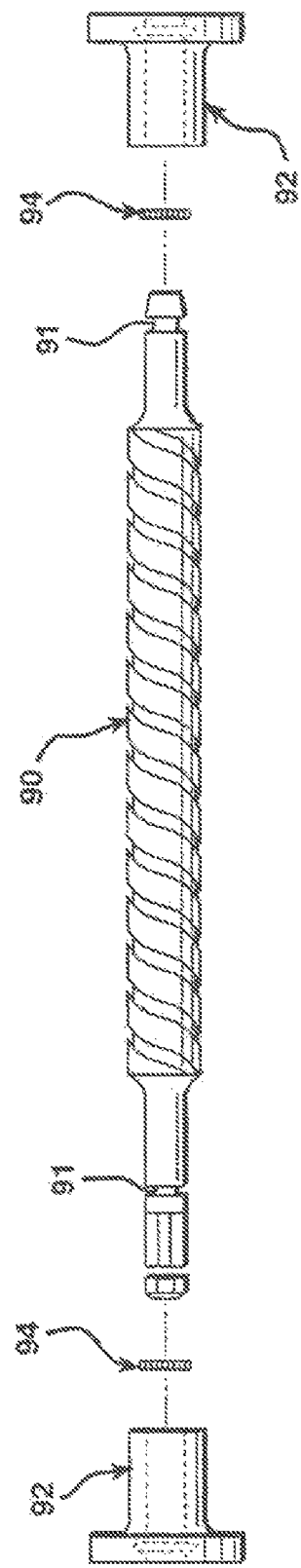
FIG. 5 is an exploded front view of the cutting device of the resection apparatus of the present invention.

The cutting paths 62 in the pattern plates 60 receive and guide the cutting device shown in FIG. 5 and generally indicated at 90. The cutting device 90 performs the actual cutting of the femur 7 to resect the femur 7. The cutting device may be of any known configuration. In a preferred embodiment, the cutting device is a drill. The drill 90 is generally cylindrical in shape and may possess helical cutting teeth along its length to cut the femur 7. The drill 90 includes a hexagonal end 95 to permit the use of an electric powered drive, typically an electric drill. Further, the drill 90 includes drill bushings 92 at the ends of the drill 90 to provide a non-metallic bearing between the cutting paths 62 in the pattern plates 60 to avoid galling and to ensure smooth articulation of the drill 90 along the cutting path 62. Positioned between the drill bushings 92 and the drill 90 are retention springs 94 which are essentially coil springs retained within the drill bushings 92 to allow the drill bushings 92 to be easily attached and removed from the drill 90. These retention springs 94 are commercially available in medical grade stainless steels. The drill bushings 92 retain the retention springs 94 which hold the drill bushings 92 in position 92 on the drill 90 while allowing the drill bushings 92 to rotate freely. The drill 90 may also include circumferential grooves 91 for allowing attachment and retention of the drill bushings 92 by means of the retention springs 94. Importantly, the configuration of the drill 90 can vary in accordance with what is known in the art, as long as the cutting device can follow the cutting paths 62 in the pattern plates 60 to resect the femur 7.

Figure 6:
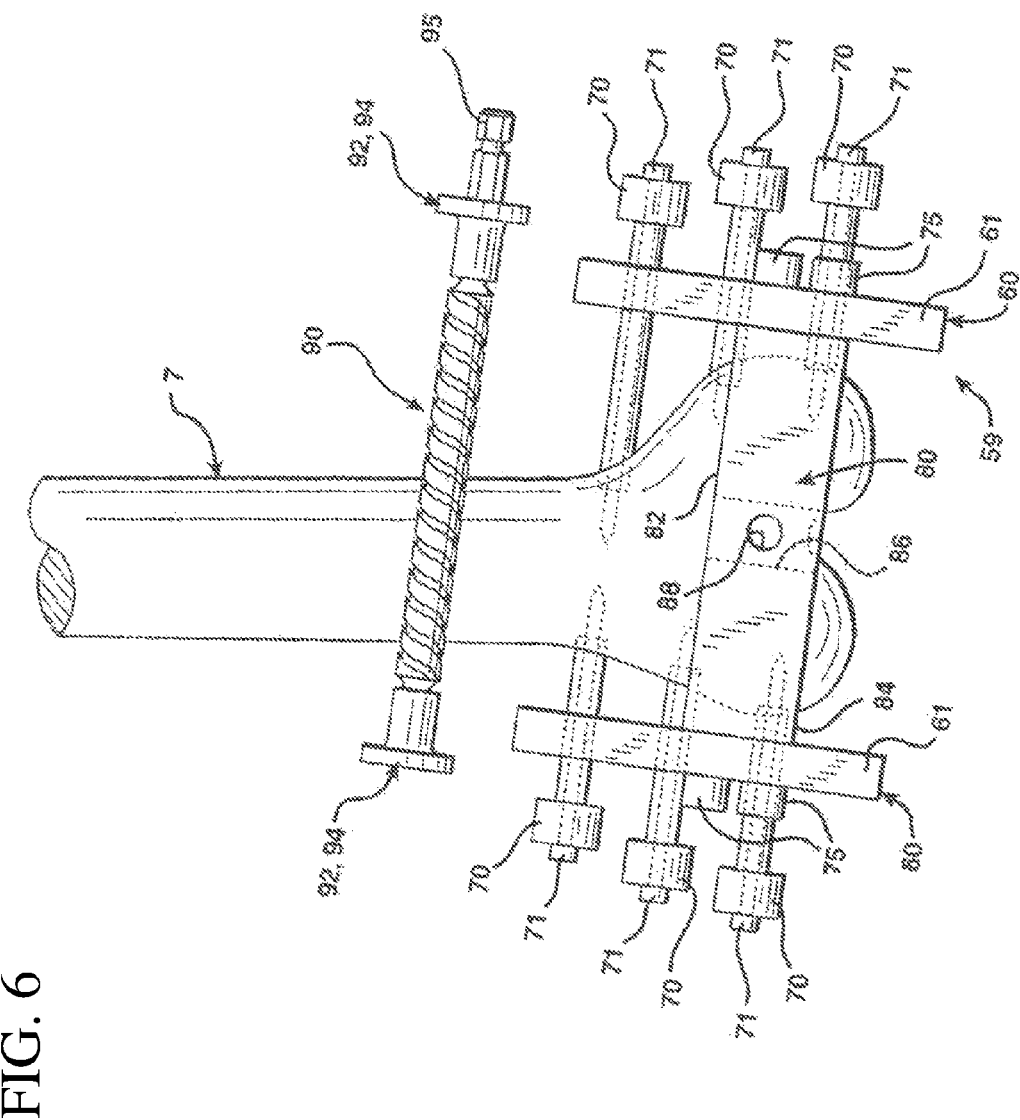
FIG. 6 is a top plan view of the pattern device and the cutting device of the resection apparatus of the present invention affixed to the distal human femur.

As shown in FIG. 6, after the pattern device 59 is attached to the distal femur 7, and positioned accordingly by means of the positioning apparatus 10, and secured to the distal femur 7 by means of cannulated screws 70 and fixation nails 71, positioning apparatus 10 may be removed from connection to the distal femur 7 leaving the pattern device 59 attached to the distal femur 7 to permit resecting of the distal femur. The drill 90 is then positioned within the cutting paths 62 between the pattern plates 60. Next the drill 90 is rotated by power means in connection with the hexagonal end 95, and is then moved along the cutting path 62 to resect the distal femur 7. It should also be noted that the cutting means could be operated by hand.

Instead of two pattern plates 60, a single pattern plate could be employed if it is sufficiently sturdy to support and guide the drill. The pattern plates 60 may also comprise plates having edges in the shape of the desired distal femoral resection pattern. Thus, the cutting device may be drawn along the edges of the pattern plates to resect the distal femur. Further, any cutting device that can be employed to follow the cutting paths in the pattern plates is considered to be within the scope of this invention.

The resection apparatus of the present invention, through proper use as previously described, provides extremely accurate and reproducible bone cuts. While the anterior and distal areas of the femur will almost always be able to be prepared in this manner, interference from soft tissue such as fat and ligaments may prohibit satisfactory preparation of the posterior femur. The preparation of any remaining femoral surfaces may be completed in any manner known in the art after using the instrumentation of the present invention.

Figure 8:
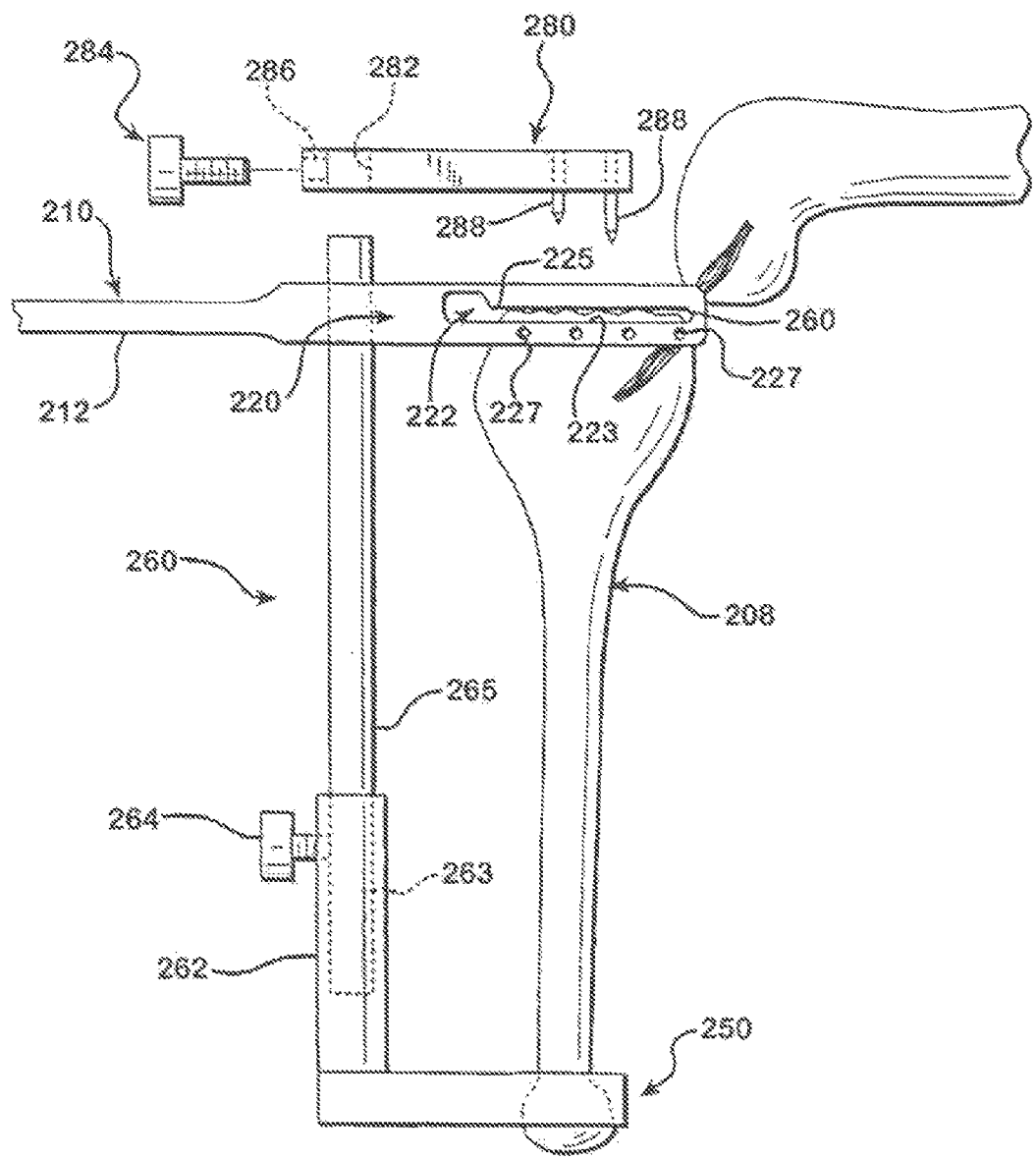
FIG. 8 is a partially exploded side plan view of an embodiment of the tibial resection apparatus of the present invention shown attached to the tibia, wherein the cutting guide clamps are of a fixed size and directly interconnect with the alignment rod.
Figure 9:
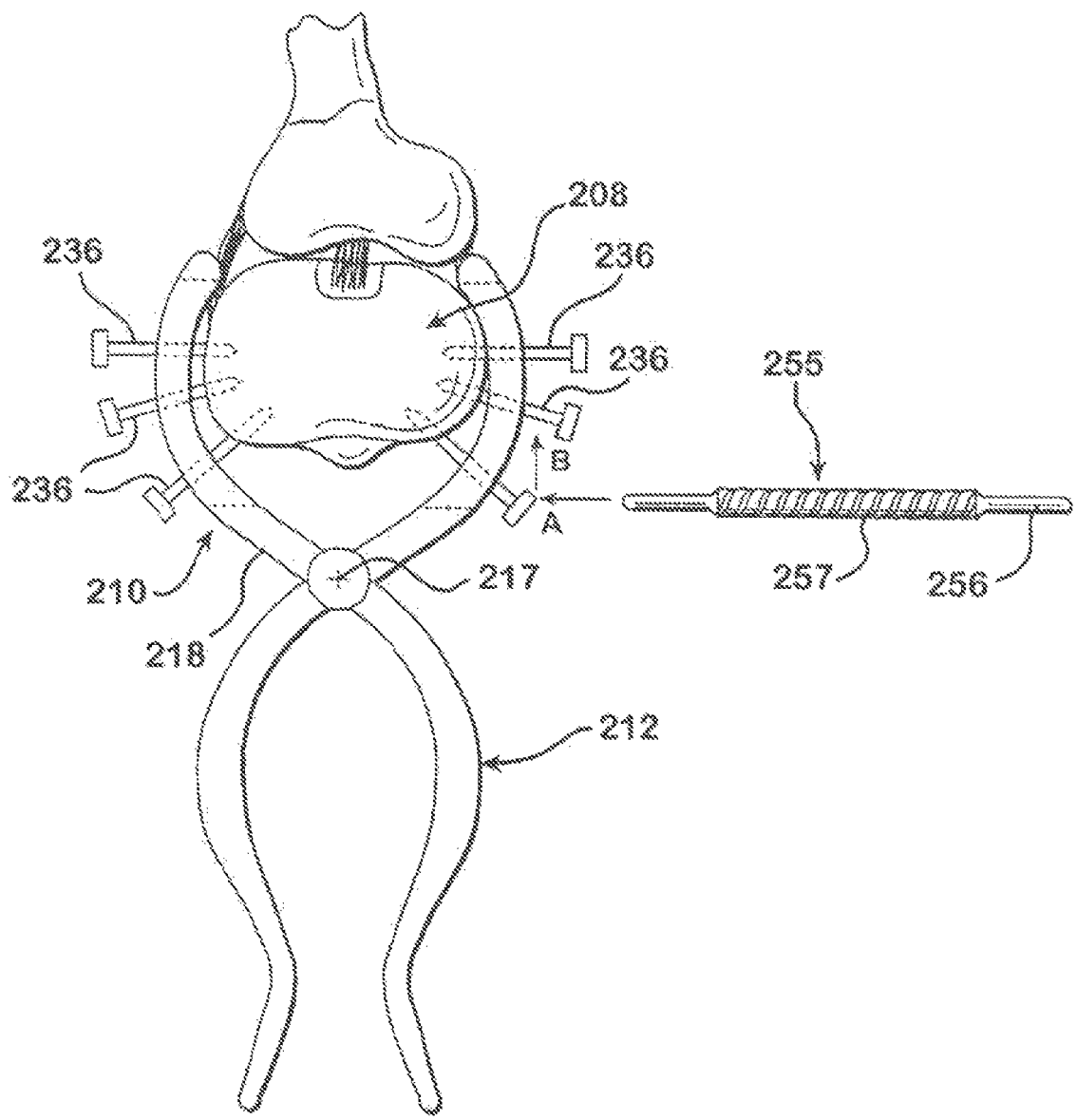
FIG. 9 is a top plan view of the tibial resection apparatus, shown in FIG. 8 prior to insertion of the milling bit into the apparatus.
Figure 13:
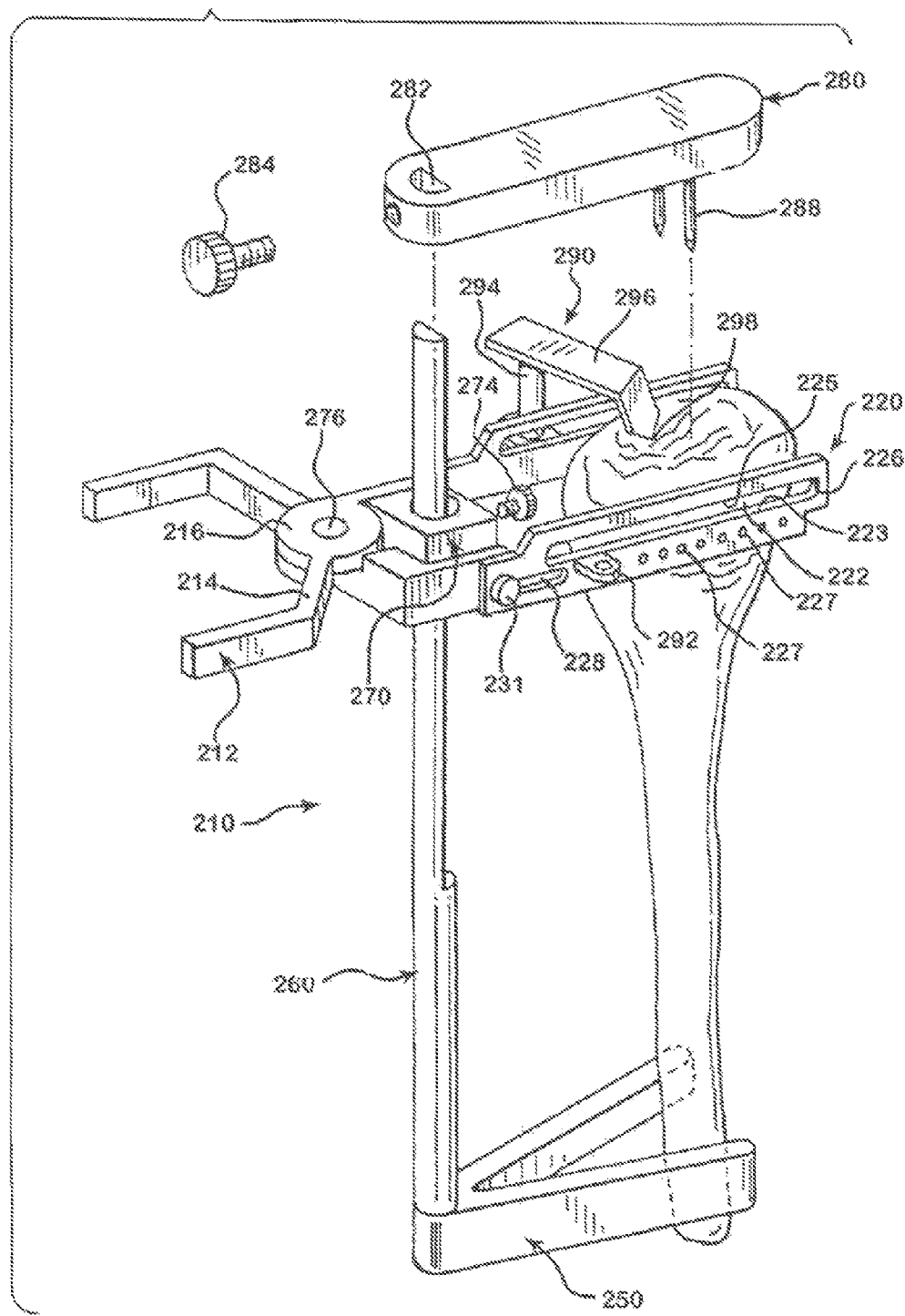
FIG. 13 is a perspective view of an embodiment of the tibial resection apparatus shown in FIG. 8, showing the proximal tibial referencing stylus attached to the cutting guide clamps.

As shown in FIGS. 8-13, the tibial resection apparatus of the present invention includes a number of components, namely, cutting guide clamps generally indicated at 210, cutting guides generally indicated at 220, ankle clamp generally indicated at 250, alignment rod generally indicated at 260, cutting guide clamp linkage generally indicated at 270, fixation block generally indicated at 280, proximal tibial referencing stylus generally indicated at 290, and milling bit generally indicated at 255. It should be noted that the cutting guides 220 may be formed integrally with the cutting guide clamps 210 as shown in FIGS. 8 and 9, or as separate members as shown in FIGS. 11, 12 and 13. Also, the cutting guides 220 may ride the alignment 260 as shown in FIGS. 8 and 9, or they may interconnect with the alignment rod 260 by means of cutting guide clamp linkage 270, as shown in FIGS. 11, 12 and 13.

As shown in FIG. 8, the ankle clamp 250 is attached at or just above the ankle and exterior to the skin. Any conventional ankle clamp may be used to firmly engage the ankle, or to engage the tibia above the ankle, to obtain a reference point for the other components of the present invention.

The ankle clamp is interconnected with and locked into place on the alignment rod 260 in any way known in the art. Preferably, though not necessarily, the alignment rod 260 is vertically adjustable with respect to the ankle clamp 250. This vertical adjustment can be achieved at the ankle clamp 250, at the interconnection of the ankle clamp 250 and the alignment rod 260, or within the alignment rod 260 itself. As shown in FIG. 8, the alignment rod includes a first lower end 262 having an aperture 263 extending vertically therein for telescopically receiving a second upper end 265 of the alignment rod 260. A set screw 264 is provided for fixing the upper end 265 with respect to the lower end 262.

The fixation block 280 is interconnected with an upper end of the alignment rod 260 by means of an aperture 282 in the fixation block 280 sized to receive the alignment rod 260 therethrough, or in any other manner known in the art. A set screw 284 may be provided to extend into the fixation block 280, through set screw aperture 286 in fixation block 280, to contact the alignment rod 260, to lock the fixation block 280 onto the alignment rod 260. The fixation block 280 additionally includes apertures extending vertically therethrough for receiving fixation pins 288 for affixing the fixation block 280 to the proximal tibia 208.

In operation, the ankle clamp 250 is attached about the ankle, or about the tibia just above the ankle, on the exterior of the skin. The fixation block 280 is already interconnected with the alignment rod 260. It is preliminarily positioned over the proximal tibia 208, and one of the fixation pins 288 is driven into the proximal tibia 208. Thereafter, the alignment rod 260 is adjusted to establish proper varus/valgus alignment and flexion/extension angulation as is conventionally known. Upon proper alignment of the alignment rod 260, the other fixation pin 288 is driven into the proximal tibia 208 to completely fix the fixation block 280 to the proximal tibia 208 to lock in the proper alignment of the alignment rod 260. Then, the fixation block 280 may be locked into position on the alignment rod 260.

After properly aligning and locking in the alignment of the alignment rod 260, the cutting guide clamps 210 and the cutting guides 220 may be employed. The cutting guide clamps 210 are interconnected with the alignment rod 260 by means of cutting guide linkage 270. Alternatively, the cutting guide clamps 210 could directly interconnect with the alignment rod 260 through apertures in the cutting guide clamps 210, as shown in FIGS. 8 and 9. As shown in FIG. 10, the cutting guide clamp linkage 270 comprises a body 271 having an alignment rod aperture 272 for receiving and riding the alignment rod 260 and a pivot locking set screw 274 which extends into the cutting guide clamp linkage 270 through set screw aperture 275 for contacting the alignment rod 260 and locking the cutting guide clamp linkage 270 with respect to the alignment rod 260. It should be pointed out that it may be desirable for the alignment rod 260 to have a flattened surface extending longitudinally along the alignment rod 260 for co-acting with set screw 274 for maintaining proper alignment between the cutting guide clamp linkage 270 and the alignment rod 260.

The cutting guide clamp linkage 270 also includes a pivot shaft 276 rigidly interconnected with the body 271 of the cutting guide clamp linkage 270 by member 277 to position the pivot shaft 276 a distance away from the body 271 such that the cutting guide clamps 210 can be interconnected with the pivot shaft 276 and can be properly utilized without interfering with the body 271 of the cutting guide clamp linkage 270.

After the alignment rod 260 is properly aligned and locked into position, the cutting guide clamp linkage 270 is moved into its approximate desired position at the proximal tibia 208. It should be noted that the cutting guide clamp linkage 270 of present invention is positioned on the alignment rod 260 at the beginning of the procedure, prior to aligning the alignment rod 260, and prior to interconnecting the fixation block 280 with the alignment rod 260. However, it is within the scope of the present invention to provide a cutting guide clamp linkage 270 which is attachable to the alignment rod 260 after the alignment rod 260 has been aligned and locked into position.

After the cutting guide clamp linkage 270 is preliminarily approximately located, it is locked into place on the alignment rod 260. Thereafter, the cutting guide clamps 210 may be interconnected with the pivot shaft 276 by means of corresponding pivot apertures 217 in the cutting guide clamps 210.

As shown in FIGS. 11 and 12, the cutting guide clamps 210 include opposing hand grips 212 for grasping and manipulating the cutting guide clamps 210. Crossbar members 214 extend from the hand grips 212 to clamp members 218. The crossbar members 214 cross over each other at cross over point 215 whereat the crossbar members 214 have mating recessed portions 216 which function to maintain the hand grips 212 in the same plane as the clamp members 218. At the cross over point 215, the crossbar members 214 can pivot with respect to each other such that movement of the hand grips 212 towards each other moves the clamp members 218 together, and likewise, movement of the hand grip members 212 away from each other serves to move the clamp members 218 apart in the same manner as scissors or pliers. At the cross over point 215, the crossbar members 214 have corresponding pivot apertures 217 for receiving the pivot shaft 276 of the cutting guide clamp linkage 270. Thus, the cutting guide clamps 210 pivot about the pivot shaft 276 of the cutting guide clamp linkage 270. It should be noted that the crossbar members 214 could be interconnected with each other by a rivet or other means known in the art, or could be entirely independent pieces which co-act as set forth above only upon being seated on pivot shaft 276.

The clamp members 218 of the cutting guide clamps 210 include cutting guide adjustment screw apertures 219 at the far ends thereof for receiving A-P adjustment screws 230 for adjustably interconnecting the cutting guides 220 with the clamp members 218, for adjustable movement in the direction shown by arrow C in FIG. 11. The clamp members 218 may be adjustably interconnected with the cutting guides 220 in any way known in the art. In one embodiment, the cutting guide adjustment screw apertures 218 are threaded and the cutting guides 220 have corresponding elongated apertures 228 extending over a portion of the length thereof for receiving the A-P adjustment screws at a desired location thereaalong. The A-P adjustment screws include a head 231, a retaining head 232, and a threaded shaft 234. When the cutting guides 220 are positioned correctly with respect to the clamp members 218, the A-P adjustment screws 230 are tightened down to lock the cutting guides 220 onto the clamp members 218 by actuating the head 231 to turn down the threaded shaft 234 with respect to the clamp member 218. Note the retaining head 232 of the A-P adjustment screws prevent the shaft 234 from being backed off out of engagement with the clamp member 218.

Figure 14:
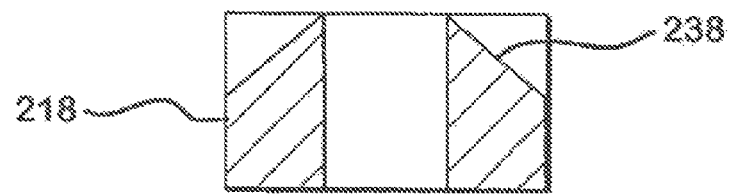
FIG. 14 is a cross-sectional view of the profile of the ends of the clamp members taken along line A-A in FIG. 12.
Figure 15:
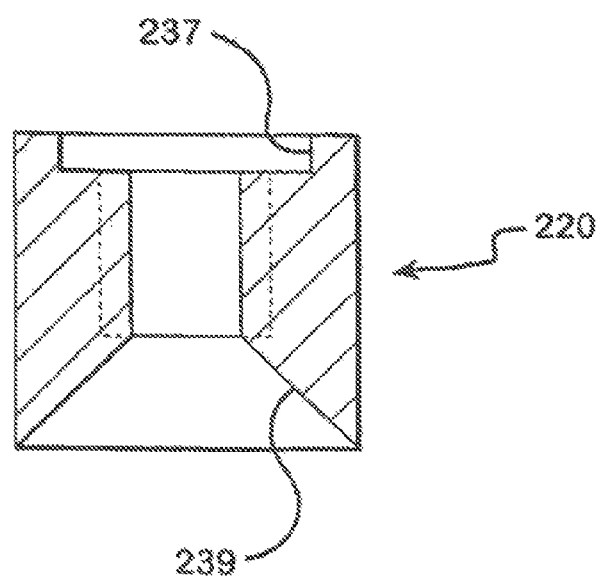
FIG. 15 is a cross-sectional view of the profile of the ends of the cutting guides taken along line B-B in FIG. 12, the ends of the clamps mating with the ends of the cutting guides for positioning the cutting guides with respect to the clamps.

As shown in FIGS. 14 and 15, respectively, the clamp members 218 are shaped with opposing interior edges having chamfers 238 and the opposite exterior edges of the cutting guides 220 have mating recesses 239, both of said profiles extending along the contacting surfaces of the clamp members 218, as seen along line A-A in FIG. 12, and the cutting guides 220, as seen along line B-B in FIG. 12, to maintain a proper planar alignment therebetween. It should of course be noted that any other method known in the art may be employed to maintain the clamp members 218 and the cutting guides 220 in alignment. Additionally, the cutting guides 220 may include A-P adjustment screw recesses 237 for receiving the head 231 of the A-P adjustment screw 230.

The cutting guides 220 further include tibia attachment means for attaching the cutting guides 220 to the tibia 208. Any known attachment means may be employed to attach the cutting guides 220 to the tibia 208. As shown in FIGS. 9 and 11, a preferred attachment means for attaching the cutting guides 220 to the tibia 208 are pins 236 extending through pin apertures 227 in the cutting guides 220. The pins 236 may be captured in the pin apertures 227, or they may be entirely separate. Preferably, means exist on the cutting guides 220 for preliminarily attaching the cutting guides 220 to the tibia 208 prior to pinning the cutting guides 220 thereto, so that after proper positioning of the cutting guides 220, the hand grips 212 can be actuated by squeezing the hand grips 212 together to contact the cutting guides 220 against the tibia 208 so that the cutting guides 220 are preliminarily attached to the tibia 208. Such means may include a plurality of small pins captured by the cutting guide 220, or any other suitable means. After the preliminary attachment of the cutting guides 220 to the tibia 208, final attachment may be made by attachment pins 236 or by any other means known in the art.

The cutting guides 220, importantly, include cutting slots 222 which each comprise lower cutting slot guide surface 223 and upper cutting slot retaining surface 225, as well as cutting slot entrance and exit 224 at one end thereof and cutting slot end wall 226 at the other end thereof. The cutting slot 222 is of a length sufficient to extend across the proximal tibia 208, at a desired angle to the intermedullary canal, at the widest point of the proximal tibia 208, to allow the entire upper surface of the proximal tibia 208 to be cut. The cutting slot 222 is of a size sufficient to receive a cylindrical milling bit 255 such as that shown in FIG. 16 and described in U.S. Pat. No. 5,514,139, filed Sep. 2, 1994 by Goldstein, et al. The milling bit 255 comprises central cutting portion 257 having helical cutting teeth along its length for cutting bone. The milling bit 255 further comprises spindles 256 extending from the central cutting portion 257 for supporting the central cutting portion 257.

Figure 16:
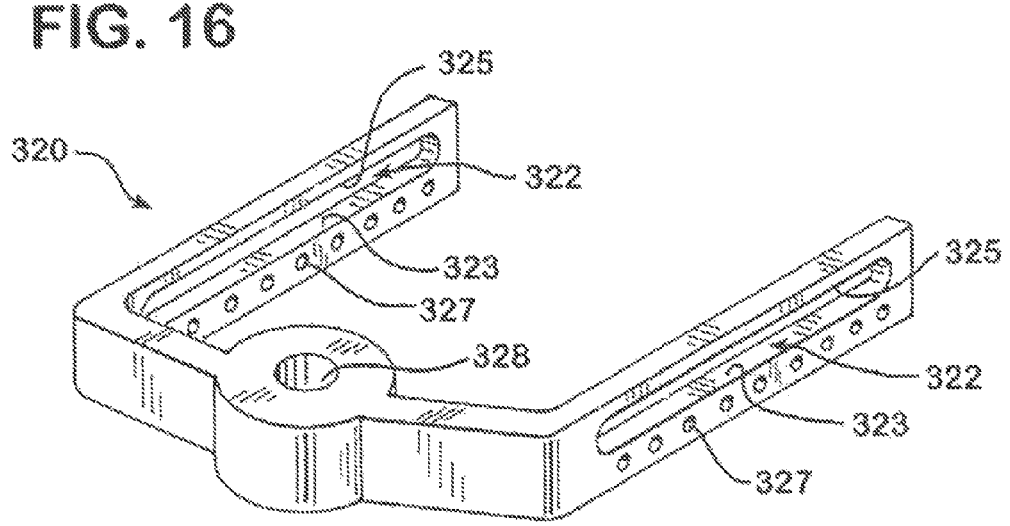
FIG. 16 is a perspective view of an alternate embodiment of a U-shaped cutting guide for use in the present invention.

The milling bit 255 is inserted into and received in the cutting slot 222 through cutting slot entrance 224, along the direction shown by arrow A in FIG. 16. Note that the cutting slot entrance 224 may be of a wider slot area or an upturned portion of the slot 222 or the milling bit 255 may merely be inserted and removed from the slot 222 at an end thereof. The spindles 256 extend through and co-act with the lower cutting guide surface 223 and the upper retaining surface 225 of the cutting slot 222 to guide the milling bit 255 along the cutting slot 222 to resect the proximal tibia 208, along the direction shown by arrow B in FIG. 16. At an end of one or both of the spindles 256 is a means for engaging the milling bit 255 with a drive means such as an electric drill, or other drive means. This engagement means may include a hexagonal head on one of the spindles, or any other suitable method of engagement known in the art. Additionally, bushings may be employed, either on the milling bit 255 or captured by the cutting slot 222, to provide a non-metallic bearing between the spindles 256 of the milling bit 255 and the cutting slot 222 to avoid galling and to ensure smooth articulation of the milling bit 255 along the cutting slots 222. Importantly, the configuration of the milling bit 255 may be varied in accordance with what is known in the art, as long as the cutting device can follow the cutting path of the cutting slot to resect the proximal tibia. Additionally, it should also be pointed out that other cutting tools may be used in accordance with the present invention, including an oscillating or reciprocating saw or other means for resecting the tibia by following the cutting slots on the cutting guides.

After the cutting guide clamps 210 are preliminarily located along the alignment rod 260, the cutting guides 220 are adjusted with respect to the clamp members 218 for proper anterior-posterior positioning to extend along the proximal tibia 208 for guiding the milling bit 255. Importantly, the cutting slots 222 should extend beyond the edges of the proximal tibia 208. Once proper anterior-posterior alignment is obtained, the cutting guides 220 may be locked into place on the clamp members 218.

Thereafter, a proximal tibial referencing stylus 290 may be attached to a referencing bracket 292 on the cutting guides 220. The referencing bracket 292 may be positioned in any location on the cutting guides 220, or on any other convenient component of the tibia resection system of the present invention. Alternatively, the referencing stylus 290 may be formed as part of a component of the present invention, or as a separate component which could function merely by contacting the cutting guides 220 of the present invention or any other component thereof. The referencing stylus 290, shown in FIG. 13, includes stylus body 294 which may be interconnected with the referencing bracket 292 in any manner known in the art, preferably by a quick release and connect mechanism or a threaded connection. The stylus body 294 supports a stylus arm 296, which is rotatable with respect to the stylus body 294 and configured to extend out and down from the stylus body 294 to contact the proximal tibia 208 at a tip 298 of the stylus arm 296. The stylus body 294, arm 296, and tip 298 are sized to contact the proximal tibia 208 to reference the positioning of the cutting guides 220 to cut the proximal tibia at a proper distance below the proximal tibia 208 as is known in the art. The stylus arm 296 may include more than one tip 298, such other tips extending down from the stylus body 294 in varying distances.

In operation, one determines the desired location of the stylus tip 298, unlocks the cutting guide clamp linkage 270 to permit the linkage 270 to move up and down the alignment rod 260, and places the tip 298 on the lowest point of the proximal tibia 208 to reference the position of the cutting guides with respect to the proximal tibia 208 and with respect to the alignment rod 260. Thereafter, the cutting guide clamp linkage 270 is locked to the alignment rod 260 to lock the cutting guides 220 into the proper position on the alignment rod 260, and accordingly, into proper position with respect to the proximal tibia 208. Thereafter, the hand grips 212 are actuated to press the cutting guides 220 against the proximal tibia 208 to preliminarily lock them into position on the proximal tibia 208. Next, the cutting guides 220 are fixed to the proximal tibia 208 by pins 236 or any other desired fixation means. The fixation block 280 can then be removed from the proximal tibia 208, and the proximal tibia 208 may be resected.

The cutting operation is similar to the cutting operation set forth in U.S. Pat. No. 5,514,139, filed Sep. 2, 1994 by Goldstein, et al. Essentially, the cutting operation comprises inserting the milling bit 255 into the cutting guide slots 222 through the slot entrance/exit 224 to position the central cutting portion 257 between the cutting guides 220, the spindles 256 extending through the cutting guide slots 222. After the milling bit 255 is positioned, the drive means may be interconnected therewith, actuated, and the milling bit 255 moved along the cutting slots 222 to resect the proximal tibia 208.

It should be noted that a handle may be provided for attachment to the spindle which is not driven so that such spindle may be guided evenly through the cutting slots 222 to facilitate the cutting procedure. Alternatively, a handle can be provided which interconnects with both spindles to further facilitate control of the milling bit 255 during the cutting procedure. Additionally, the bushings that fit over the spindles 256 of milling bit 255 and ride in the cutting slots 222 may be captured in the ends of the handle and the milling bit received therethrough.

Additionally, it should be pointed out that it is within the scope of the present invention to modify the cutting slots 222 such that the upper retaining surface is eliminated, and the milling bit 255 merely follows the lower cutting guide surface 223. With the cylindrical milling bit 255 herein described, this is especially viable as the milling bit 255 tends to pull down into the bone as it is cutting, thereby primarily utilizing the lower cutting guide surface 223 of the cutting guide 220.

Figure 18:
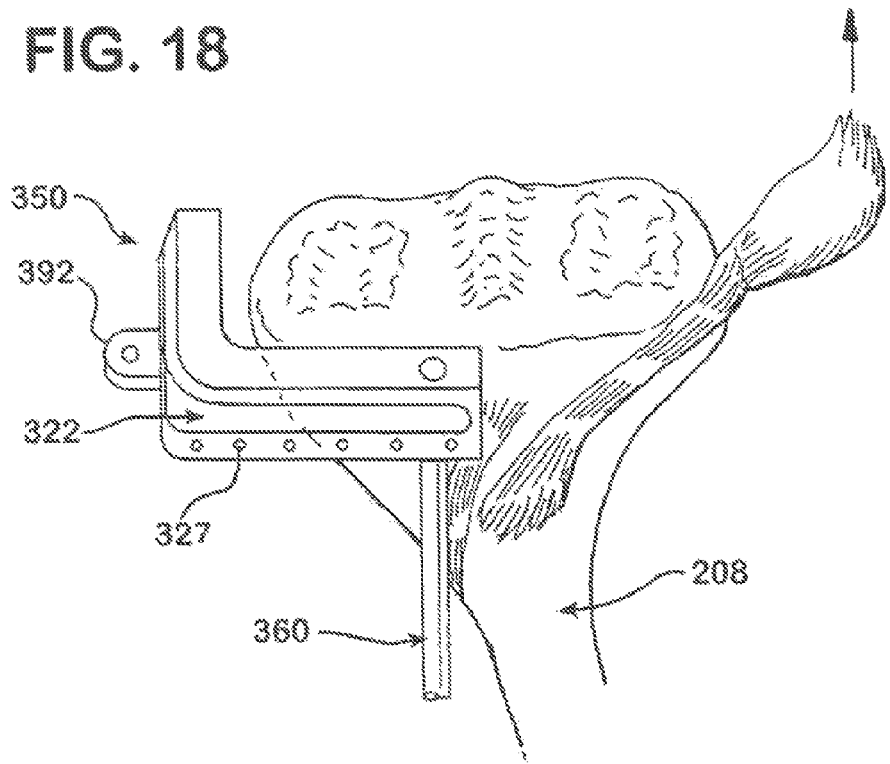
FIG. 18 is a perspective view of another alternate embodiment of a partial cutting guide for use in the present invention when the patellar tendon, patella, or quad tendon interferes with placement of the cutting guide about the tibia.

As shown in FIGS. 16-18, various other embodiments of the cutting guides are considered within the scope of the present invention. The cutting guide 320 shown in FIG. 16 is of a generally U-shaped configuration, having cutting guide slots 322, lower cutting guide surface 323, upper retaining surface 325, pin apertures 327, and alignment rod aperture 328. This cutting guide 320 is used in the same manner as the cutting guides hereinbefore described, the differences being that the cutting guide 320 interconnects directly with the alignment rod and that various size cutting guides must be provided to accommodate various sized tibias.

Likewise, the cutting guide 320, shown in FIG. 17, operates in the same manner as the cutting guide devices hereinbefore described, but it does not include cutting guide clamps. The cutting guide 320 includes cutting slots 322, and it interconnects directly with alignment rod by means of aperture 328. The distance between facing members 330 can be adjusted by moving base members 332 and 334 with respect to each other to size the cutting guide 320 for the tibia to be cut. Upon proper sizing, the base members 332 and 334 may be locked with respect to each other by set screw 336 or any other means known in the art.

FIG. 18 shows an embodiment of the cutting guide for use when the patellar tendon, the patella, or the quad tendon interferes with the placement of the other cutting guides of the present invention. As shown in FIG. 18, the cutting guide 350 may be directly interconnected with the alignment rod, and positioned on the tibia as hereinbefore set forth. Basically, this embodiment of the invention includes only one cutting guide. The cutting guide 350 and the cutting guide slot 322 may be wider than in the previous embodiments to help stabilize the milling bit in operation. In this embodiment, the milling bit may be first plunged across the tibia, and then moved therealong. The milling bit may be spring loaded to increase resistance as it is plunged through the cutting guide to bias the bit against being plunged too far across the tibia to cause damage to the tissue about the tibia. Additionally, a support member, not shown, could be provided to extend from the cutting guide 350, over and across the tibia to the other side thereof where it could have a slot to capture the milling bit and provide additional support thereto. The reference numerals 338, 360 and 392 correspond to the reference numerals 238, 260 and 292 respectively. As can be seen in FIG. 18, the cutting guide 350 can have a generally L-shaped or generally J-shaped configuration.

As shown generally in FIGS. 19-23, the pattern apparatus of the present invention, generally indicated at 430, comprises pattern plates, generally indicated at 432, and crossbar apparatus, generally indicated at 440.

Pattern Plates

Pattern plates 432 include fixation apertures 434 extending therethrough for accepting fixation means, as will hereinafter be described, for affixing the pattern plates 432 to a bone. The pattern plates 432 further include a cutting path 436 for dictating the path along which a bone is to be cut. As shown in FIGS. 19-23, which are directed to an embodiment of the present invention for resecting a distal femur, the cutting path 436 in the pattern plates 432 matches the profile of a femoral component of a knee prosthesis for resecting the femur to accept the femoral component of the prosthesis. Importantly, as will hereinafter be described, the cutting path 436 could be identical in size and shape to an interior bearing surface of a femoral component of the knee prosthesis, or could vary in size and shape in accordance with alternative methods and apparatus used to perform the resection. For example, the cutting path could be larger than the desired resection, but a larger cutting tool could be used to arrive at a resection of the desired the desired size.

Figure 21:
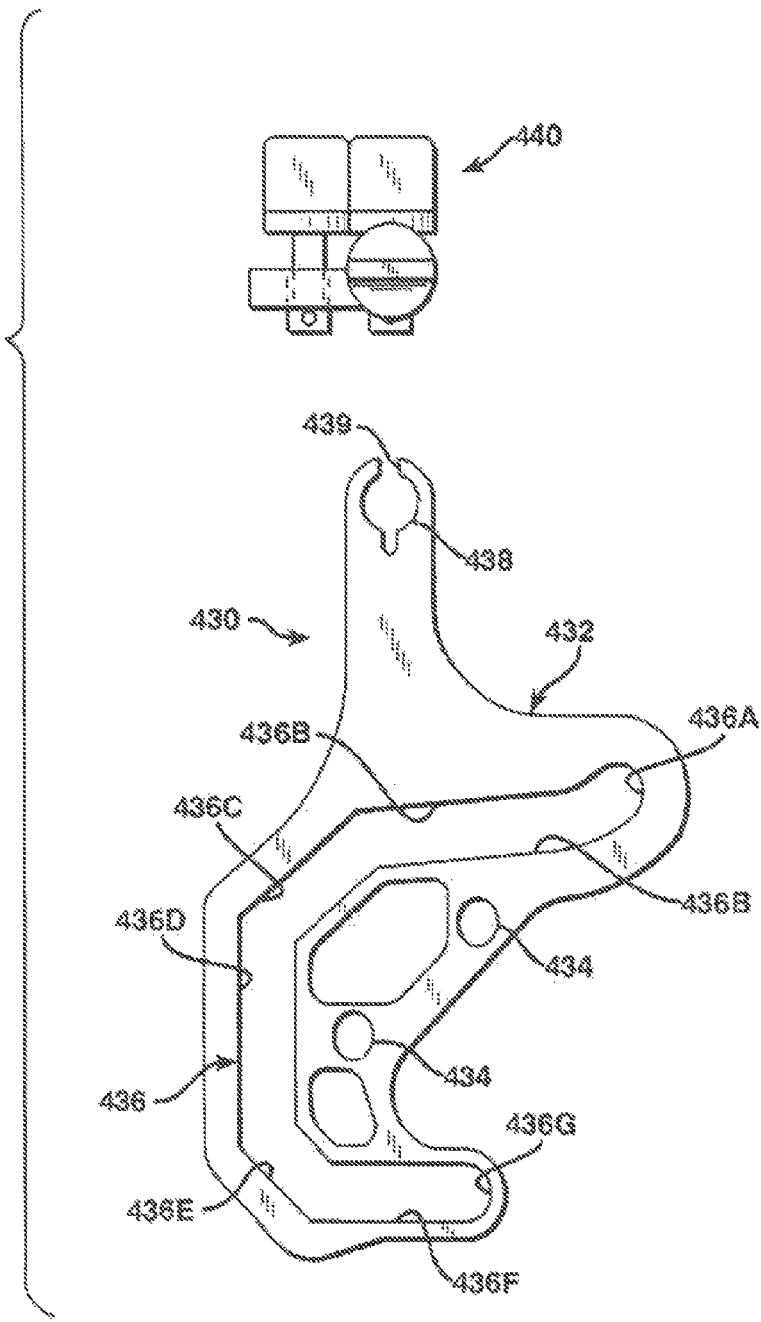
FIG. 21 is a partially exploded side plan view of the positioning apparatus shown in FIG. 19.
Figure 22:
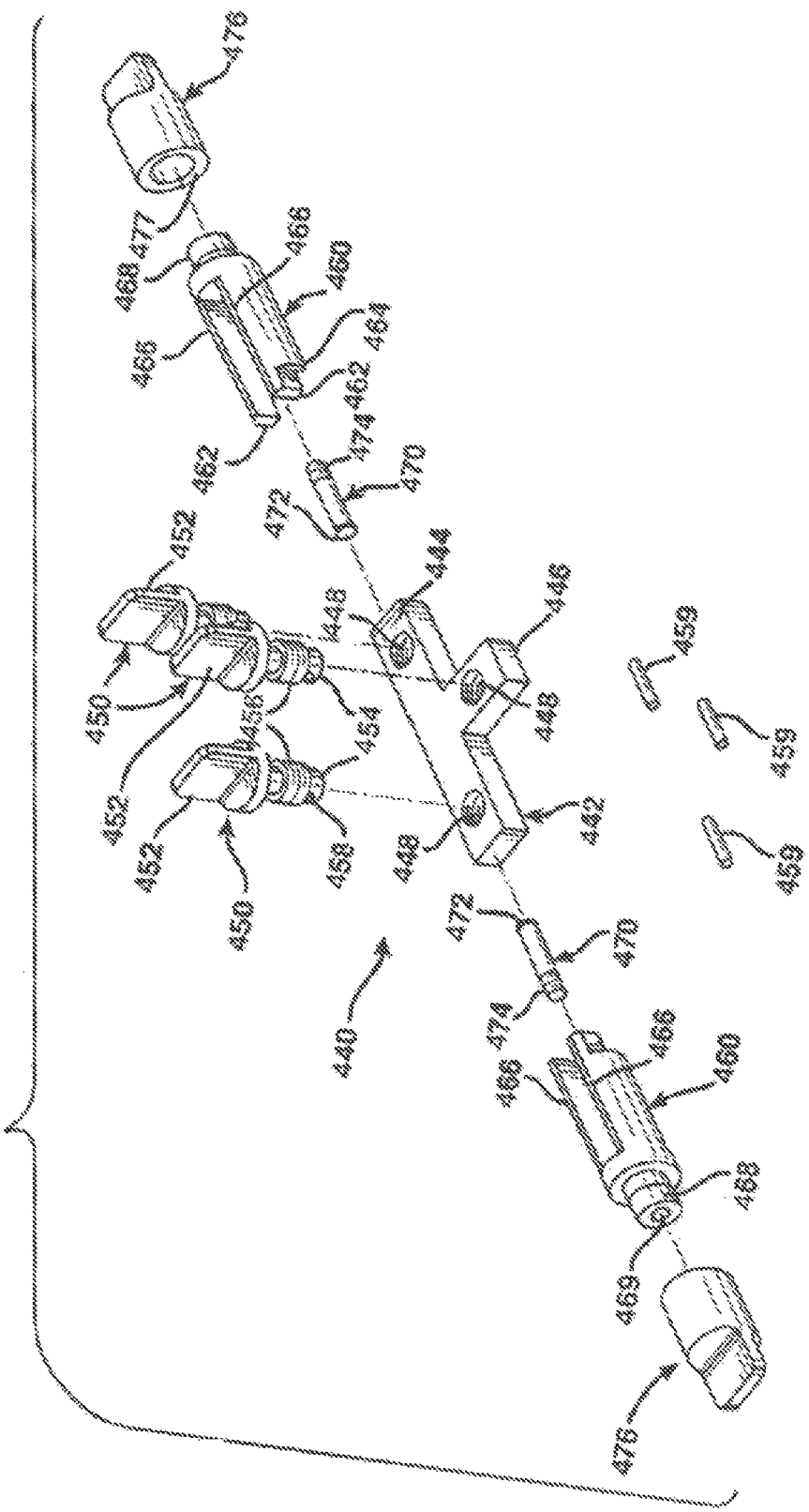
FIG. 22 is an exploded perspective view of the cross-bar of the pattern apparatus shown in FIG. 19.
Figure 23:
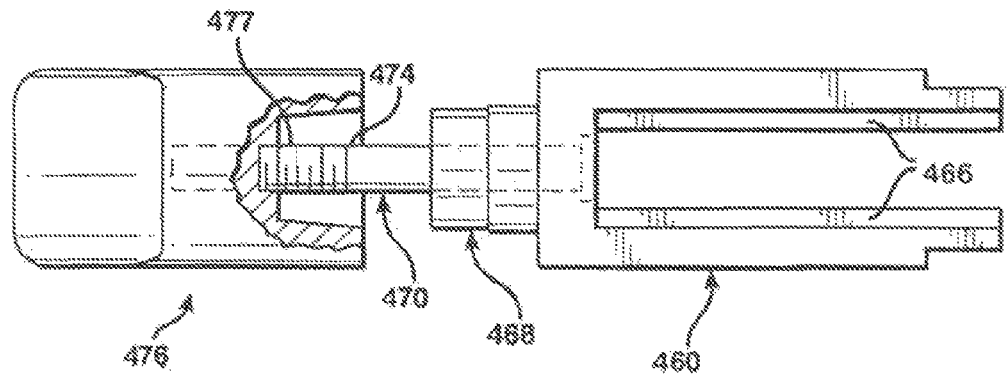
FIG. 23 is a partially cut away side plan view of the pattern plate/cross-bar attachment linkage for interconnecting the pattern plate to the cross-bar as shown in FIG. 19.
Figure 24:
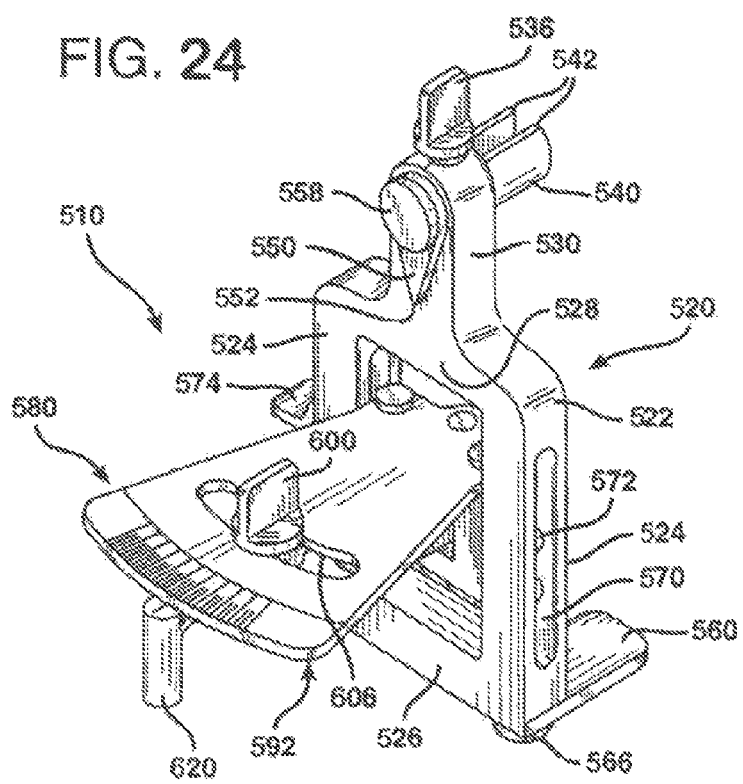
FIG. 24 is a perspective view of the positioning apparatus of the present invention.
Figure 25:
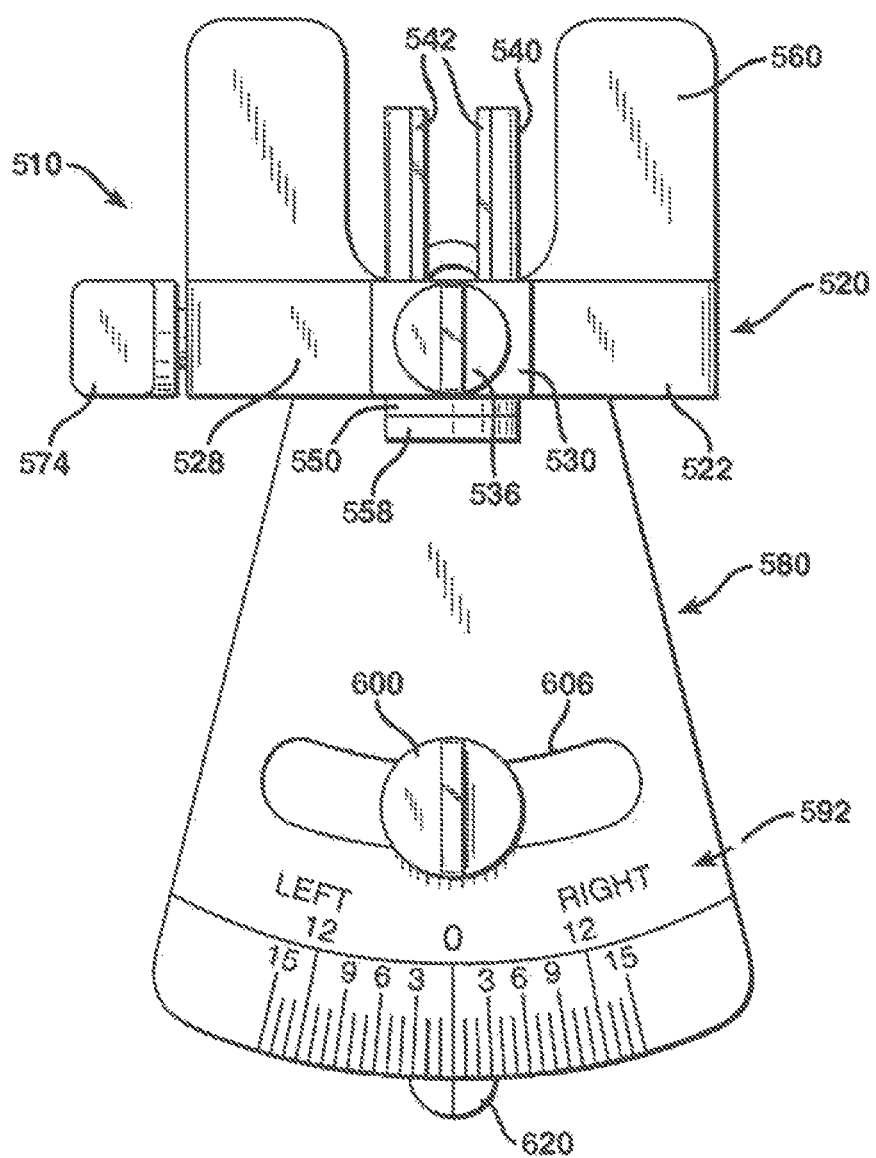
FIG. 25 is a top plan view of the positioning apparatus shown in FIG. 24.
Figure 26:
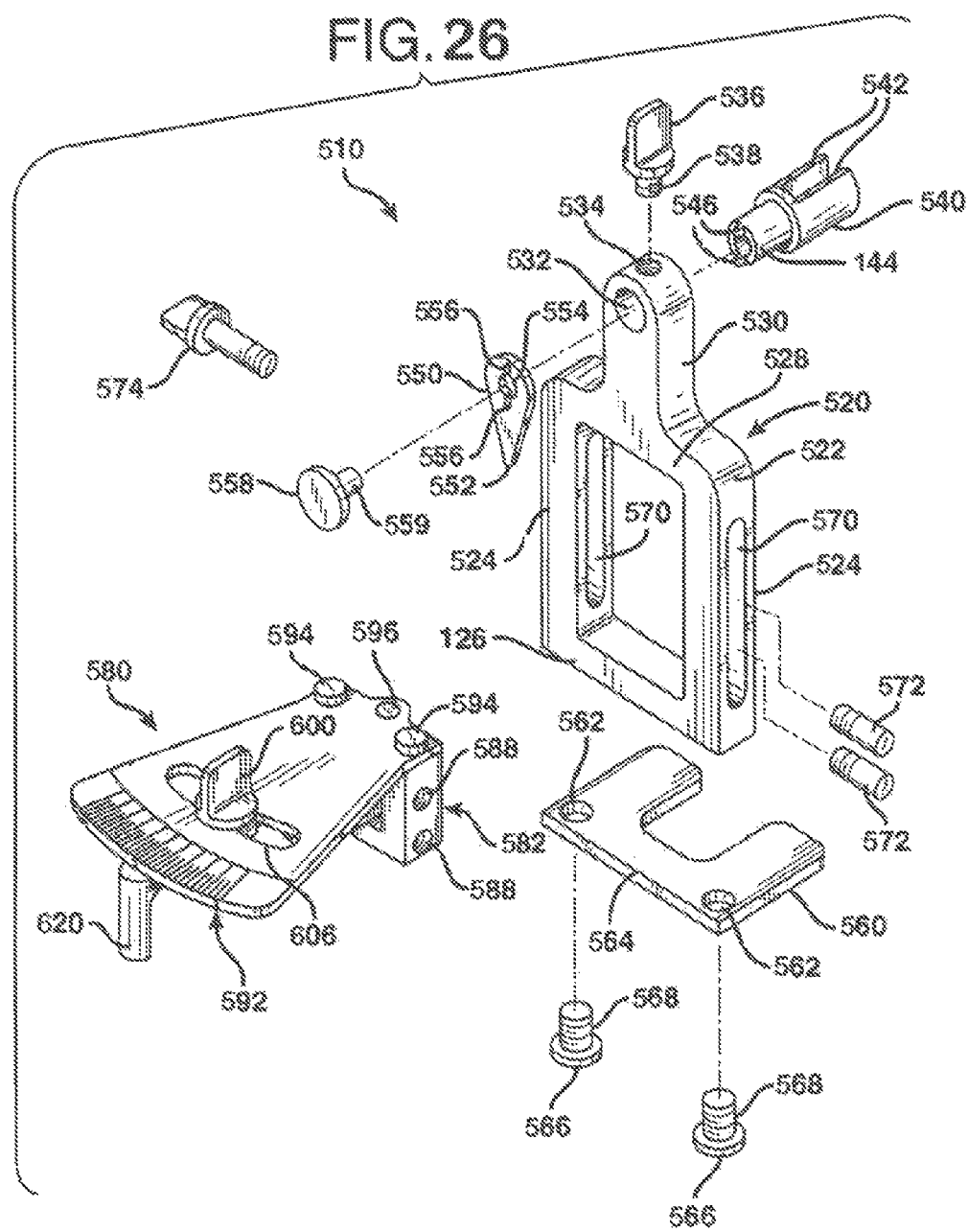
FIG. 26 is an exploded perspective view of the positioning apparatus shown in FIG. 24.
Figure 28A:
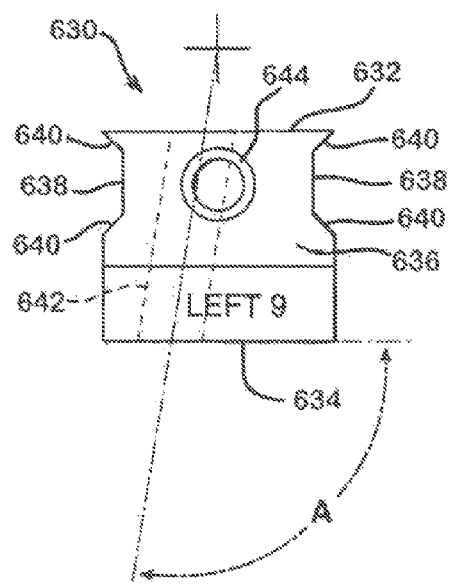
FIGS. 28A-28D are plan views of another embodiment of a rod guide assembly for use with the positioning apparatus shown in FIG. 24.
Figure 28B:
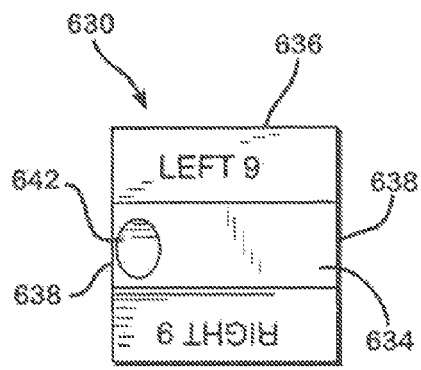
Figure 28C:
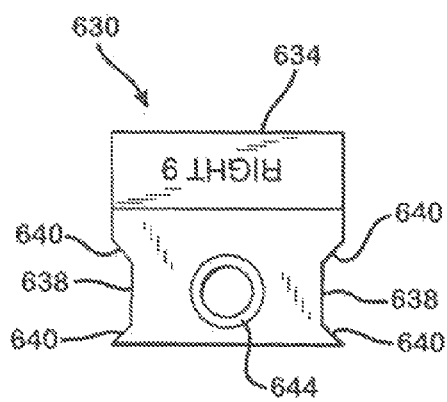
Figure 28D:
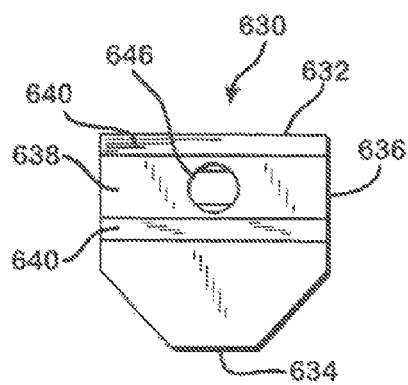

In the embodiment of the present invention shown in FIG. 21, the cutting path 436 includes an anterior end 436A, an anterior cut portion 436B, an anterior chamfer portion 436C, a distal cut portion 436D, a posterior chamfer portion 436E, a posterior cut portion 436F, and a posterior end 436G. Alternatively, the cutting path 436 could be of any desired shape in accordance with the prosthesis systems of the various manufacturers of such prosthesis, the desires of the surgeon utilizing the apparatus and/or the application for which a bone is to be cut.

Figure 19:
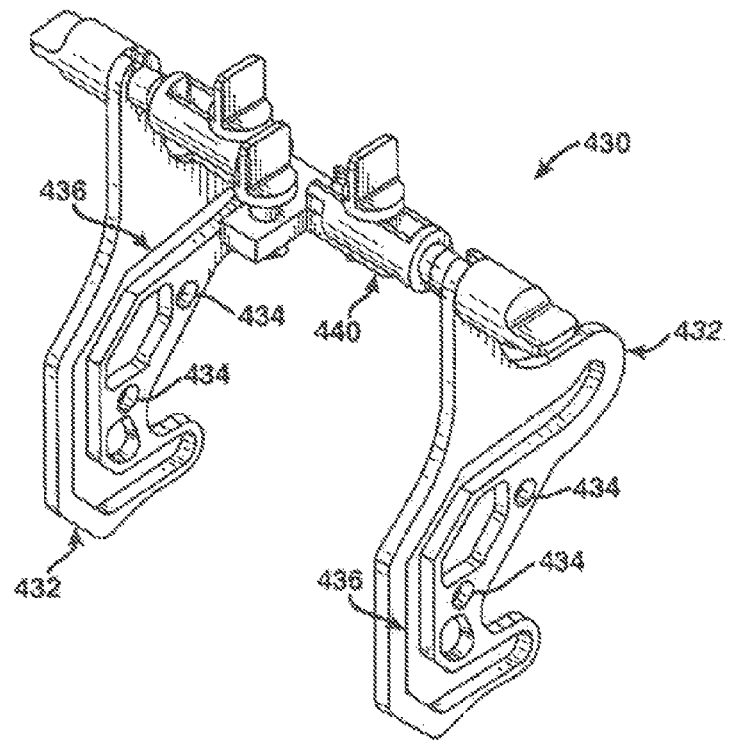
FIG. 19 is a rear perspective view of an embodiment of the pattern apparatus of the present invention.
Figure 20:
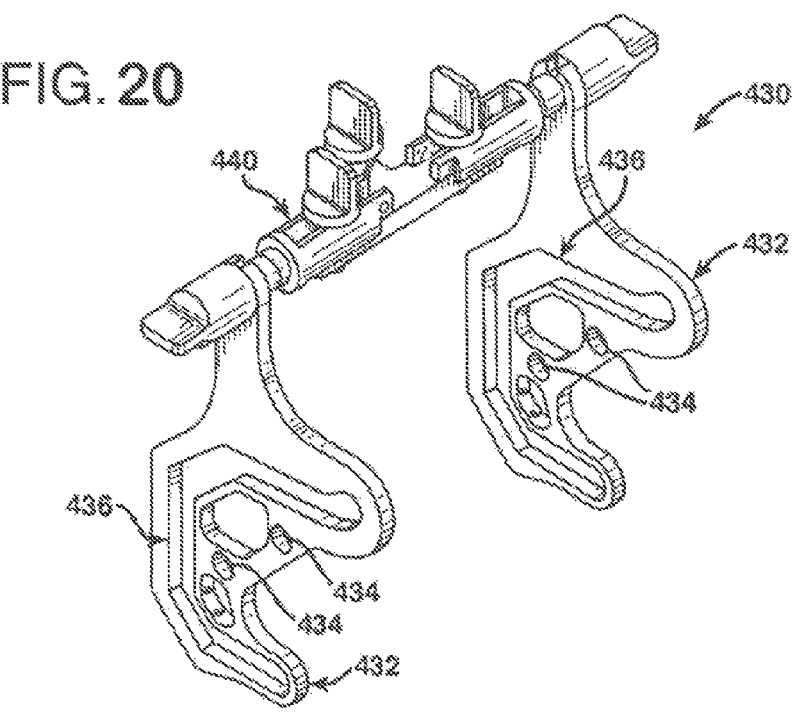
FIG. 20 is a front perspective view of the pattern apparatus shown in FIG. 19.

Although a single pattern plate 432 may be employed in resecting a femur or other bone (and in some cases, i.e., a partial femur resection, it may be preferable to employ a single pattern plate 432), two pattern plates 432 are generally employed to co-act with each other to support a cutting means on two sides of a bone to be cut. In the case of resecting a femur, a preferred embodiment of the present invention, as shown in FIGS. 19-21, comprises two pattern plates 432 positioned on opposing sides of a femur. The pattern plates 432 are interconnected with each other, and maintained in proper alignment with respect to each other by a crossbar apparatus generally indicated at 440, to straddle a bone. The pattern plates 432 include crossbar apertures 438 for interconnecting with the crossbar apparatus 440. The pattern plates may also include crossbar slots 439 for permitting quick connect/disconnect between the pattern plates 432 and the crossbar apparatus 440. Of course, it should be noted that the pattern plates 432 could interconnect with the crossbar in any other manner known in the art, or especially with bone cutting applications other than resecting the femur, the pattern plates 432 could be used without a crossbar.

Crossbar Apparatus

The crossbar apparatus 440 includes a number of component parts, namely, T-bar 442 having a top 444 and a stem 446 interconnected with and extending from the top 444 in the same plane. The T-bar 442, shown in the figures, comprises a flat metal member having a uniform rectangular cross-section through both the top 444 and the stem 446. Three threaded lock apertures 448 are formed through the T-bar 442, one at each end of the top 444 and at the far end of the stem 446. Lock screws 450, having gripable heads 452 and shafts 454 with threaded waists 456, threadably engage the threaded lock apertures 448 in the T-bar 442. The lock screws 450 further include pin holes 458 extending radially through the shafts 454 at the terminal ends thereof for receiving pins 459 for capturing the lock screws 450 on the T-bar 442.

The crossbar apparatus 440 further includes linkages 460 having a first end for interconnection with the T-bar 442 and a second end for supporting and engaging pattern plates 432. The first ends of the linkage 460 include a lower flat surface 462 for contacting the T-bar 442, overhanging shoulders 464 for contacting the sides of the T-bar 442, and an upper flat surface 466 for contact with the lock screws 450 for locking the linkages 460 onto the T-bar 442. As shown in detail in FIG. 23, the second ends of the linkage 460 include cylindrical supports 468 for supporting the pattern plates 432 thereon. The cylindrical supports 468 include axial extending apertures 469 for receiving capture pins 470 therethrough, the capture pins 470 including flanged ends 472 and threaded ends 474. The capture pins 470 serve to capture pattern lock nuts 476 on the linkages 460, the capture pins 470 extending through the axial apertures 469, the flanged ends 472 retaining the capture pins 470 therein, the threaded ends 474 extending out of the cylindrical supports 469 and into the threaded interior 477 of the pattern lock nuts 476. The cylindrical supports 468 receive the crossbar apertures 438 of the pattern plates 432 and the pattern lock nuts 476 are threaded down onto the capture pins 470 to secure the pattern plates 432 to the crossbar apparatus 440. Of course, other embodiments of the crossbar apparatus sufficient for supporting the pattern plates of the present invention are considered within the scope of the present invention.

Positioning Apparatus

As shown in FIGS. 24-28, the positioning apparatus of the present invention is generally indicated at 510. The positioning apparatus generally comprises positioning body 520 and alignment apparatus 580. The positioning body 520 comprises a frame 522 having sides 524, bottom 526 and top 528 arranged to form a frame having a rectangular aperture defined therewithin. The top 528 further includes a head 530 formed thereon having a linkage aperture 532 extending therethrough at an upper end thereof, and having a lock aperture 534 extending from the upper edge of the head to the linkage aperture 532. A lock screw 536 having a threaded shaft 538 extends into and is threadably engaged with the lock aperture 534 for locking the head 530 to a linkage, namely crossbar linkage 540. Crossbar linkage 540 includes a first end having an upper flat surface 542 for interconnecting with the crossbar in a manner similar to the pattern plate linkages for attaching the pattern plates to the crossbar as hereinbefore described. The crossbar linkage 540 further includes a shaft 544 which is received by the linkage aperture 532 in the head 530 to interconnect the positioning body 520 with the crossbar linkage 540 and hence with the crossbar apparatus 440 and the pattern apparatus 430. The positioning body can then be locked onto the crossbar linkage 540 by means of lock screw 536.

The end of shaft 544 of the crossbar linkage 540 includes projections 546 extending axially from the shaft 544. When the shaft 544 is positioned in the linkage aperture 532, the projections 546 extend beyond the frame 522 and are received in slots 556 in alignment indicator 550 for keying the orientation of the alignment indicator 550 with the alignment of the crossbar linkage 540, and hence with the alignment of the crossbar apparatus 440 and the pattern apparatus 430. The alignment indicator 550 includes an alignment arrow 552 for indicating alignment on a scale that may be set forth on the positioning body 520. An indicator pin 558 having a shaft 559 may be employed to pin the alignment indicator 550 to the crossbar linkage 540.

Attachable to the bottom 526 of the positioning body 520 is skid 560. The skid 560 includes skid apertures 562, one of which may include an aperture flat 564 for ensuring proper alignment and positioning of the skid 560 with respect to the positioning body 520. The skid 560 is attached to the bottom 526 of the positioning body 520 by means of skid bolts 566 having threaded shafts 568 which co-act with threaded apertures in the bottom 526 of the positioning body 520. Of course, the skids could be formed integrally as part of the positioning body.

The sides 524 of the positioning body 520 include slots 570 extending in a facing relationship along the sides 524. The slots extend from exterior surfaces of the sides to interior surfaces thereof, i.e., to the interior rectangular aperture formed within the positioning body 520.

Alignment Apparatus

The alignment apparatus 580 interconnects with the positioning body 520 by means of alignment guide body 582 which is a U-shaped member having sides 584 and a bottom 586. The alignment guide body 582 is sized to fit within the rectangular aperture formed within the positioning body 520. The alignment guide body 582 is retained within the positioning body by means of guide studs 572 that extend through the sides 524 of the positioning body 520 within the slots 570 and into guide apertures 588 at one side of the alignment guide body 582. At the other side of the alignment guide body 582 a lock stud 584 extends through the slot 570 in the side 524 of the positioning body 520 and into a threaded lock aperture 589 in the alignment guide body 582. The guide studs 572 and the lock stud 574 co-act to maintain the alignment guide body 582 within the positioning body 520, and the lock stud 574 can be threaded down to lock the vertical position of the alignment guide body 582 with respect to the positioning body 520.

At upper ends 590 of the sides 584 of the alignment guide body 582 are plate apertures 591. The alignment plate 592 includes bolt apertures 595 aligned with the plate apertures 591 of the alignment guide body 582, and plate bolts 594 extend through the bolt apertures 595 in the alignment plate 592 and into the plate apertures 591 to secure the alignment plate 592 to the alignment guide body 582. The alignment plate 592 further includes rod guide aperture 597 which receives rod guide bolt 596 therethrough to interconnect the alignment plate 592 with the IM rod guide 610 as will hereinafter be described. Additionally, the alignment plate 592 includes lock slot 606 extending through the alignment plate 592 along an arc for purposes hereinafter described.

The IM rod guide 610 includes IM rod aperture 612 for receiving an IM rod therethrough. The IM rod guide 610 is interconnected at a forward end with the alignment plate 592 by means of plate attachment aperture 614 on the rod guide 610 which receives rod guide bolt 596 therein, after such bolt 596 passes through the alignment plate 592 to secure the rod guide 610 in a pivoting relationship with respect to the alignment plate 592 at forward ends of the rod guide 610 and the alignment plate 592. The IM rod guide 610 is additionally interconnected with the alignment plate 592 by rod guide lock bolt 600 which includes a threaded shaft 210 and pin aperture 602. The rod guide lock bolt 600 extends through the slot 606 in the alignment plate 592 and through threaded lock bolt aperture 616 in the rod guide 610 where it is captured by means of capture pin 618 extending through the pin aperture 602. The IM rod guide further includes rod guide handle 620 which is configured to be easily manipulated.

The alignment plate 592 further includes a printed angular rotation scale which indicates the degree of angular rotation between the rod guide 620 and the alignment apparatus, and hence, the angular rotation between the IM rod and the positioning body 520. After such alignment is determined, it can be locked into place by tightening down rod guide lock bolt 600. Thereafter, with such angular rotation fixed, the pattern apparatus 430 can be positioned with respect to the bone to cut, and the positioning apparatus 510 can be removed from interconnection with the IM rod and the pattern apparatus 430, the IM rod removed from the bone, and bone cutting can be initiated.

In another embodiment, as shown in FIGS. 28A, 28B, 28C, and 28D, IM rod guide block 630 is used instead of the alignment plate 592 and the alignment guide body 582. The IM rod guide block 630 includes a rear surface 632, a front surface 634, a top surface 636, and sides 638. The sides 638 include retaining flanges 640 at the rear and front surfaces for retaining the IM rod guide block 630 within the rectangular aperture formed by the positioning body 520. The IM rod guide block 630 further includes IM rod aperture 642 extending through the block 630 from the rear surface 632 to the front surface 634 for accepting the IM rod therethrough. The rod aperture 642 extends through the guide block 630 at an angle A with respect to axis of the guide block for accommodating the varus/valgus orientation of the femur. The guide block 630 is part of a set of blocks having rod apertures of various angles extending therethrough, i.e., 5, 7, 9, 11, 13 degrees, for use with femurs having varying angles of orientation. The guide block 630 also includes lock aperture 646 for locking the proper vertical position of the guide block 630 with respect to the positioning body 620. The guide block 630 may additionally include two apertures 644 for accepting an anterior referencing arm for use in determining the anterior/posterior size of the femur. It should be noted that other alignment means for aligning the positioning apparatus with respect to a bone to be cut are considered within the scope of the present invention.

Fixation Means

Figure 29:
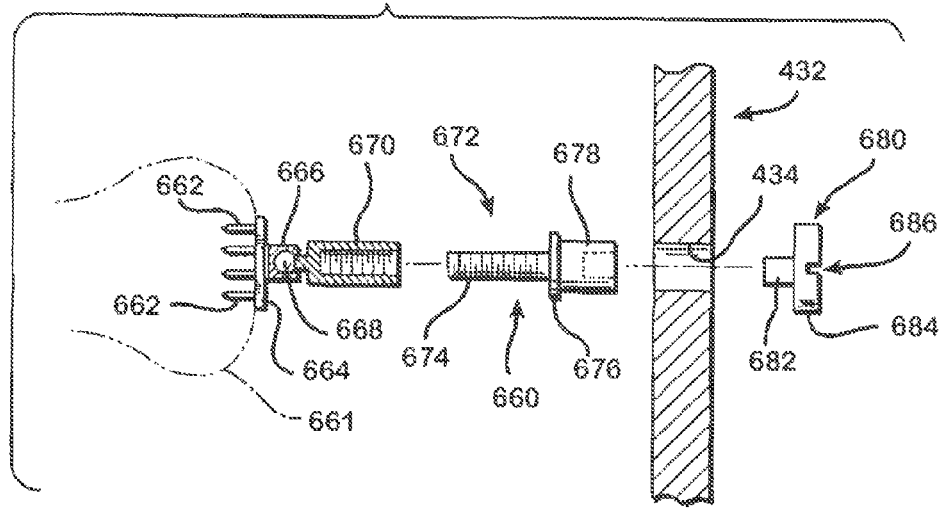
FIG. 29 is a side plan view of an embodiment of the fixation device for affixing the pattern apparatus shown in FIG. 19 to a bone.

Various fixation means, including those known in the art, can be used to fix the pattern plate or plates to the femur or other bone to be cut. FIG. 29 shows a preferred fixation means, generally indicated at 660. The fixation means 660 includes a spike plate 664 carrying on one side thereof a spike or spikes 662 for contacting, and even extending into, bone 661. At the other side of the spike plate 664 is spike plate socket 666 for receiving plate driving ball 668 in a keyed relationship therewith. The driving ball 668 is interconnected to an end of driving sleeve 670 and which has a threaded aperture extending therein from the opposite end thereof.

A driving screw 672 having a threaded shaft 674 co-acts with the internally threaded driving sleeve 670 such that the rotation of the driving screw 672 either propels or retracts the driving sleeve 670, as well as the spike or spikes 662, with respect to the driving screw 672. The driving screw 672 further includes a captured head 678 and capture flange 676. The captured head 678 is received within a fixation aperture 434 in the pattern plate 432, the capture flange 676 preventing the captured head 678 from passing through the fixation aperture 434. A driving cap 680 is interconnected with the captured head 678 at the outside of the pattern plate 432. The driving cap 680 includes a shaft 682 received by the captured head 678, a flanged head 684 for contacting against the outside of the pattern plate 432, and a driver recess 686 of any desirable configuration for receiving driving means such as a flat, phillips, or hex head driving means for driving the driving cap 680 to drive the driving screw 672 to move the spike or spikes 662 towards or away from a bone.

Importantly, this type of fixation means allows for fixation of the pattern plates 432 to even osteoporotic bones. Additionally, this fixation means is self-adjusting to fit changing contours of bones. Further, because of its relatively low profile, this fixation means does not interfere with soft tissue about a bone to be cut. Other types of fixation means include cannulated screws, pins, spring loaded screws, captured screws, spiked screws and/or combinations thereof, all of which are considered within the scope of the present invention and could be used in connection with the present invention.

Anterior/Posterior Referencing

Figure 30:
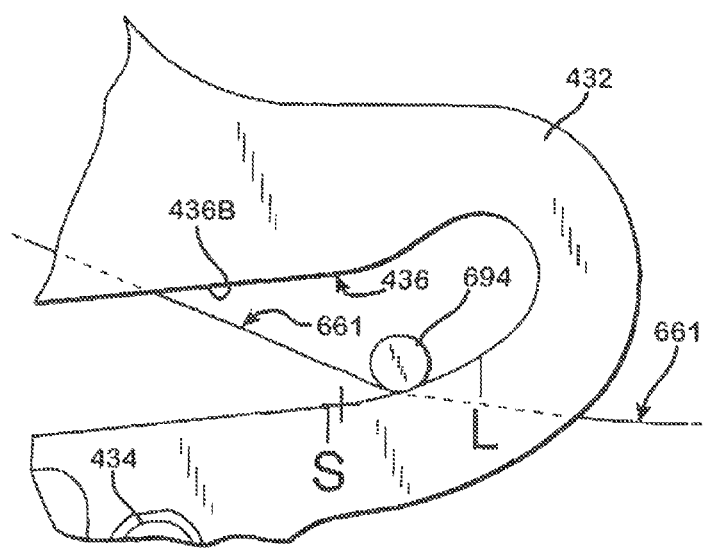
FIG. 30 is a partial side plan view of the pattern apparatus shown in FIG. 19, showing the posterior/anterior referencing guide.

The apparatus of the present invention further includes built-in anterior/posterior referencing means as shown in FIG. 30 for use in connection with preparation of the distal femur in total knee replacement. As is known in the art, anterior/posterior referencing refers to proper positioning of the distal femur cuts with respect to the anterior and/or posterior sides of the femur or other bone to be cut.

The anterior/posterior difference between femoral implant sizes may vary by as much as 3 to 5 millimeters between sizes. Of course, many femurs are between sizes. Disregarding proper positioning of the cutting guide and the associated femur cuts could lead to flexion contracture (where the bone is slightly below size and the implant adds too much material to posterior side of femur which results in the inability to move the knee into flexion because the extra posterior material contacts the tibial implant components) and/or anterior notching of the femur (where the bone is slightly above size and the anterior runout point of the anterior cut is recessed in the anterior side of the bone in a sharp notch, thus seriously weakening the structural integrity of the distal femur, especially under cyclic fatigue or impact loading conditions).

Anterior referencing systems have a major advantage over posterior referencing systems in that they theoretically never notch the anterior cortex of the femur. The drawback of anterior referencing is that a slightly larger bone results in collateral ligament laxity in flexion and a slightly smaller bone will result in collateral ligament tightening in flexion (flexion contracture).

Posterior referencing systems have a major advantage over anterior referencing systems in that they theoretically never develop flexion contracture. The drawback is that a slightly large femur is prone to anterior notching, which can increase the likelihood of distal femoral fractures under either impact loading or cyclic fatigue loading.

Another approach to anterior/posterior referencing is a hybrid design that allows for both anterior and posterior referencing. The positioning apparatus 510 references the posterior femoral condyles (posterior referencing), while the pattern plates 432 allow for precise referencing of the anterior femoral cortex. The anterior referencing device can be as simple as that shown in FIG. 30, wherein a referencing pin 694 is placed through the anterior-most cutting paths 436 of the pattern plates 432 to contact the anterior femoral cortex 661. The pattern plates 432 include markings S (smaller size) and L (larger size). When the pin 694 falls between the S and L marks, the pattern plates 432 are the proper size and are properly positioned for that femur. If the pin 694 falls outside the range marked by S and L towards the S side, a smaller size pattern plate should be used, and conversely, if the pin 694 falls outside the range on the L side, a larger size pattern plate should be used. Alternatively, the pattern plate 432 could be adjusted vertically via means not shown to compensate for between-size bones.

In another embodiment, the pattern plate could include a plunger assembly at the anterior end of the cutting path. The plunger could be movable vertically to contact the femur and indicate size of the femur with respect to the pattern plate in use. As such, the plunger could be incrementally marked from +4 to −4 millimeters with 0 being the proper size for the pattern plates in use. Again, the pattern plates could be sized up or down if the femur is off of the scale, or the pattern plates could be moved up or down to compensate for between size bones depending upon surgeon preference. If, for example, a bone registers a +2, anterior notching of the femur would occur. To avoid this, the pattern plates could be moved anteriorly 1 millimeter to +1. In this manner, anterior notching would be minimized and the posterior femoral condyles would only lack 1 millimeter of material, which should not be detrimental as some ligamentous laxity in flexion is acceptable because the collateral ligaments are normally slightly looser in flexion than they are in extension. It should be noted that the radii or curve in the anterior-most area of the cutting path will assure that anterior notching is easily avoidable.

Pattern Plate with Tracking Means

Figure 31:
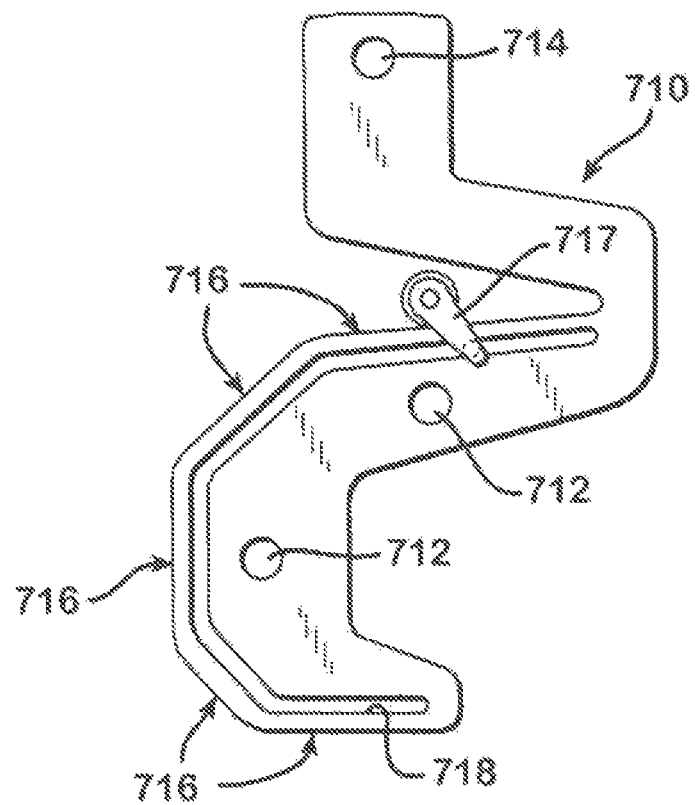
FIG. 31 is a side plan view of another embodiment of the pattern apparatus shown in FIG. 19.

Another embodiment of the pattern plates of the present invention is shown in FIG. 31. In this embodiment, the pattern plates, generally indicated at 710, basically comprise only the lower edge, or bearing surface 716 of the cutting path 436 of pattern plates 432 shown in FIGS. 19-21. Accordingly, the pattern plate 710 includes fixation apertures 712 and crossbar aperture 714. The milling apparatus bears against the bearing surface and follows the same therealong to resect the bone in accordance with the shape of the bearing surface 716. Of course, the bearing surface could be smaller or larger than the desired cut location depending on the size of the milling apparatus. The pattern plate 710 could further include a groove or guide means 718 extending in the pattern plate alongside the bearing surface and the milling apparatus could include an arm or other retaining linkage 717 extending from the handle or bushing of the milling apparatus and into the groove 718 for engagement with the groove 718 for guiding or retaining the milling apparatus along the bearing surface 716 of the pattern plate 710. Alternatively, it should be noted that the bearing surface could also comprise just the upper surface of the cutting path 436 of the pattern plates 432, as shown in FIGS. 19-21.

Ligament Balancing

Figure 32:
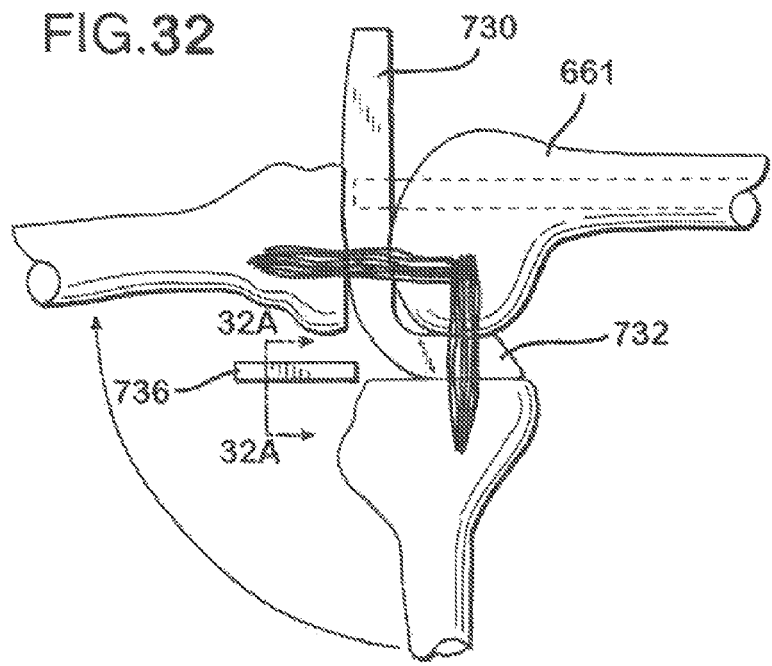
FIG. 32 is a side plan view of another embodiment of the positioning apparatus shown in FIG. 24 for use in performing ligament balancing.
Figure 32A:
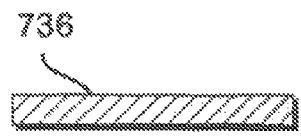
FIGS. 32A and 32B are cross-sectional views along section A-A in FIG. 32.
Figure 32B:
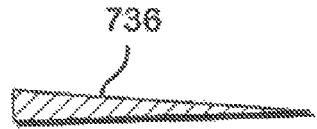

As shown in FIG. 32, an alternative embodiment of the alignment guide body 730 can be used for performing ligament balancing. The alignment guide body 730 of this embodiment can include a skid 732 formed as a part of the guide body 730, or attachable thereto. The skid 732 is of a relatively thick cross-section, approaching or equal to the cross-section of the guide body 730. The guide body 730 is attached to the femur 661 and the femur may be moved from extension to flexion and back, while the ligament tension of the collateral ligaments is reviewed. Ligamentous release can be performed to balance the ligaments. Further, shims 736, in either a rectangular cross-section (FIG. 32A) or an angled cross-section (FIG. 32B), can be used in connection with the alignment guide body 830 and skid 732. These shims could be positioned between the underside of the skid 732 and the resected tibia.

Milling Means

In a preferred embodiment of the invention, a cylindrical milling bit is used for following the cutting path described in the pattern plates for resecting a bone. Importantly, it is within the scope of the present invention to use a flat reciprocating bit, much like a hacksaw, for following the cutting paths described in the pattern plates for resecting a bone.

Further, it may be desirable to make all or some of the cuts using a cylindrical milling bit or a flat reciprocating bit having a smooth center section without cutting means. An advantage of a cutting tool without cutting means along a center portion thereof is the protection of posterior cruciate ligament during resection of the femur. Accordingly, one cutting tool could be used to make the anterior cut, the anterior chamfer, the distal cut, and the posterior chamfer, while another cutting tool, with a smooth center portion, could be used to make the posterior cut to avoid any chance of jeopardizing the posterior cruciate ligament.

Additionally, the milling bits herein described can be used with or without a guide handle as will hereinafter be described. Further, it should be pointed out that it is within the scope of the present invention to fabricate the milling bit or other cutting tool from metal as heretofore known, or to alternatively fabricate the milling bit or other cutting tool from a ceramic material. An advantage of a ceramic milling bit or cutting tool is that such resists wear and, accordingly would be a non-disposable component of the present invention which would help to reduce the cost of the system of the present invention.

Three Dimensional Shaping

Figure 33A:
FIGS. 33A and B are front plan views of an embodiment of the cutting apparatus of the present invention for cutting a bone a in curvilinear cross-sectional plane.

Initially, it should be noted that the term cutting profile the profile geometry of a mediolateral section taken normal to the cutting path through the bony surfaces created by cutting the bone. As shown in FIG. 33, in an alternate embodiment of the present invention, a milling apparatus having a three-dimensional profile, or a form cutter, can be used to shape a bone in three-dimensions. The curved profile milling bit 750, like the milling bits used in the previous embodiments of the present invention, includes cutting teeth 752 along the length thereof and spindles 754 at the ends thereof. This milling bit 730 can follow a pattern described by pattern plates and can be guided with a handle as will be hereinafter described.

Figure 35:
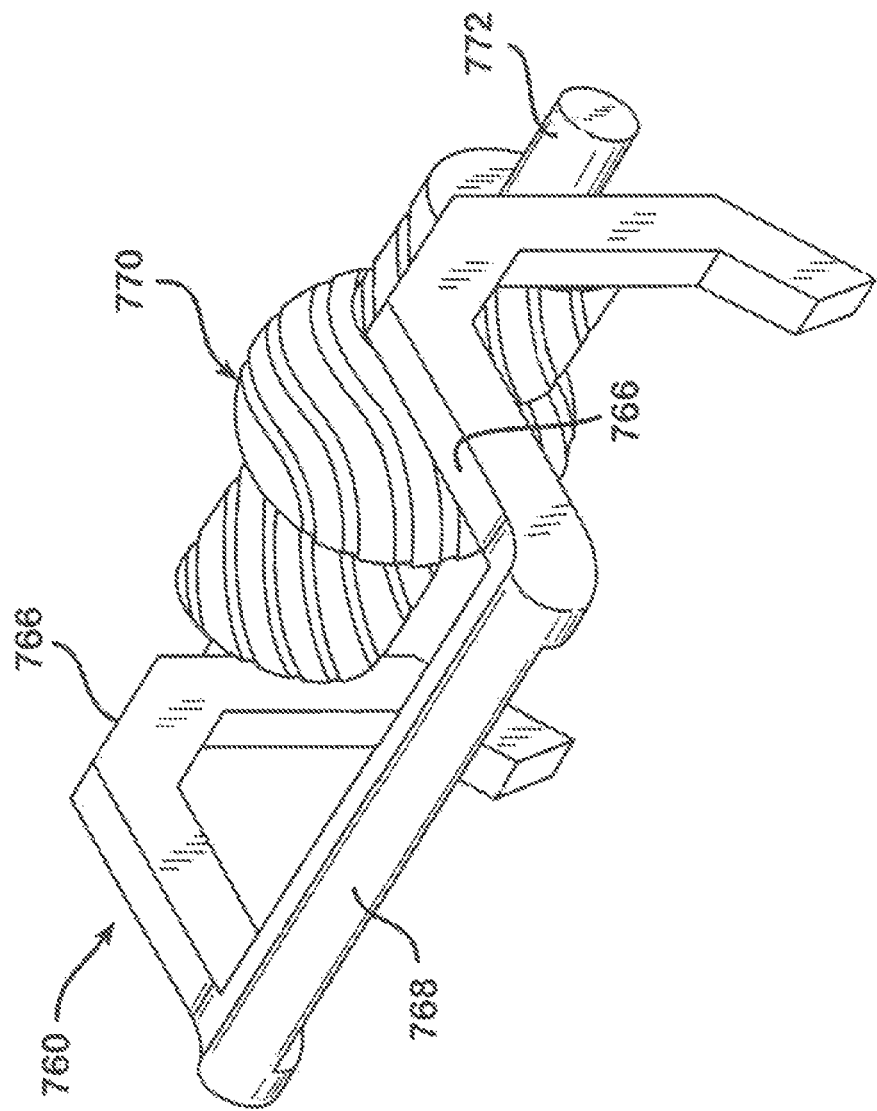
FIG. 35 is a perspective view of another embodiment of the pattern apparatus shown in FIG. 19, having a milling bit engaged therewith.

Importantly, by using a milling bit having a curved profile, one can cut a femur to resemble the natural shape of the femur, i.e., the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof, as shown in FIG. 33, or alternatively, could have one or more bulges discretely formed along the length thereof as shown in FIG. 35.

Guide Handle

Figure 34:
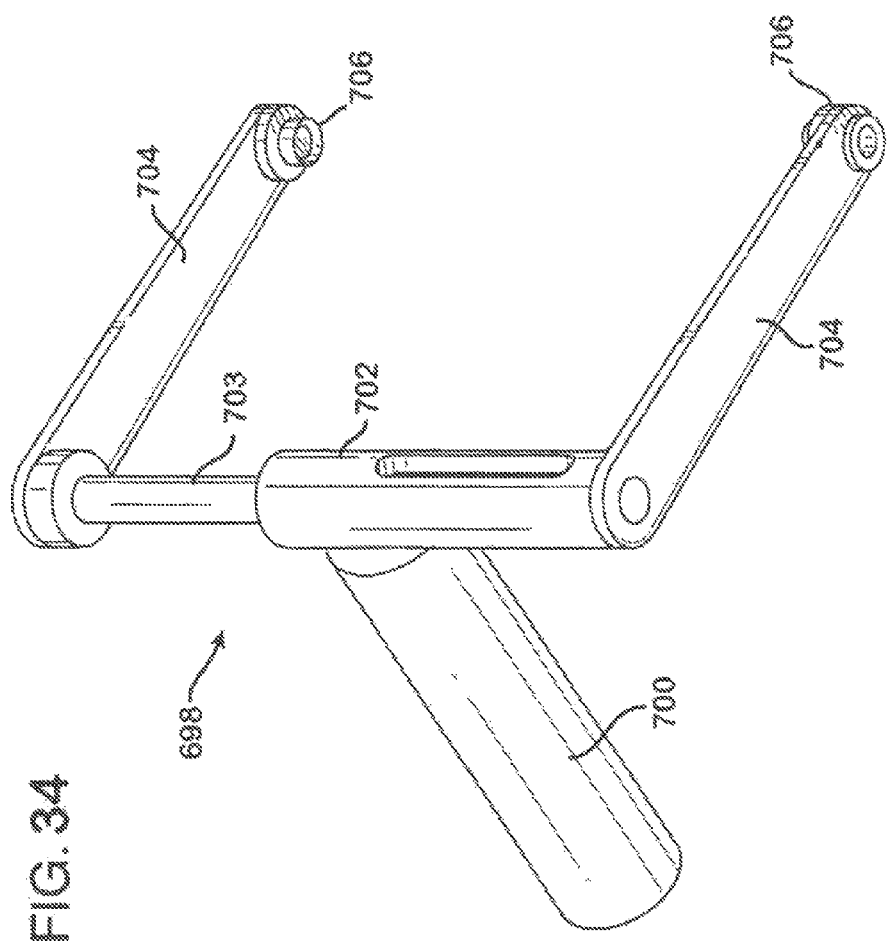
FIG. 34 is a perspective view of a handle for guiding a milling bit along a cutting path.

As shown in FIG. 34, a guide handle, generally indicated at 698 may be used to guide the milling bit along the cutting path of the pattern plate. The guide handle 698 comprises a grip portion 700 which is grasped by the user for manipulating the guide handle 698 and accordingly, the milling bit. The grip portion 700 is interconnected with a crossbar member 702 which includes a extension member 703 telescopically interconnected therewith. The crossbar member 702 and the extension member 703 may be positioned perpendicular with respect to grip portion 700. The extension member 703 is telescopically movable in and out of crossbar member 702. Means may be provided for locking the relative position of the extension with respect to the crossbar. Also, it should be noted that the grip portion may rigidly or pivotally be interconnected with the crossbar as desired.

Extending from outer ends of the crossbar 702 and the extension member 703 are sidebars 704 in facing and parallel relationship. The sidebars 704 have two ends, the first of which are interconnected with the crossbar and the extension member, and the second of which are configured to receive and capture spindles or bushings of a milling bit in spindle bushings 706. The spindle bushings are positioned in a facing relation and could include captured bushings. The captured bushings receive the spindles of a milling bit. The captured bushings are sized to be received by the cutting path in the pattern plates and co-act therewith to guide a milling bit therealong. Accordingly, after the pattern plate or plates are attached to a bone, the milling bit is placed into the cutting path. Next a milling handle 698 is positioned such the spindle bushings are aligned with the spindles of the milling bit. Next, the extension is actuated to retract into the crossbar to move the spindle bushings onto the spindles of the milling bit where they are captured. Next, the spindle bushings are positioned within the cutting path of a pattern plate or plates. If necessary, the extension and crossbar can be locked down to lock the entire apparatus. Next, the milling bit is actuated and the grip portion of the handle is grasped and manipulated to move the milling bit along the cutting path to cut a bone.

Distally Positioned Pattern Plate

Figure 36:
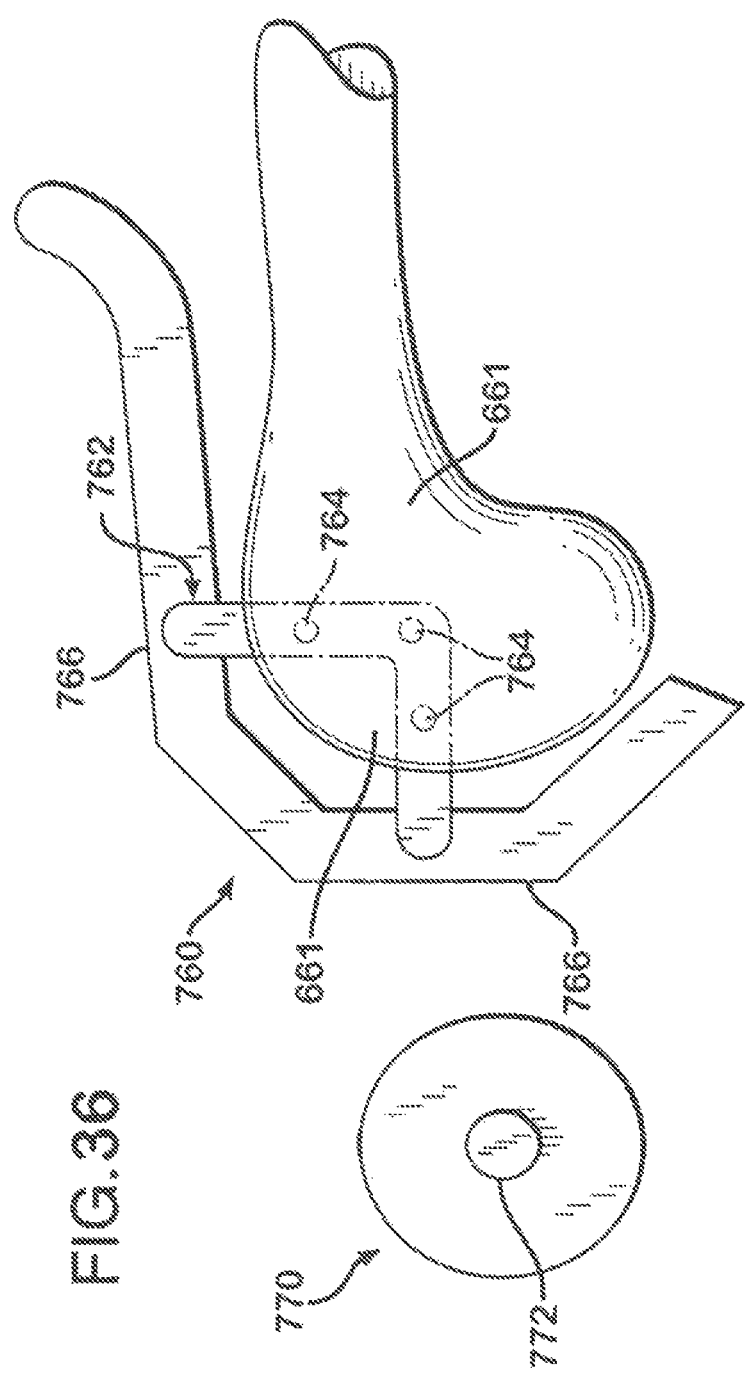
FIG. 36 is a side plan view of the pattern apparatus shown in FIG. 35 with the milling bit disengaged from the pattern apparatus.
Figure 37:
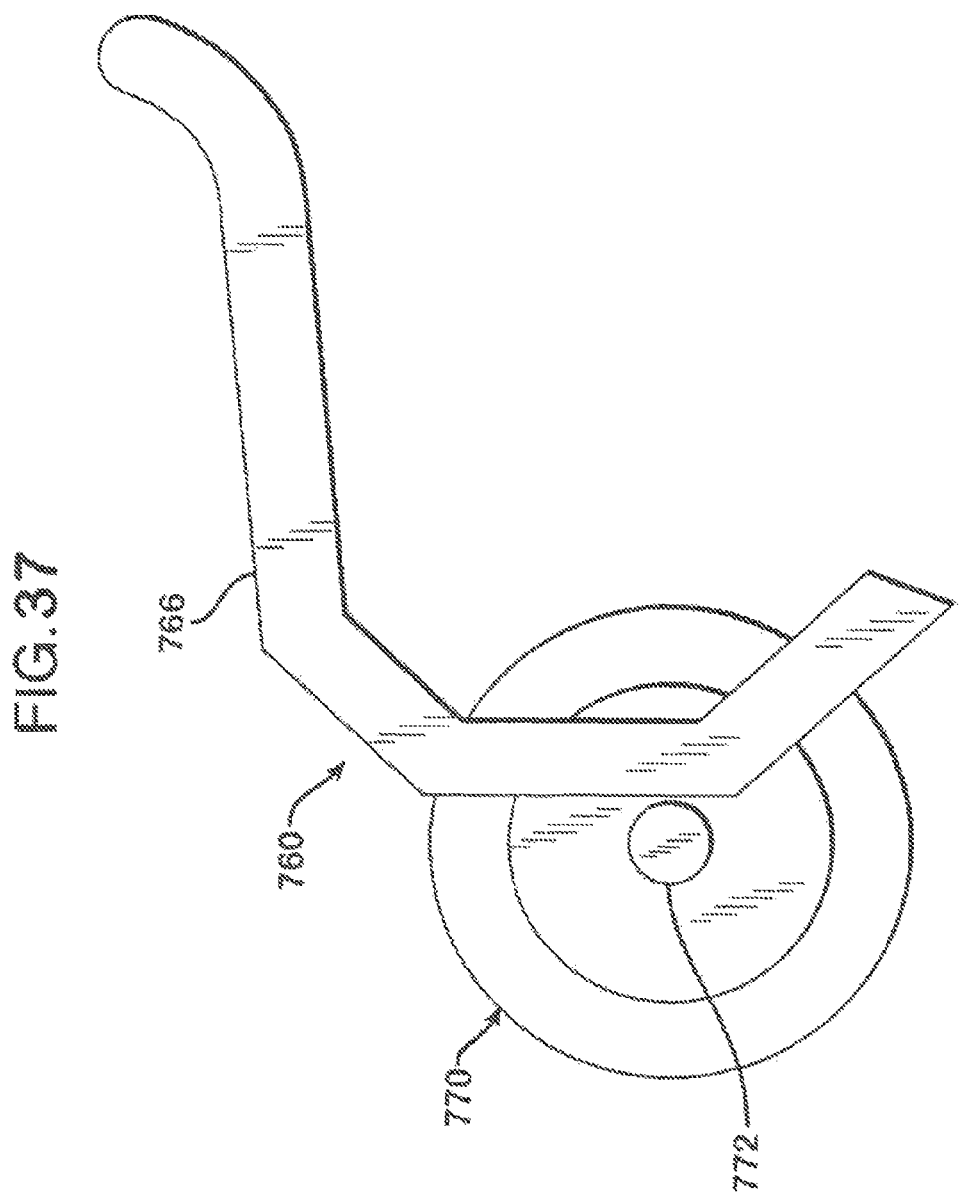
FIG. 37 is another side plan view of the pattern apparatus shown in FIG. 36 showing the milling bit engaged with the pattern apparatus.

As shown in FIGS. 35-37, in an alternate embodiment of the present invention for resecting a femur, the plates could take the form of a rail assembly, generally indicated at 760, positioned distally of the distal femur 661. The plates could be affixed to the femur by fixation arms 762, attached at one or more points to the rail assembly 760, and including fixation apertures 764 for receiving fixation screws or other fixation means for attaching the fixation arms 762, and hence the rail assembly 760, to a distal femur 661. The rail assembly 760 includes one or more guide rails 766 which match the shape of the desired resection, though the rails may be larger or smaller depending on the dimensions of the milling apparatus used and the positioning of the assembly 760 with respect to the femur. In the case that the assembly 760 includes two guide rails 766, as shown, an end rail 768 may be used to interconnect such guide rails 766. The end rail 768 could be replaced by a connection means similar to the crossbar apparatus 440, hereinbefore described. The rail assembly may be positioned on the distal femur in accordance with the teachings contained herein, or in any other manner known in the art. After alignment, according to any means disclosed herein or known or developed, and after fixation of the assembly to a femur, a milling bit 770 may be used to follow the guide rails 766 to resect the femur 661, the guide spindles 772, or bushings (not shown), of the milling bit 770, contacting and riding the guide rails 766. Importantly, the rail assembly 760 is attached to a femur and used in much the same way as the pattern plates previously described with the exception that the rail assembly can be positioned substantially distal of the femur, thereby potentially requiring less exposure and possibly resulting in less interference for placement thereof. The rail assembly 760 could further include an upper retaining rail for forming a slot or cutting path for capturing the milling bit therein. Additionally, it should be noted that any milling bit described herein could be used with rail assembly 760 including a curved profile milling bit.

Curvilinear Implants

Figure 38:
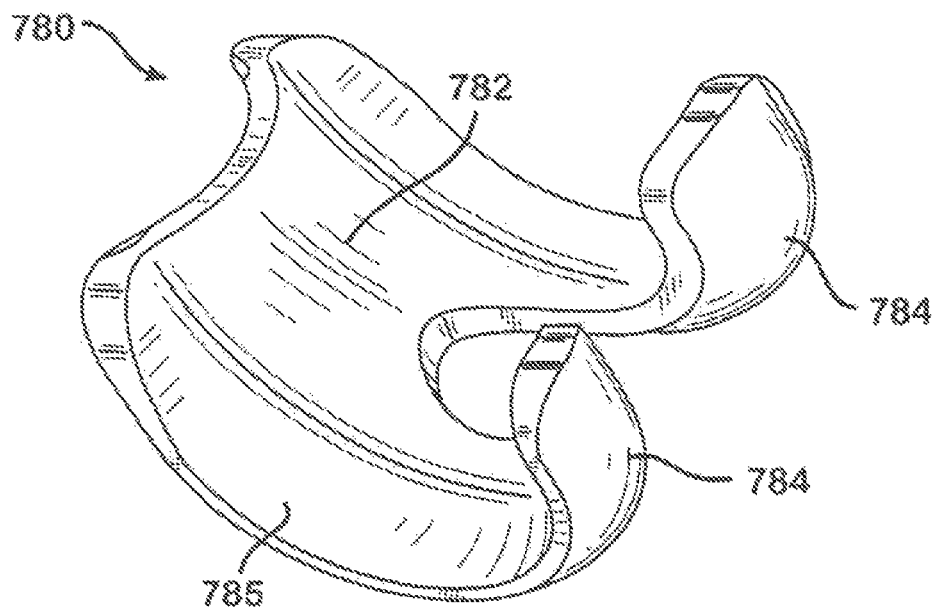
FIG. 38 is a perspective view of a femoral implant having a curved implant bearing surface.
Figure 39:
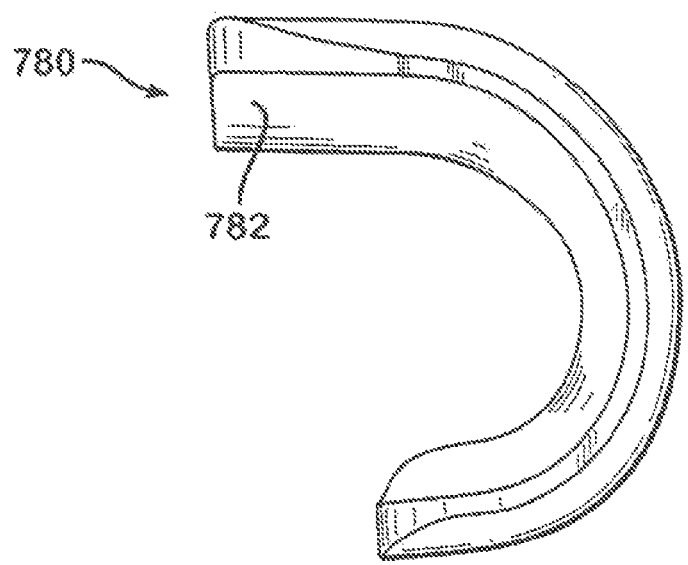
FIG. 39 is a side plan view of the femoral implant shown in FIG. 38.

As shown in FIGS. 38 and 39, an implant 780 may have curvilinear interior surfaces 782, as well as a more conventional curvilinear exterior surface. The particular example cited herein is a femoral implant used in total knee arthroplasty but the principles described herein may be applied to any application where foreign or indigenous material is affixed to an anatomic feature. The curvilinear bone surfaces necessary for proper fixation of such an implant may be generated through the use of the curvilinear milling or form cutter and the curvilinear cutting path means discussed herein. While it is possible to use multiple form cutters with differing geometries and, therefore, an implant with an internal geometry that varies along the cutting path from the anterior to the posterior of a femur, for the sake of intraoperative time savings a single form cutter is preferable.

The mediolateral cross-sectional internal geometry of such an implant, and therefore the necessary resected bony surfaces of the femur, are consistent about the cutting path in a single form cutter system. It should be noted that the implant may possess a notch between members 784 (posterior femoral implant condyles) in the areas approximately in between the distal and posterior femoral condylar areas to accommodate the posterior cruciate ligament and other factors. Because of the notch between the posterior femoral condyles it may not be necessary for the form cutter to cut any material in the notch. It may be desirable to provide outer flat surfaces 785 with an adjoining curvilinear surface 782 positioned therebetween. Other combinations of flat or curvilinear surfaces are also within the scope of the present invention.

Figure 47:
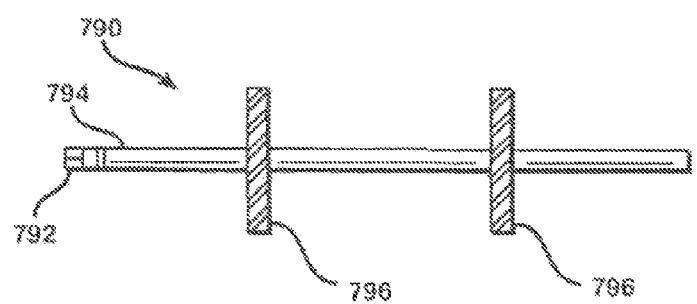
FIG. 47 is front plan view of another cutting apparatus for use in connection with the present invention.
Figure 48A:
FIG. 48 is a side plan view of the femoral implant shown in FIG. 38, FIGS. 48A, 48B, 48C, and 48D being sectional views taken along lines A-A, B-B, C-C and D-D of FIG. 48, respectively.
Figure 48B:
Figure 48C:
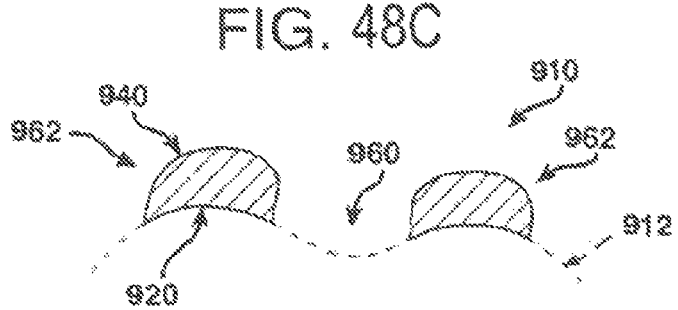
Figure 48D:
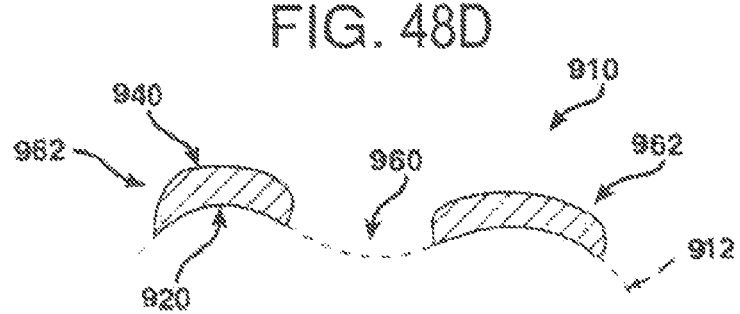

Additionally, it may be advantageous to utilize a secondary form cutter as shown in FIG. 47 for use in creating a slot or slots in or near the distal area of the femur after it has been resected. Such a secondary cutter 790 would include engagement means 792 for engagement with driving means, and a shaft 794 carrying cutters 796 for cutting slots into the femur through one or more of the resected surfaces thereof. Through the inclusion of an additional or adjunct cutting path in the pattern means, it would be advantageous to utilize the form cutter to create the aforementioned slots to accommodate the fixation fins which may be molded as an integral part of the interior surface of the implant. These fins would provide mediolateral fixation stability in addition to that provided by the trochlear groove geometry of the implant. Further, the fins also provide for additional surface area for bony contact and ingrowth to increase implant fixation both in cemented and cementless total knee arthroplasty.

There are numerous advantages to the femoral component herein described. Foremost, it will allow for the thinnest implant cross-section possible (perhaps 3 mm to 6 mm in thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e., when a cast is placed on a person's arm the muscles in that arm gradually weaken for lack of use.

Additionally, the curvilinear implant design may allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant will not only allow for the superior surface properties of ceramic, but also avoid the excessively thick cross-sections currently required for the use of the material.

This could result in a less expensive femoral implant because of the reduced amount of material needed for the implant, as well as an improved, more natural, and even stronger knee replacement. It may be desirable to vary the cross-section of the implant 780 to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces. Also, it should be pointed out that such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Patella Shaping

The apparatus for preparing a patella, as shown in FIGS. 40-42, comprises a plier-like patella resection apparatus generally indicated at 800. The patella resection apparatus 800 includes grip handles 802 for manipulating the apparatus, cross-over members 804 pivotally interconnected with each other by pin 806, and patella clamp members 808 extending from the cross-over members in parallel and facing relation. The patella clamp members 808 have beveled edges 810 for contacting and supporting a patella along the outer edges thereof. Guide member structures 812 are mounted on each of the patella clamp members 808 to form a retainer for a cutting means to follow a cutting path defined by the upper surface of the clamp members. Bushings 814 are captured within the retainer and the cutting path for receiving a cutting means 816 and guiding the cutting means 816 along the cutting path.

In preparing the patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

Bone Substitution and Shaping

Figure 43:
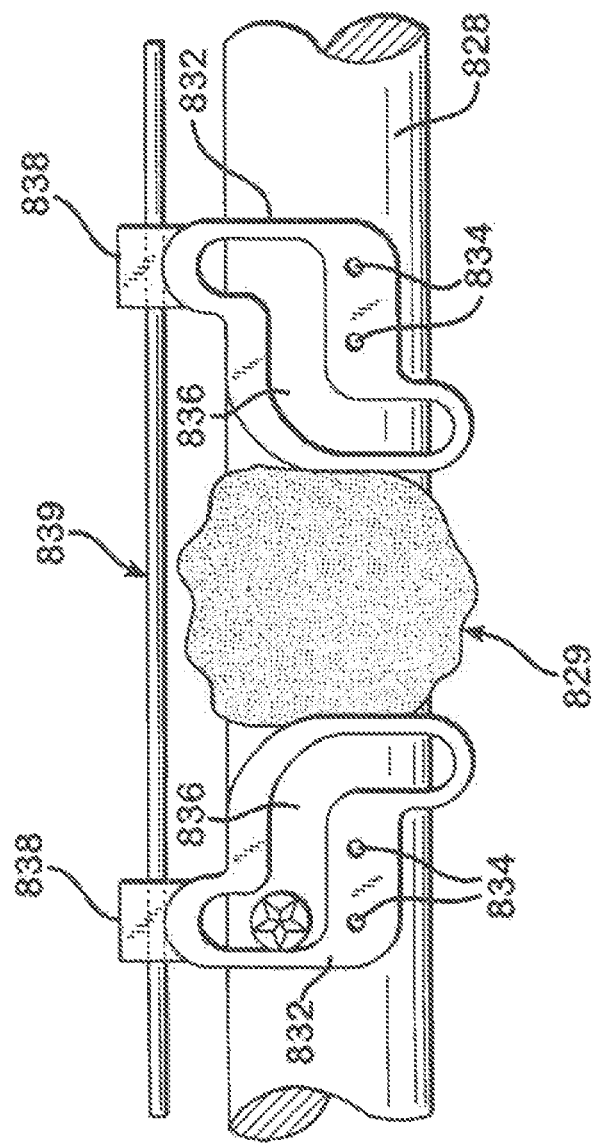
FIG. 43 is a perspective view of another embodiment of the pattern apparatus of the present invention for cutting a bone.

Referring now to FIG. 43, another embodiment of the pattern apparatus of the present invention for cutting bone is shown. This embodiment of the invention includes pattern plates 832 having cutting paths 836 described therein. The pattern plates 832 may be positioned on a bone 828 having a tumor or other pathology 829 associated therewith. The pattern plates 832 may be interconnected by crossbars 838 with opposing pattern plates (not shown) positioned on the opposite side of the bone 828. Further, each set of pattern plates 832 could be interconnected by means of positioning rod 839 extending between the crossbars 838 to maintain the relative location and orientation between the sets of pattern plates 832. The pattern plates can be positioned along the bone in accordance with what is known in the art, disclosed herein, or hereafter developed. After the pattern plates are properly positioned, they can be affixed to the bone 828 with fixation means extending through fixation apertures 834. After the pattern plates are properly located and affixed to the bone, cutting can commence by traversing a cutting means along the cutting paths 836 of the pattern plates 832. By this step, the tumor or other pathology 829 can be cut from the bone 828 and a bone graft or other surgical procedure can be implemented to repair and/or replace the bone that has been cut. The benefits of cutting a bone with the pattern plates of the present invention include providing smooth and even cuts to the bone to facilitate fixation of bone grafts or other means for repairing and/or replacing bone. Further, the same pattern plates can be used to cut another identical sized and shaped bone for grafting to the first bone to replace the cut away bone.

Alternate Positioning and Alignment Guide

Figure 44:
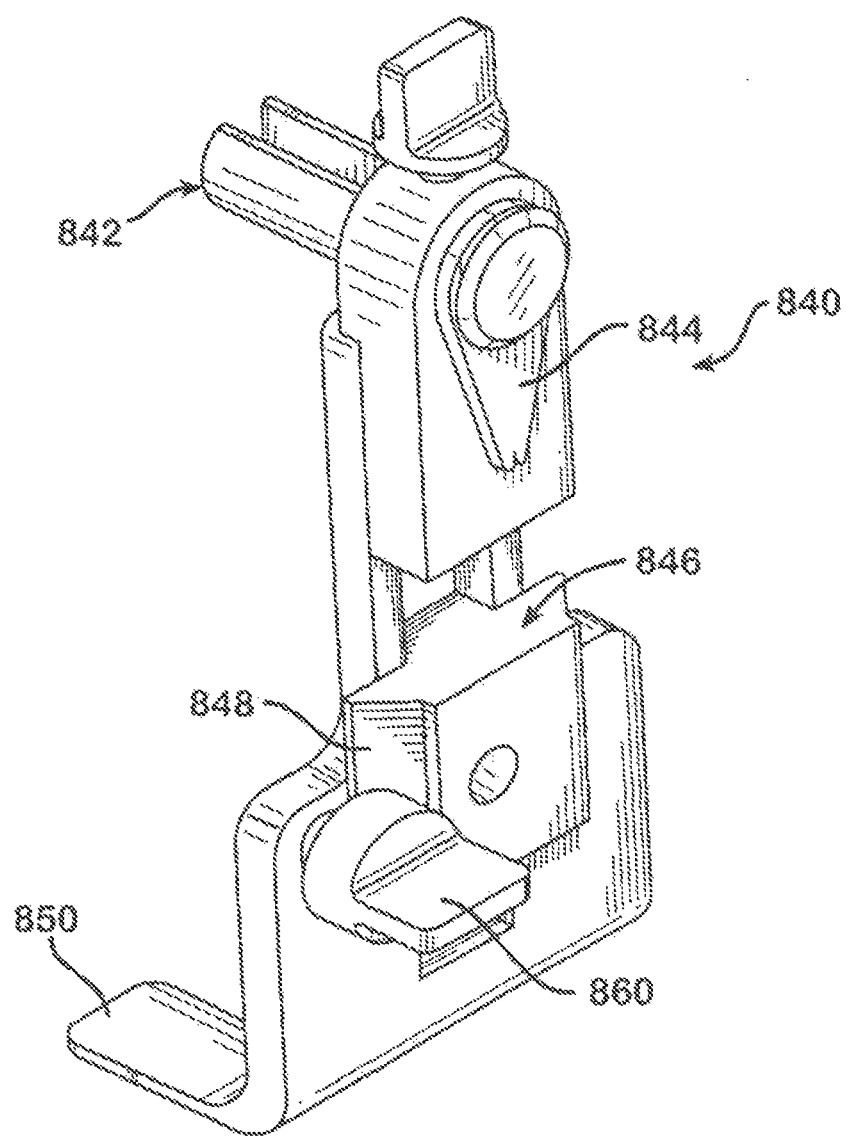
FIG. 44 is a perspective view of another embodiment of the alignment apparatus shown in FIG. 24.

An alternate positioning and alignment guide is generally indicated at 840 in FIG. 44. The positioning body 840 comprises a crossbar linkage 842 and an alignment indicator 844 at an upper end thereof for interconnecting with a crossbar to align pattern plates interconnected with such crossbar. The positioning body 840 also includes an alignment block 846 for interconnecting with an intramedullary rod in much the same manner as the IM rod guide block shown in FIG. 28. The alignment block 846 is vertically movable along the positioning body 840 and can be locked into a desired position by means of lock screw 860 which bears against a flange 848 of the alignment block 846. The positioning body 840 further includes skids 850 for contacting the posterior surface of the distal femoral condyles for referencing same.

Unicondylar and/or Single Pattern Plate Support

Figure 45:
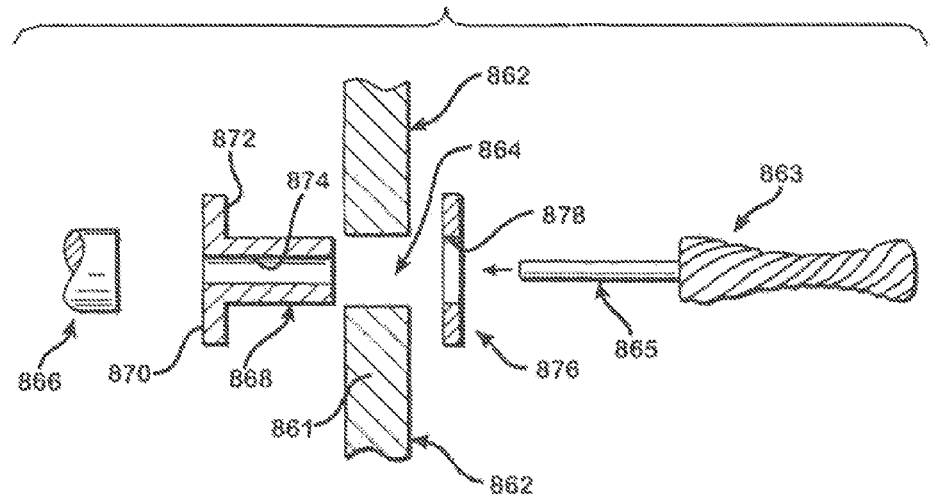
FIG. 45 is a partially exploded side plan view of another embodiment of the pattern apparatus of the present invention for cutting a bone.

As shown in FIGS. 45 and 46, one pattern plate of the present invention can be used by itself to guide a cutting means along a cutting path to cut a bone. Such an application is particularly useful for unicondylar resecting of a femur. Use of a single pattern plate 862 is facilitated by bushing 868 having an outer flange 870 with a bearing surface 872 and an internal bore 874 sized to receive a spindle 865 of a cutting tool therein. The bushing 868 is sized to fit into the cutting path 864 of the pattern plate 862, the bearing surface 872 of the flange 870 contacting the side of the pattern plate 862. Washer 876 includes a central bore 878 sized to receive the far end of the bushing 868 extending past the pattern plate 862, the washer bearing against the side of the pattern plate 862 opposite the side that the bearing surface 872 of the flange 870 of the bushing 868 bears against. Thus, the washer and the bushing co-act to form a stable link with a pattern plate. As shown in FIG. 46, this link can be fortified by means of bearing arms 880 interconnected with the bushing and the washer, or formed integrally as part thereof, which by pressure means are forced together to retain the bushing within the cutting path of the pattern plate. After the bushing is captured within the cutting path, the spindle of the cutting means can be inserted through the bushing and interconnected with means 866 for driving the cutting means. Alternatively, it should be pointed out that when using a single pattern plate to cut a bone, it may be desirable to support the cutting means at the pattern plate and also at the other end thereof. One could effect such desired support at the other end of the cutting means by a brace or other linkage interconnecting the other end of the cutting means with a secondary support or anchor means positioned on the opposite side of the bone or at another location.

Revisions

Conventional revisions require removal of the old implant and the referencing of uncertain landmarks. Revisions, by means of the present invention, allow for reference of the implant while it is still on the bone. One can obtain varus/valgus referencing, distal resection depth, posterior resection depth, and rotational alignment by referencing the geometry of the implant with the alignment guide. An extramedullary alignment rod can be used to facilitate flexion/extension alignment. The fixation screws can then be advanced to touch the bone and mark their location by passing standard drill bits or pins through the cannulations in the fixation screws and into the bone. Then, the pattern and guide device are removed, the old implant removed, and the pattern device repositioned by means of the marked location of the fixation screws and then fixed into place. Accordingly, the cuts for the new implant, and thus the new implant itself, are located and orientated based off of the old implant. This results in increased precision and awareness of the final implant location and orientation as well as potential intraoperative time savings.

The particular example of the present invention discussed herein relates to a prosthetic implant for attachment to a femur in the context of total knee arthroplasty, i.e., a femoral implant. However, it should be pointed out that the principles described herein may be applied to any other applications where foreign or indigenous material is affixed to any other anatomic feature.

As shown generally in FIGS. 38 and 48, the implant apparatus of the present invention, generally indicated at 910, comprises curvilinear interior fixation surface 920 as well as curvilinear exterior bearing surface 940. Importantly, the implant of the present invention includes curvilinear surfaces extending from an anterior to a posterior area of the femur and/or implant, as is conventionally known, as well as curvilinear surfaces extending from a medial to a lateral area of the femur and/or implant to approximate the shape of natural femur. In other words, the fixation path (i.e., corresponding to the cutting path along which the milling bit rides to resect the femur; indicated by arrow A in FIG. 38) as well as the fixation profile (as one proceeds along the cutting profile orthogonally to the cutting path; indicated by arrow B in FIG. 38) are both predominantly curvilinear. As such, the cutting profile (arrow B) of the interior fixation surface 920 could include a curved or flat area 922 and another curved or flat area 924 therebetween. Preferably, the outer areas 922 are flat or relatively flat and the inner area 924 is curved to approximate the shape of a natural distal femur 912. It should be pointed out that the outer areas 922 could be curved and the inner area 924 could also be curved, but embodying differing radii of curvature. Additionally, it should be pointed out that the geometry of the internal fixation surface 920 of the implant 910 could be varied as desired. As such, any combination of flat surfaces and curvilinear surfaces could be used. As shown in FIG. 48, and in more detail in FIGS. 48A, 48B, 48C, and 48D, the cross-sectional thickness and mediolateral width of the implant of the present invention could vary along the implant 910. This variance results from merging a cutting tool to cut a bone, i.e., the implant 910 closely resembles in size and shape the material removed from the bone. Accordingly, the cut starts as a point 925 and grows in depth and width.

The curvilinear bone surfaces necessary for proper fixation of such an implant 910 may be generated through the use of the curvilinear milling bit or form cutter and the curvilinear cutting path means discussed in the previous related applications set forth herein, the entire disclosures of which are expressly incorporated herein by reference. Basically, the milling bit has a profile resulting in form cutter configuration which is concentric about its longitudinal axis to effect a curvilinear cutting profile for receiving the implant of the present invention. One embodiment of such a form cutter is shown in FIGS. 35 and 49. While it is possible to use multiple form cutters with differing geometries and therefore an implant 910 with an internal geometry that varies along the cutting path from the anterior to the posterior of a femur, for the sake of intraoperative time savings, a single anatomically optimal form cutter is preferable.

The form cutter shown in FIGS. 35 and 49 comprises a cutting guide 950 having cutting paths 952 interconnected by member 954. A milling bit 960 having cylindrical milling areas 962 at the ends and a curved milling area 964 at the center could be used. Of course, the milling areas carry cutting teeth. Spindles 961 interconnected at each end of the milling bit 960 could engage and ride the cutting path 952 of the cutting guide 950. The milling bit 960 is then guided along the cutting path 952 by means of a handle. Importantly, the shape of the milling bit 960 could be varied as desired to create a resection having a desired cutting path as well as a desired cutting profile.

The mediolateral cross-sectional internal geometry of such an implant 910, and therefore the necessary resected bony surfaces of the femur, are consistent about the cutting path in a single form cutter system. It should be noted that the implant 910 may possess a notch 970 between members 972 (posterior femoral implant condyles) in the areas approximately between the distal and posterior femoral condylar areas to accommodate the posterior cruciate ligament, as well as for other reasons. Because of the notch 970 between the posterior femoral condyles, the form cutter may not cut any material in the notch 970.

Additionally, it may be advantageous to utilize a secondary form cutter as shown in FIG. 47 for use in creating a slot or slots in or near the distal area of the femur before or after it has been resected. Such a secondary cutter 790 would include engagement means 792 for engagement with driving means, and a shaft 794 carrying one or more cutters 796 for cutting slots into the femur through one or more of the resected surfaces thereof.

Figure 50:
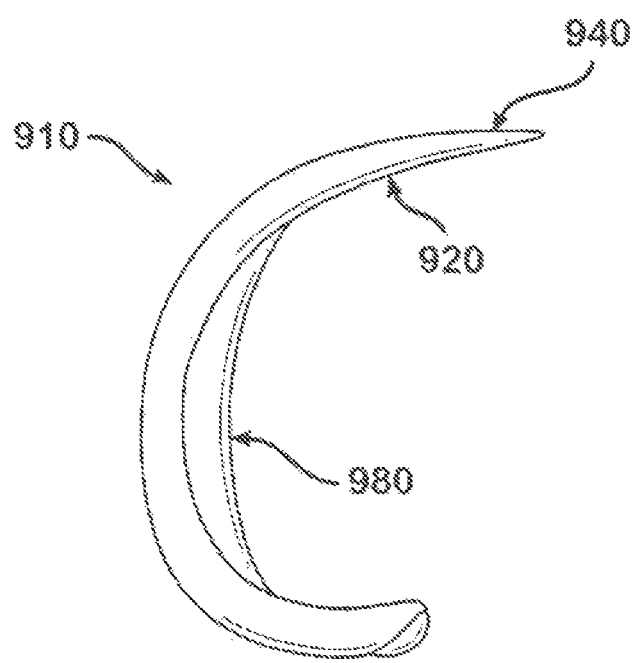
FIG. 50 is a side plan view of another embodiment of the femoral implant shown in FIG. 38.

Through the inclusion of an additional or adjunct cutting path in the pattern means, it would be advantageous to utilize the form cutter to create the aforementioned slots in the distal femur to accommodate the fixation fins which may be molded as an integral part of the interior surface of the implant 910. An implant with fixation fins is shown in FIG. 50. The fins 980 would provide mediolateral fixation stability in addition to that provided by the trochlear groove geometry of the implant 910. Further, the fins also provide for additional surface area for bony contact and ingrowth to increase implant fixation both in cemented and cementless total knee arthroplasty.

Figure 33B:
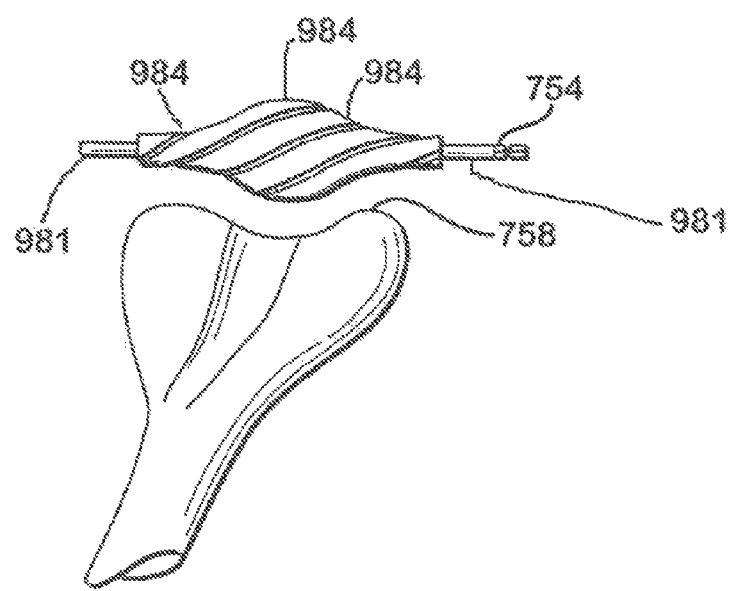

FIG. 33b shows another embodiment of a milling bit, generally indicated at 754 for creating a curvilinear cutting path and curvilinear cutting profile in femur 756. In this embodiment, the transition from a first cutting area 984 to a second cutting area 986 is continuous and smooth. This milling bit 754 also includes spindles 981 at the ends thereof for engagement with pattern means to guide the milling bit along a cutting path.

There are numerous advantages to the femoral component herein described. Foremost, it will allow for the thinnest implant cross-section possible (perhaps 3 mm to 6 mm in nominal thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint.

In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. The implant could have a relatively consistent cross-sectional thickness throughout the implant, or it could be varied as desired.

The curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e., when a cast is placed on a person's arm the muscles in that arm gradually weaken for lack of use.

Further, the curvilinear implant of the present invention could allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant would not only allow for the superior surface properties of ceramic, but also avoid the excessively thick cross-sections currently required for the use of the material.

The curvilinear implant of the present invention could result in a less expensive femoral implant because of the reduced amount of material needed for the implant, as well as an improved, more natural, and even stronger knee replacement. It may desirable to vary the cross-section of the implant to assist in seating the implant, to increase the joint kinematics and to increase the strength and fit of the implant. The implant of the present invention could be fabricated of metal, plastic, or ceramic or any other material or combination thereof. Further, the thickness of the implants and the material required to fabricate the implant could be reduced as the implants are adapted to increasingly curvilinear surfaces. Also, it should be pointed out that such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Importantly, by using a milling bit having a curved profile, one can cut a femur to resemble the natural shape of the femur, i.e., the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof, as shown in FIGS. 35 and 49, or alternatively, could have one or more bulges discretely formed along the length thereof.

FIGS. 51-60

Figure 51:
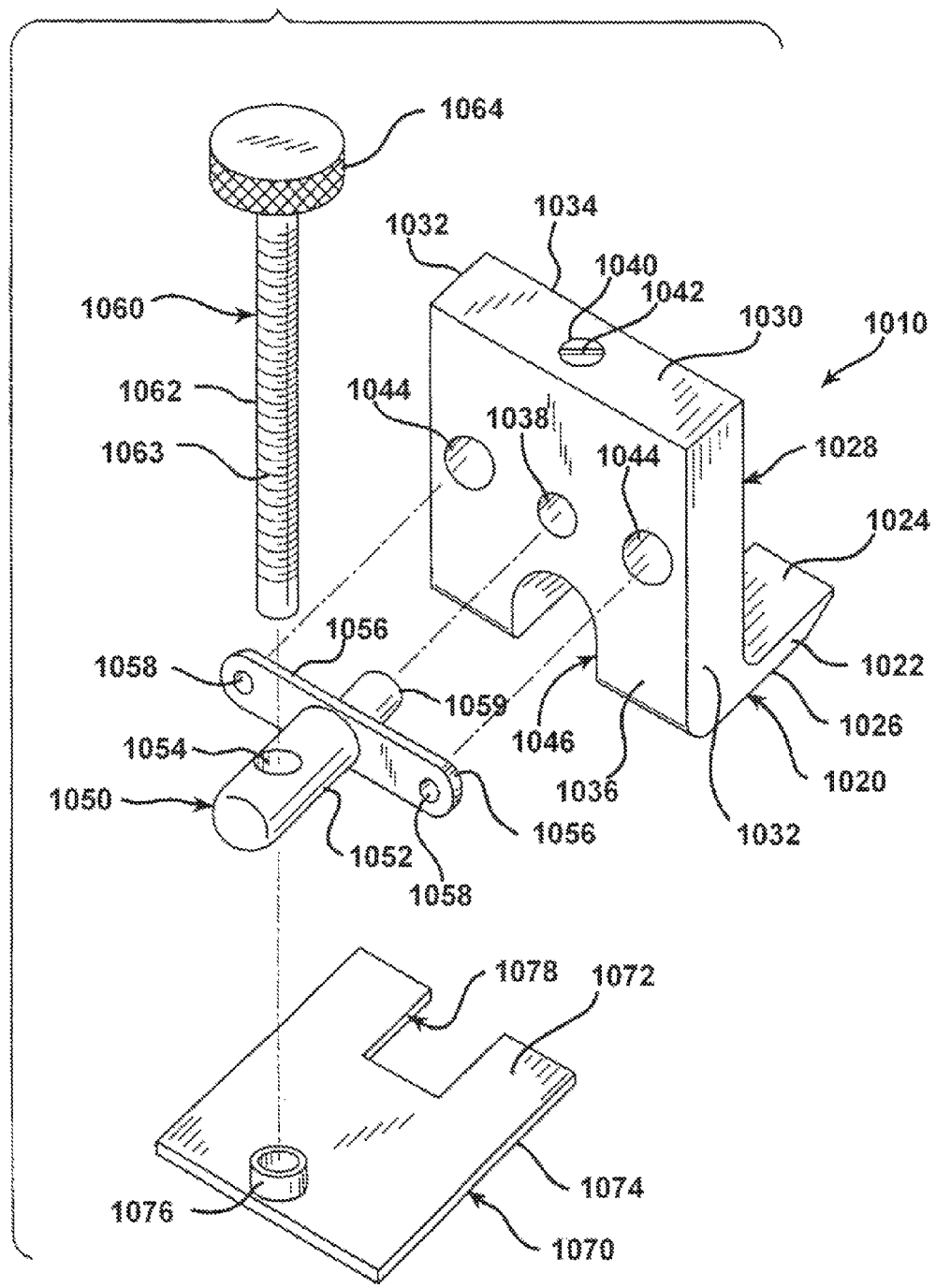
FIG. 51 is an exploded view of the femoral resection alignment apparatus of the present invention showing the guide body component, a rotating arm component, an extension rod component, and a tibial referencing component.
Figure 52:
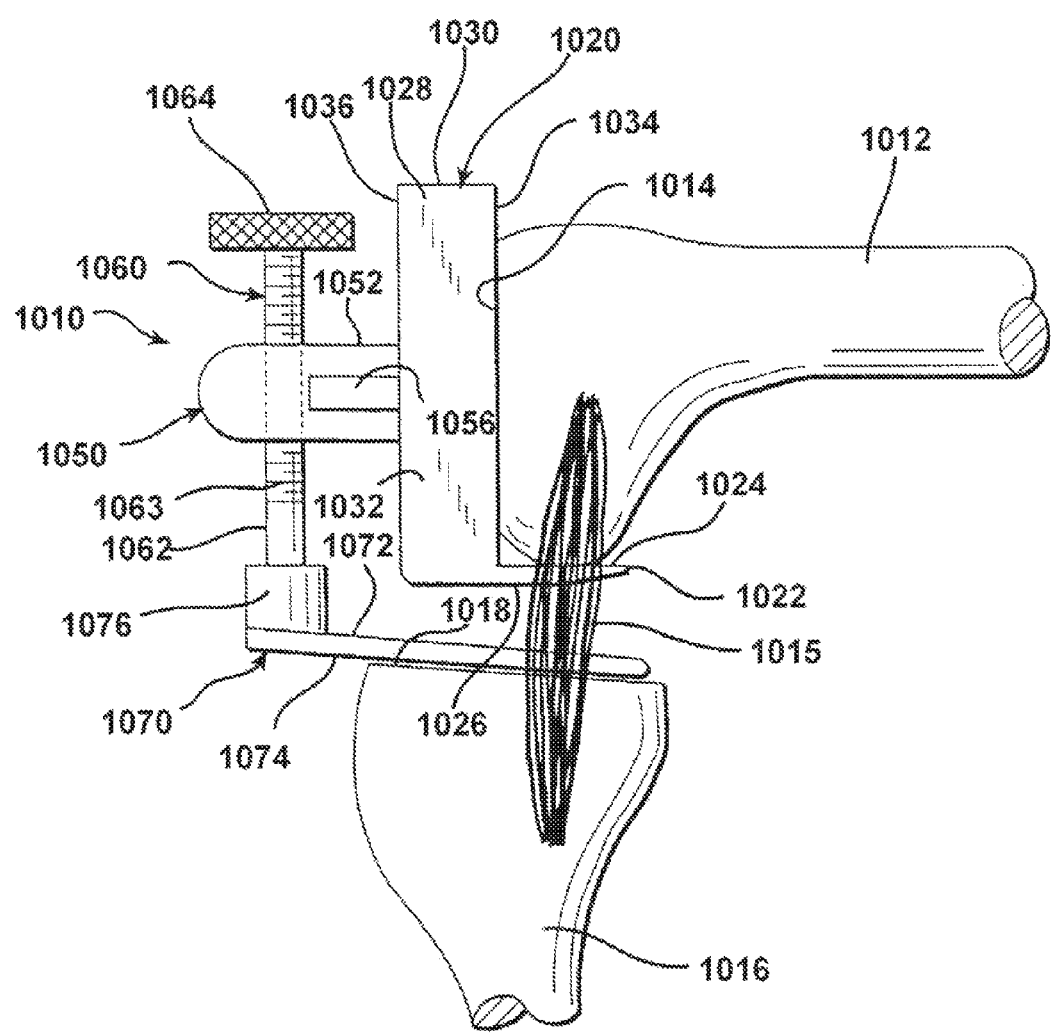
FIG. 52 is a side plan view of the apparatus shown in FIG. 51 attached to a flexed human knee joint including a distal femur, a resected proximal tibia, and collateral ligaments.
Figure 53:
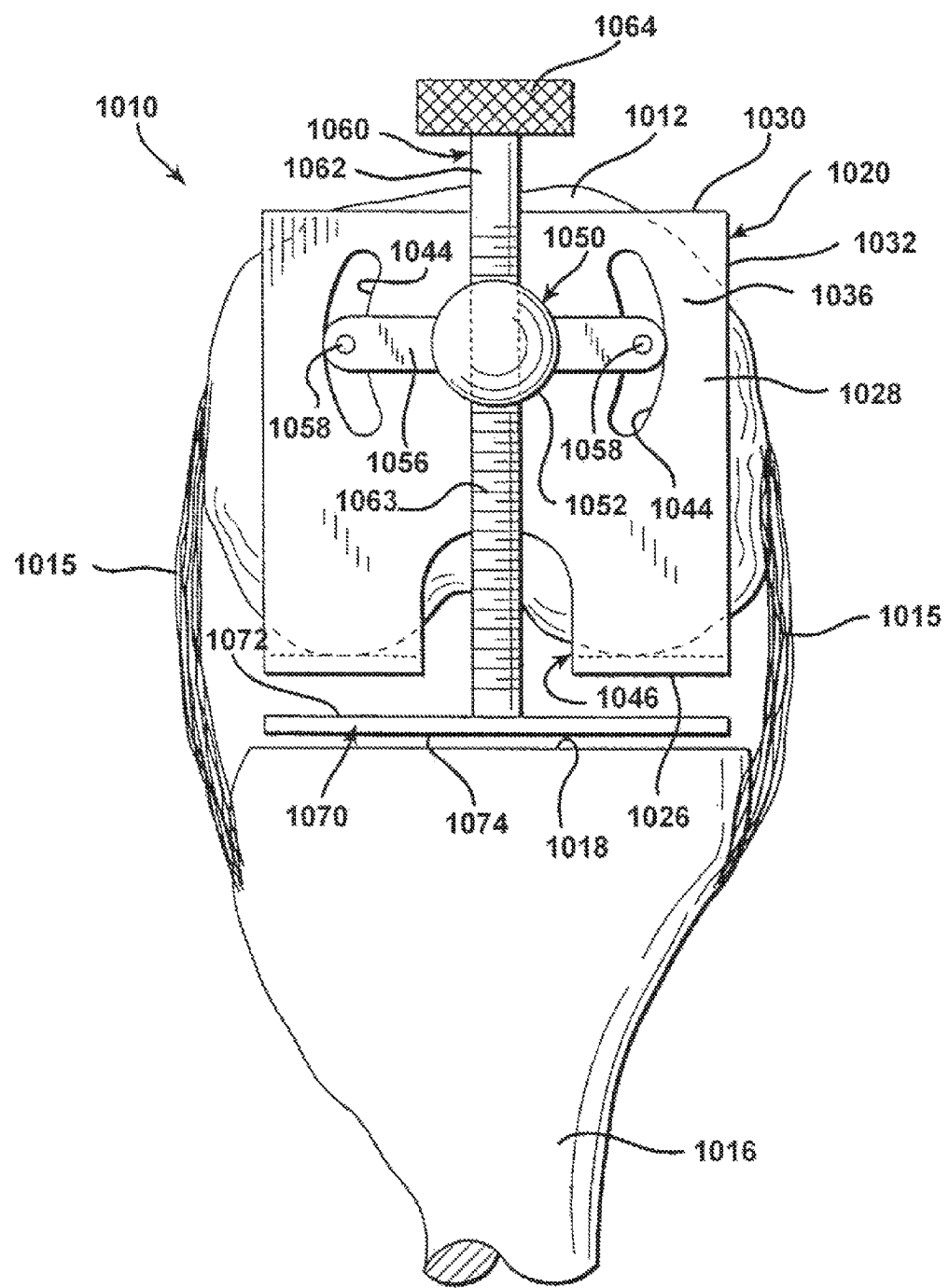
FIG. 53 is a front plan view of the apparatus shown in FIG. 51 attached to a flexed human knee joint including the distal femur, the partially resected proximal tibia, and the collateral ligaments.

Shown in FIGS. 51, 52 and 53 is the femoral resection alignment apparatus of the present invention, generally indicated at 1010. The femoral resection alignment apparatus 1010 includes a guide body component generally indicated at 1020, a rotating arm component generally indicated at 1050, an extension rod component generally indicated at 1060, and a tibia referencing component generally indicated at 1070. These components cooperate to properly locate and orient drill holes 1080 on the distal femur for attaching a cutting guide device, not shown, for resecting the distal femur. As will be described, the cutting guide employed may be one conventionally known in the art or the one described in copending U.S. patent application Ser. No. 08/300,379, filed Sep. 2, 1994, the entire disclosure of which is incorporated herein by reference.

As shown in FIG. 51, the guide body component generally indicated at 1020 includes a guide body generally indicated at 1028 having tongues 1022 extending from a lower end thereof. The tongues 1022 include an upper surface 1024 for contacting and distracting the distal femur with respect to the proximal tibia as hereinafter described. The tongues also include a lower surface 1026.

The guide body 1028 includes top surface 1030, sides 1032, front surface 1034, and rear surface 1036. Extending through the guide body 1028 from the front 1034 towards the rear 1036 is rotating arm aperture 1038. The rotating arm aperture 1038 is positioned generally in the center of guide body 1028, and accepts the rotating arm component as hereinafter described. A rotating arm lock aperture 1040 extends from the top 1030 of the guide body 1028 to the rotating arm aperture 1038 and rotating arm lock screw 1042 is threadibly engagable therewith. The rotating arm lock screw 1042 may be turned down through the guide body 1028 to contact the rotating arm component 1050 and lock the rotating arm component 1050 into a desired position.

Flanking the rotating arm aperture 1038 are drill hole apertures 1044 which may be any desired shape and which extend through guide body 1028 from the front 1034 to the rear 1036. The guide body 1028 also includes a body spacing aperture 1046 extending into the guide body 1028 from a lower end thereof, and positioned central to the width of the guide body 1028, typically between the parallel tongues 1024. The spacing aperture 1046 prevents interference between the guide body 1028 and posterior cruciate ligament and/or the tibia eminence during use.

Rotating arm component, generally indicated at 1050, includes a cylindrical body 1052 having an extension rod aperture 1054 extending therethrough to receive extension rod component generally indicated at 1060. Extending outwardly from the cylindrical body 1052 of rotating arm component 1050 are arms 1056 having drill screw apertures 1058 positioned at outer ends thereof. Additionally, extending from the cylindrical body 1052 is arm attachment shaft 1059 which is sized to be received in the rotating arm aperture 1038 in guide body 1028. Arm attachment shaft 1059 may be rotated within rotating arm aperture 1038 of guide body 1028 and when in a desired position, can be locked into such position by tightening down rotating arm lock screw 1042 to contact the arm attachment shaft 1059 within the rotating arm aperture 1038 of guide body 1028.

An extension rod component, generally indicated at 1060, includes a rod shaft 1062 having threads 1063 formed thereon. The extension rod component 1060 also includes a rod handle 1064 at an upper end of the rod shaft 1062. The rod shaft 1062 extends through the extension rod aperture 1054 in rotating arm component 1050 and is threadibly engaged therewith. Rotation of the extension rod component 1060 by rotating the rod handle 1064 causes the rotating arm component 1050 to travel up or down the rod shaft 1062 in accordance with the direction of rotation of the extension rod component 1060.

The tibia referencing component, generally indicated at 1070, includes an upper surface 1072, a lower surface 1074, an extension rod attachment means 1076 and a spacing channel 1078. The tibia referencing component 1070 is interconnected with the extension rod component 1060 by receiving a lower end of the rod shaft 1062, opposite the rod handle 1064, in the extension rod attachment means 1076. Preferably, the extension rod attachment means 1076 interconnects the rod shaft 1062 with the tibia referencing component 1070 and permits the rod shaft 1062 to be freely rotated therein.

As seen in FIG. 52, in its operative position, the femoral resection alignment device 1010 is positioned within the knee joint in flexion between the resected surface 1018 of tibia 1016 and the resected surface 1014 of the femur 1012. The lower surface 1074 of the tibia referencing component 1070 contacts the resected proximal surface 1018 of the tibia 1016. The extension rod component 1060 extends up from the tibia referencing component 1070, the rod shaft 1062 interconnected with the extension rod attachment means 1076 which holds the rod shaft 1062 perpendicular to the tibia referencing component 1070. Riding on the rod shaft 1062 is rotating arm component 1050.

The arm attachment shaft 1059 of the rotating arm component 1050 is received by the guide body 1028 through the rotating arm aperture 1038, as shown in FIG. 51. The front 1034 of the guide body 1028 contacts the resected surface 1014 of the femur 1012 and is firmly attached thereto. The tongues 1022 extending from the guide body 1028 are positioned below the posterior condyles of the femur 1012 and the upper surfaces 1024 of the tongues 1022 contact the posterior condyles of the femur 1012.

In operation, the tibia referencing component 1070 contacts the resected proximal surface 1018 of the tibia 1016 and the extension rod component 1060 is actuated to lift the rotating arm component 1050 and accordingly, the guide body 1028 and the tongues 1022 to distract the femur 1012 with respect to the tibia 1016. The collateral ligaments 1015 are accordingly drawn up to a tensioned position.

As best shown in FIG. 53, after the femur 1012 is distracted with respect to the tibia 1016, it can be seen that the arms 1056 extending from the rotating arm component 1050 are positioned parallel to the tibia referencing component 1070. Thus, an imaginary line extending through drill screw apertures 1058 in arms 1056 is parallel to the tibia referencing component 1070. After the femur is properly distracted from the tibia, the rotating arm component 1050 may be fixed with respect to the guide body 1028 by screwing the rotating arm lock screw 1042 against the arm attachment shaft 1059 of the rotating arm component 50, as shown in FIG. 51. Thereafter, any conventional drill may be extended through the drill screw apertures 1058 in arms 1056 to drill holes into the distal femur 1012. Accordingly, an imaginary line through the drill holes in the distal femur 1012 are parallel to the tibia referencing component 1070 and hence to the resected surface 1018 of the tibia 1016. Thereafter, the femoral resection apparatus 1010 can be removed from its position.

Figure 54:
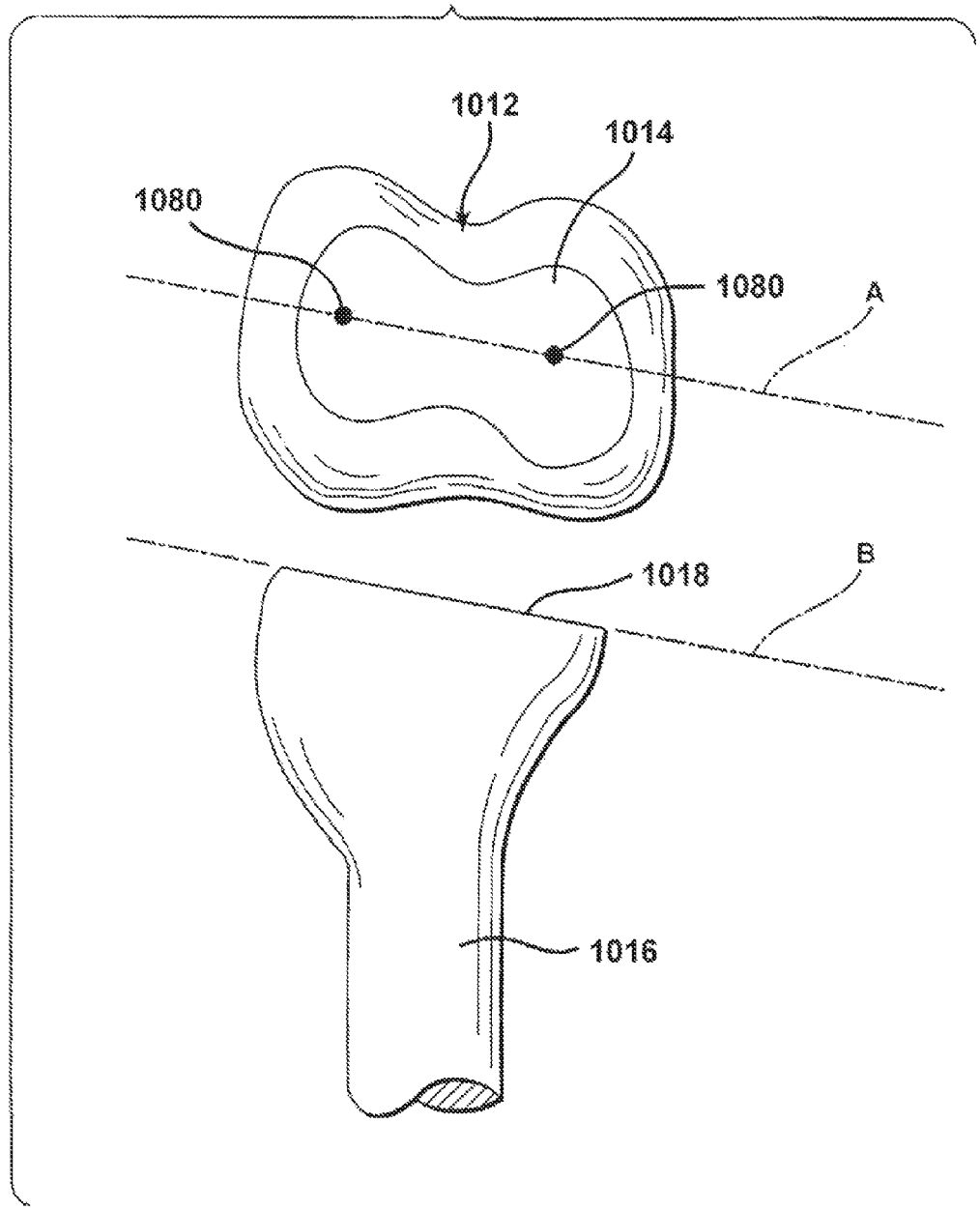
FIG. 54 is an exaggerated front plan view of a partially resected distal femur and a resected proximal tibia after use of the apparatus of the present invention shown in FIG. 1 showing placement of drill holes for attaching a cutting guide to allow for indirect control of the orientation and location of a conventional cutting guide.

As shown in FIG. 54, the drill holes 1080 in the femur 1012 are positioned along an imaginary line A. Imaginary line A is parallel to imaginary line B that extends along the resected surface 1018 of the tibia 1016. Accordingly, the drill holes 1080 in the femur 1012 are properly oriented based on the orientation of the resected surface 1018 of the tibia 1016. Additionally, because the femoral resection alignment device has been used to distract the femur 1012 with respect to the tibia 1016, the drill holes 1080 are properly located on the femur.

Thereafter, a conventional cutting guide device, not shown, can be attached to the femur using drill holes 1080 for receiving attachment means to attach the cutting guide device at a proper location and orientation of the femur. Then, means for resecting the femur, as known in the art, can be used to resect the femur. Because the drill holes 1080 are properly located and oriented on the femur, and thus the cutting guide device is also properly located and oriented, the resected femur surfaces will likewise be properly located and oriented.

Figure 55:
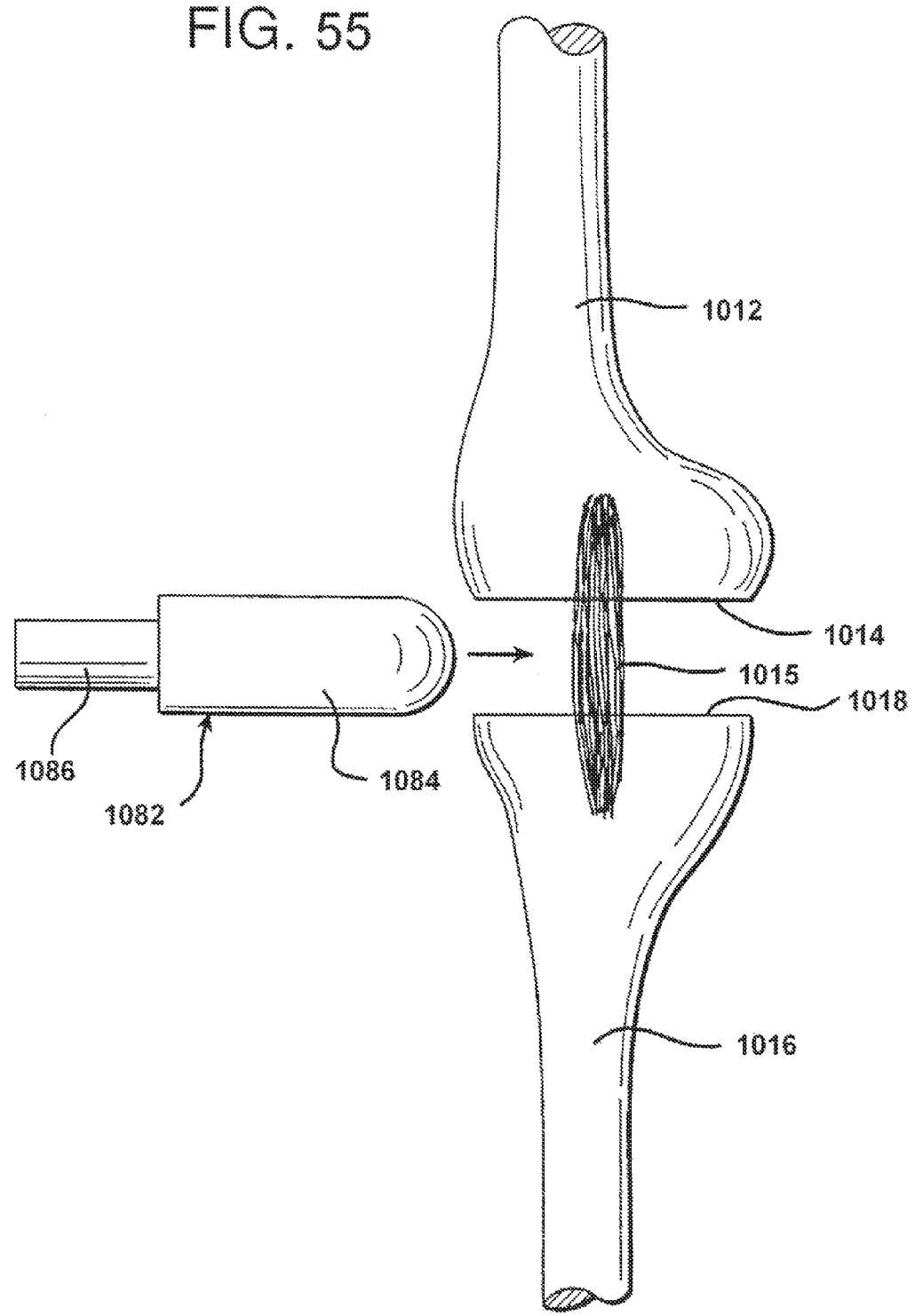
FIG. 55 is a side plan view of the extension block component of the present invention for placement between the partially resected distal femur and the resected proximal tibia by use of the apparatus of FIG. 51.
Figure 56:
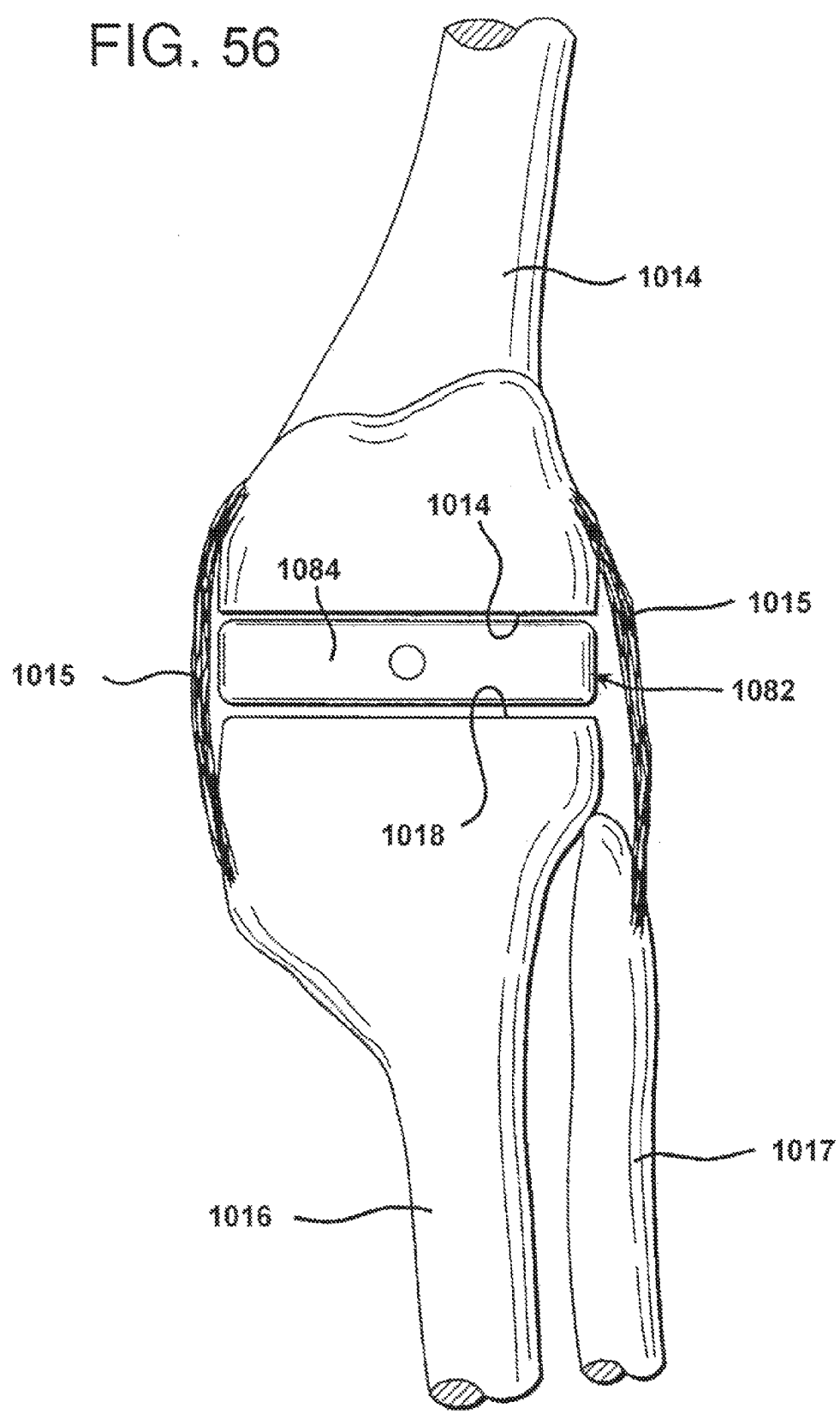
FIG. 56 is a front plan view of the extension block shown in FIG. 55 placed between the partially resected distal femur and the resected proximal tibia by use of the apparatus of FIG. 51.

As shown in FIGS. 55 and 56, the extension block component, generally indicated at 1082, includes an extension block body 1084 and handle 1086. Prior to utilizing the femoral resection alignment device to properly locate and orient the drill holes in the femur, the leg is put into extension and the extension block component 1082 is inserted between the resected surfaces 1014 and 1018 of the femur 1012 and tibia 1016 respectively. The extension block body 1084 comes in various sizes. A typical block may be seventeen millimeters thick. The extension block component 1082, when in place between the tibia and femur, facilitates ligamentous release of collateral ligaments 1015 extending between the femur 1012 and tibia 1016 on one side and the femur 1012 and fibula 1017 on the other side to provide even tension on both sides of the knee joint.

The method of using the femoral resection alignment apparatus of the present invention comprises the steps of: resecting the proximal tibia; moving the leg into extension; inserting the extension block component between the resected proximal tibia and the femur (which may or may not be partially resected); performing ligamentous release of collateral ligaments to provide even tension of the collateral ligaments on both sides of the knee joint; placing the leg into flexion; contacting the lower surface of the tibia referencing component against the resected tibia; contacting the upper surface of the the tongue of the guide body against the posterior condyles of the femur; distracting the femur from the tibia by actuating the rod shaft of the extension rod component to move the rotating arm component and hence the guide body vertically away from the tibia until the collateral ligaments are tensioned; fixedly attaching the guide body to the femur; drilling drill holes into the femur through drill screw apertures in the arms of the rotating arm component; removing the femoral resection alignment apparatus; and attaching a cutting guide device to the femur through the drill holes.

The femoral resection alignment method and apparatus is intended to work with a conventional femur resection system by ensuring that the drill holes that are placed on the face of the distal femoral resection are parallel to the proximal tibial resection when the collateral ligaments are balanced. Since the drill holes dictate the location and orientation of the cutting blocks, this device ensures that the rotating alignment of the distal femoral resections and therefore, the rotating alignment of the distal femoral prosthesis, is the same as the proximal tibial resection when the collateral ligaments are "balanced" (under equal tension).

Figure 57:
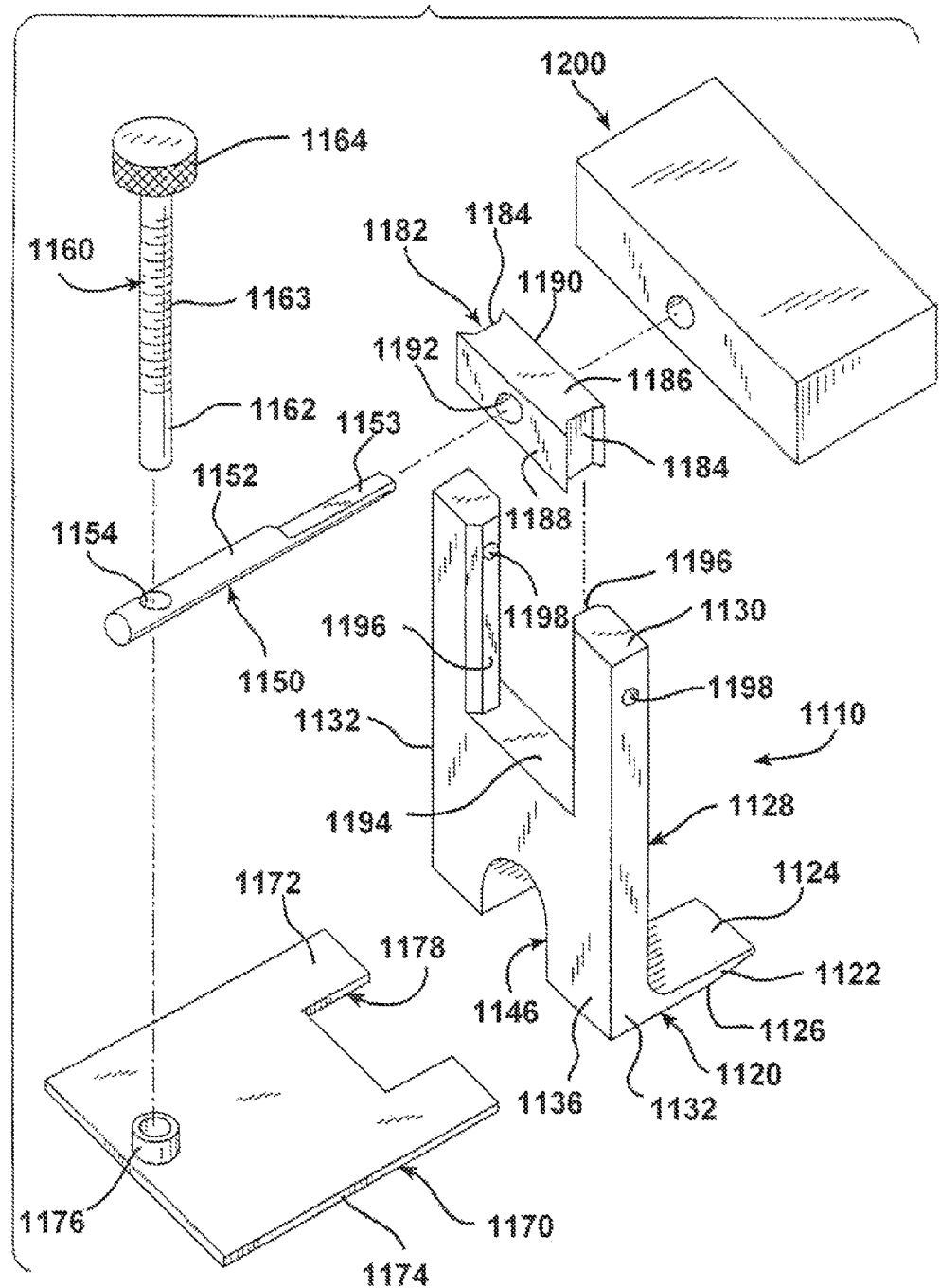
FIG. 57 is an exploded view of another embodiment of the femoral alignment apparatus of the present invention showing the guide body component, a rotating arm component, an extension rod component, and a tibial referencing component.
Figure 58:
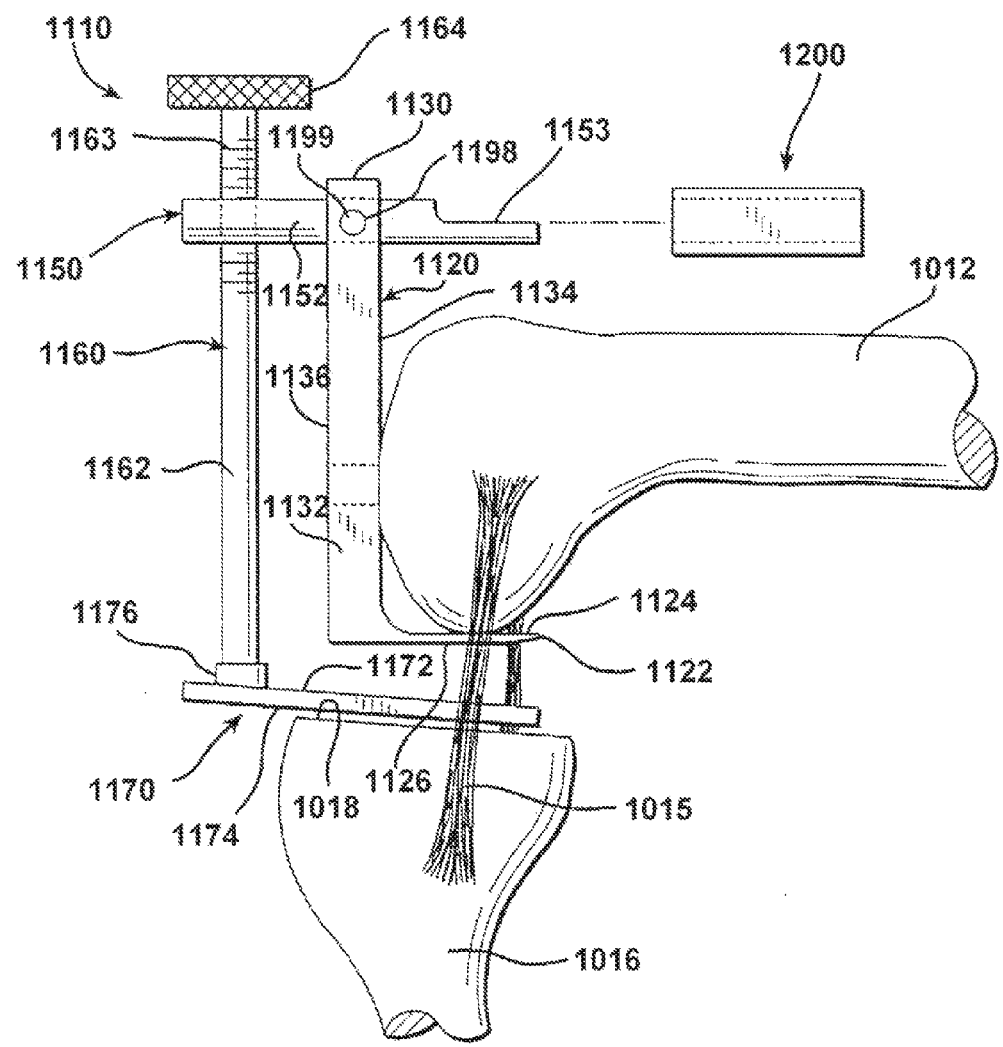
FIG. 58 is a side plan view of the apparatus shown in FIG. 57 attached to a flexed human knee joint including a distal femur, a partially resected proximal tibia, and collateral ligaments.
Figure 59:
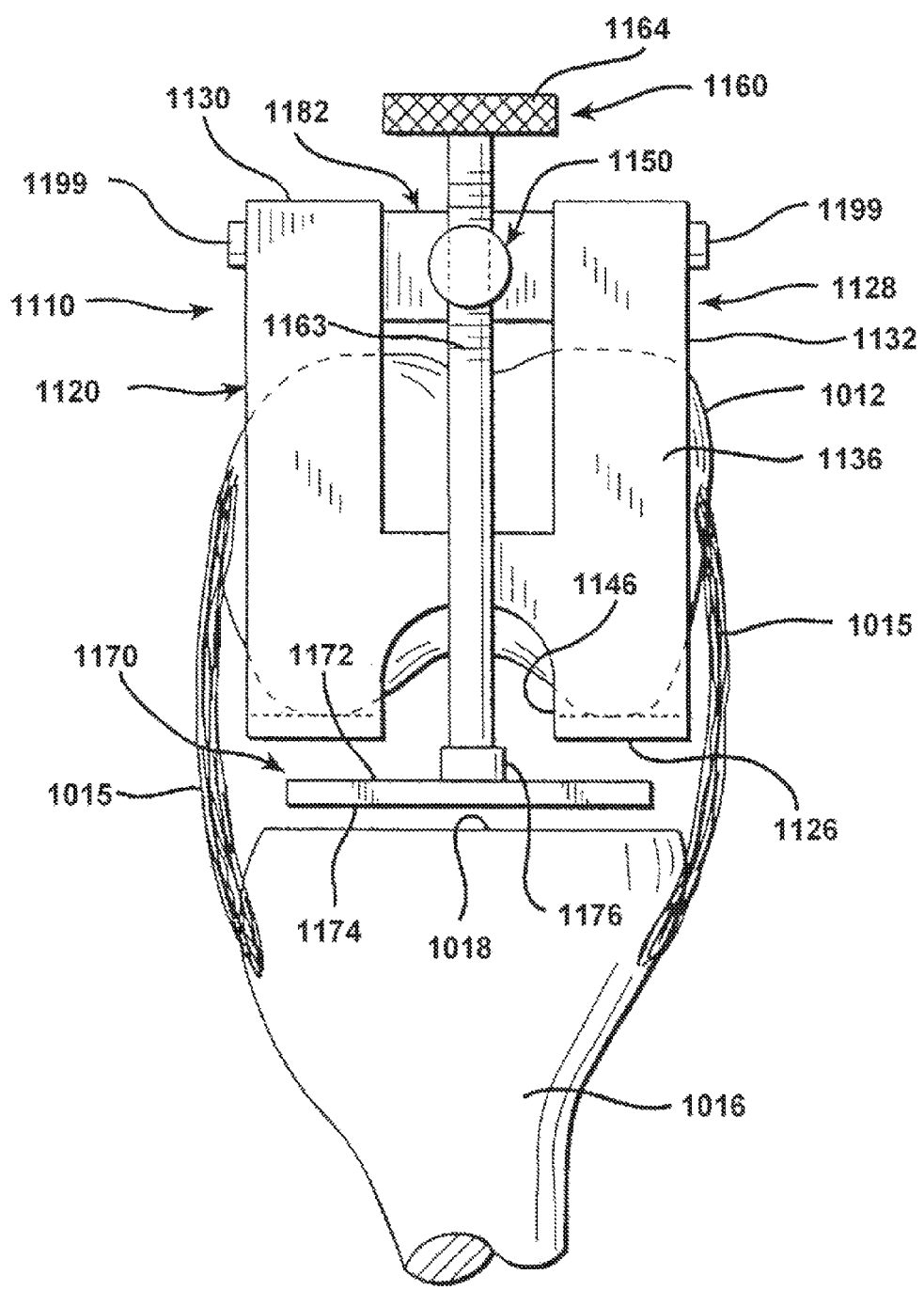
FIG. 59 is a front plan view of the apparatus shown in FIG. 57 attached to a flexed human knee joint including the distal femur, the partially resected proximal tibia, and the collateral ligaments.

In another embodiment of the present invention, as shown in FIGS. 57-59, the femoral resection alignment apparatus is adapted to work in conjunction with a system like the Femoral Resection apparatus described in U.S. patent application Ser. No. 08/300,379 filed Sep. 2, 1994 which includes a pattern means positioned about the femur for guiding the resecting of the femur. Use of the present alignment device with Femoral Resection Apparatus permits the location and orientation of the pattern means to be directly controlled through the rotating arm component. In the configuration described in the previous patent application, the shaft of the rotating arm component terminates in the block that allows it to be fastened to the femoral alignment positioning body.

Referring now to FIGS. 57-59, wherein corresponding elements of FIGS. 51-53 are indicated with corresponding reference numerals with the addition of 100. The shaft 1152 of the rotating arm component 1150 extends through the block 1182 and is free to rotate in the block 1182. One end 1153 of the rotating arm component 1150 mates with the crossbar 1200 and dictates the rotational alignment thereof, while the other end mates with the extension rod 1160 of the present invention. Since the extension rod 1160 is connected to tibial referencing plate 1170, the rotating angle of crossbar 1200 and thereby the pattern device that may be attached thereto, not shown, is based off of the proximal tibial resection.

More specifically, the apparatus shown in FIGS. 57-59 is generally indicated at 1110 and includes a guide body 1120, a rotating arm component 1150, an extension rod component 1160, and a tibia referencing component 1170. These components cooperate to properly locate and orient a cross bar 1200 for positioning a pattern device about the distal femur for resecting the distal femur for guiding cutting means for resecting the distal femur.

The guide body, generally indicated at 1120, includes a body 1128 having tongues 1122 extending from a lower end thereof. The tongues 1122 include an upper surface 1124 for contacting and distracting the distal femur with respect to the proximal tibia. The tongues also include a lower surface 1126.

The guide body 1128 includes top surface 1130, sides 1132, front surface 1134, and rear surface 1136. The guide body further includes a channel extending into the body into the body 1128 from the top surface 1130. The channel is defined by side walls 1196 and bottom wall 1194 in guide body 1128. The channel is sized to receive block 1182 through which the rotating arm component 1150 extends. The block 1182 is vertically moveable within the channel of the guide body 1128 and may be fixed into a desired position by lock screws 1199 which extend through apertures 1198 of the guide body 1122 to contact side walls 1184 of the block 1182 to lock the block 1182 within the channel. Positioning of the block 1182 within the channel of the guide body 1128 may be referenced by a numbered scale on the guide 1128.

The rotating arm component 1150 includes a shaft 1152, a keyed surface 1153 for attachment to cross bar 1200 and an aperture 1154 for receiving an extension rod therethrough. A shaft 1152 extends through aperture 1192 in block 1182 and can rotate with respect thereto.

The extension rod component, generally indicated at 1160, includes a rod shaft 1162 having threads 1163 formed thereon. Extension rod 1160 also includes a rod handle 1164 at an upper end of the rod shaft 1162. The rod shaft 1162 extends through the aperture 1154 in the rotating arm component 1150 and is threadibly engaged therewith. Rotation of the extension rod component 1160 by rotating the rod handle 1164 causes the rotating arm component 1150 to travel up or down the rod shaft 1162 in accordance with the direction of the rotation of the extension rod component 1160. This causes the block 1182 to move vertically with respect to the rod shaft 1162 and in turn causes the guide body 1120 to move up and down with respect to the extension rod 1160.

The tibia referencing component, generally indicated at 1170, includes an upper surface 1172, a lower surface 1174, an extension rod attachment means 1176 and a spacing channel 1178. The tibia referencing component 1170 is interconnected with the extension rod component rod 1160 by attachment means 1176. Preferably, the extension rod attachment means 1176 interconnects the tibia referencing component 1170 with the rod shaft 1162 and permits the rod shaft to be freely rotated therein.

As seen in its operative position in FIG. 58, the femoral resection alignment device 1110 is positioned within the knee joint in flexion between resected surface 1018 of the tibia 1016 and the femur 1012. The lower surface 1174 of the tibia referencing component 1170 contacts the resected proximal surface 1018 of the tibia 1016. The extension rod component 1160 stands up from the tibia referencing component 1170, the rod shaft 1162 interconnected with the extension rod attachment means 1176 which holds the rod shaft 1162 perpendicular to the tibia referencing component 1170. Riding on the rod shaft 1162 is rotating arm component 1150. The body 1152 of the rotating arm component 1150 is received by block 1182 which is locked into position within the guide body 1128 by locking screws 1199 interconnected with the guide body 1120. The tongues 1122 of the guide body 128 are positioned below the posterior condyles of the femur 1012 and the upper surfaces 1124 of the tongues 1122 contact the posterior condyles of the femur.

In operation, the tibia referencing component contacts the resected proximal surface 1018 of the tibia 1016 and the extension rod component 1160 is actuated to lift the rotating arm component 1150 and accordingly, the guide body 1128 and tongues 1122 to distract the femur 1012 with respect to the tibia 1016. The collateral ligaments 1015 are accordingly drawn up to a tensioned position.

As best shown in FIG. 59, after the femur 1012 is distracted with respect to the tibia 1016, it can be seen that the rotating arm component 1150 rotates with the tibia referencing component 1160. Thereafter, as can be seen in FIG. 60, after the femur is distracted from the tibia and the tibia referencing component 1170 is placed on the resected tibia 1016, the rotating arm component 1150 is naturally rotated to correspond to the pitch of the resected tibia. Thereafter, the crossbar 1200 can be placed onto the keyed surface 1153 of the rotating arm component 1150 to track the rotational alignment of the rotating arm component 1150 to properly rotate the crossbar 1200 with respect to the resected tibia 1016. Thereafter, cutting guide devices, not shown, can be interconnected with the cross bar 1200 to extend along the sides of the femur. The cutting guides are thereby accurately positioned for to guide a cutting means resecting the distal femur.

Also as shown in FIG. 60, the block 1182 may have lock screws 1199 attached thereto which extend through elongated apertures or slots 1198 in the guide body 1128 to permit adjusting the block 1182 in the channel of the guide body 1128 and then locking the position thereof. This allows for adjustment and fixation of the anterior-posterior positioning of the pattern device, and for the posterior resection to always parallel the proximal tibia cut.

Importantly, it is the overriding object of both embodiments of the present invention to provide a method and apparatus for locating and orienting the resections of the distal femur based on the resected surface of the proximal tibia. In both cases, this is achieved by putting the knee joint into flexion and distracting the femur with respect to the tibia to tension the collateral ligaments which have already been properly sized by means of ligamentous release. Thereafter, a cutting guide device, be it a conventional cutting guide device or the cutting guide device comprising the pattern device of Applicant's previous patent, is oriented with respect to the orientation of the resected proximal tibia. Other devices to accomplish this purpose are considered within the scope of the present invention.

With the proper use of the previously described system, extremely accurate and reproducible alignment and location of bone cuts are attainable. The preparation of femoral surfaces may be completed in any manner known in the art before and after using the instrumentation of the present invention.

FIGS. 61A-82

In the process of developing the basic instrumentation concept discussed in parent U.S. Pat. No. 5,514,139, it was necessary to attach the cutting guides to the femur in a very robust manner in order to prevent deflection or movement of the cutting guide during the cutting process. The concept utilized to avoid cutting guide movement involved a cannulated screw which applied opposable compression to the medial and lateral sides of the femur while a fixation nail was driven through the cannulae to complete fixation. In the earliest cadaveric evaluations of the instrumentation, it was noted that the fixation thus attained was robust enough to allow the 'patient' to be lifted from the table using the guide. Somewhat accidentally, it was also noted that the fixation of the guide to the bone in this manner also avoided any errors in cutting guide placement. Since the cannulated fixation screws were brought directly into contact with the bone surfaces, the moment arm the pins could be subjected too was minimized and thus prevented mal-alignment of the cutting guides. The teachings of the related parent applications are generally discussed herein with reference to FIGS. 61-65.

Figure 62A:
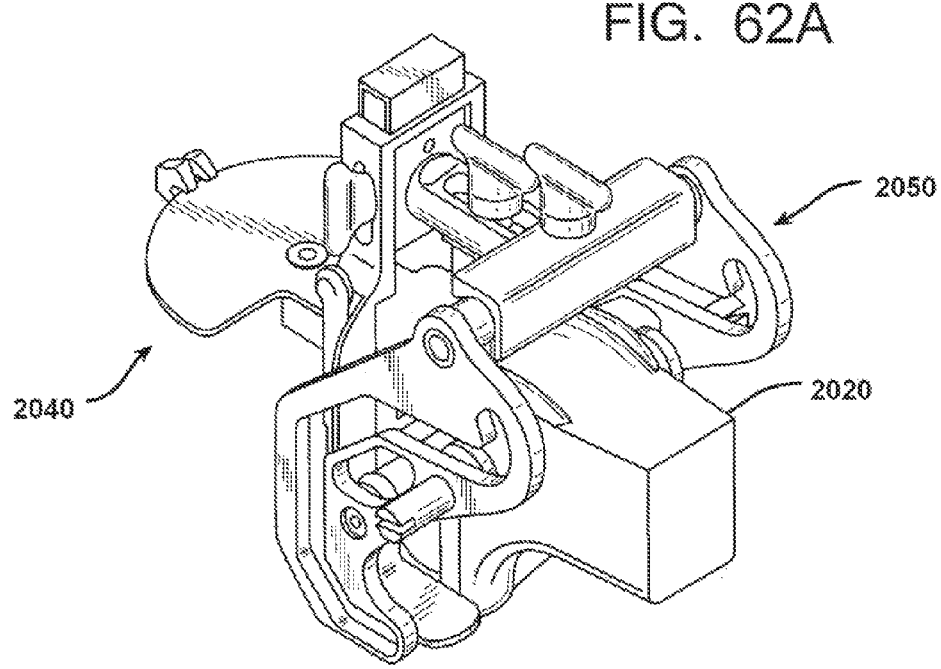
FIG. 62A is a perspective view of the apparatus shown in FIG. 61 affixed to a femur to be resected.
Figure 62B:
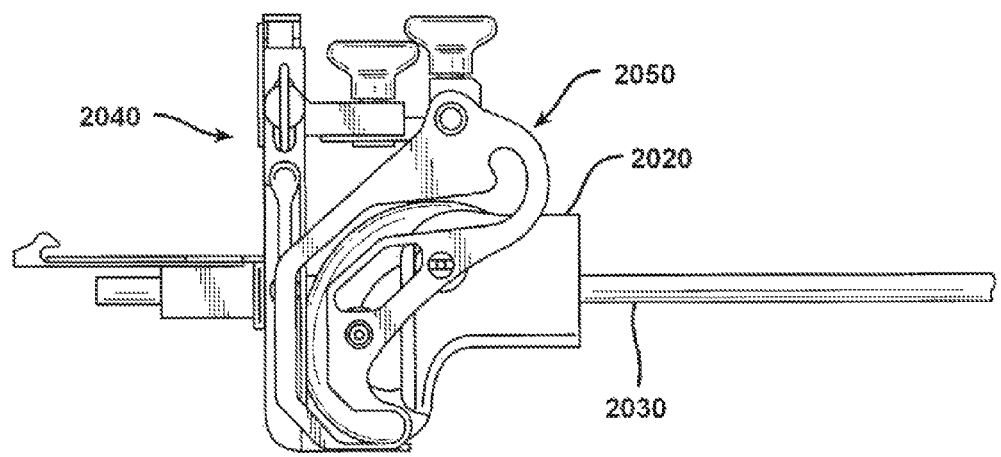
FIG. 62B is a side view thereof.
Figure 63A:
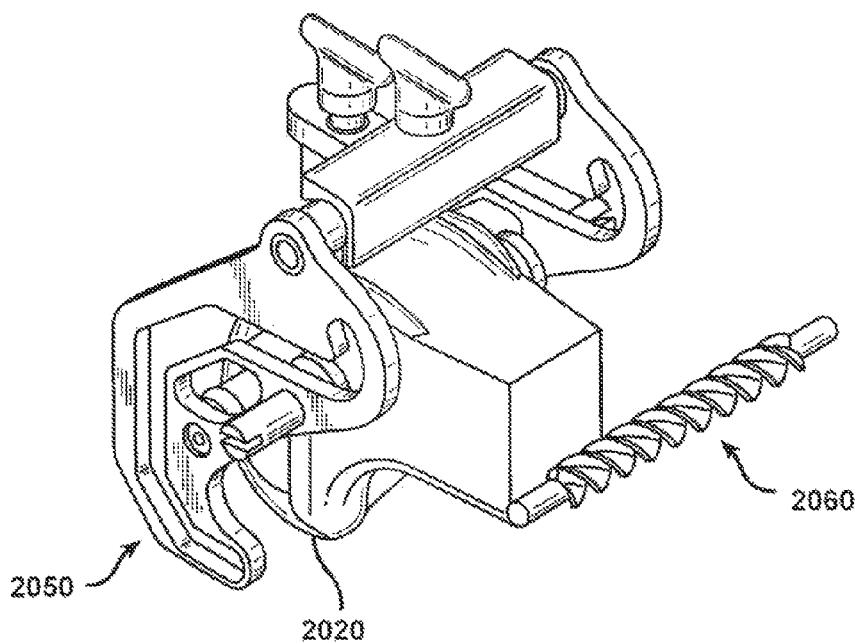
FIG. 63A is perspective view of the cutting guide portion of the femoral resection apparatus shown in FIG. 61 affixed to a femur to be resected, along with a cutting tool.
Figure 63B:
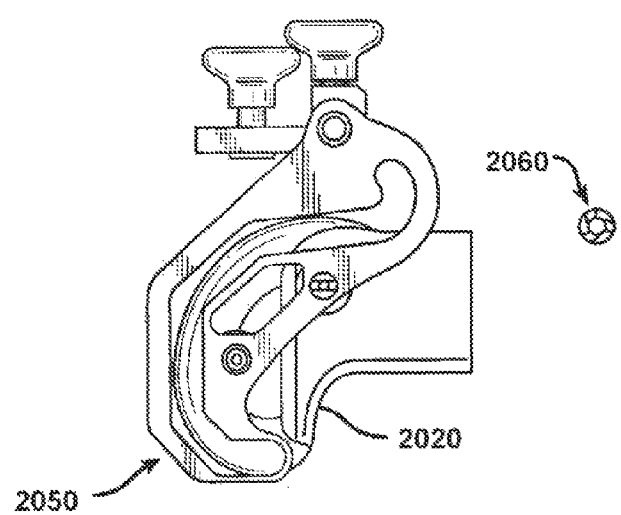
FIG. 63B is a side view thereof.
Figure 64:
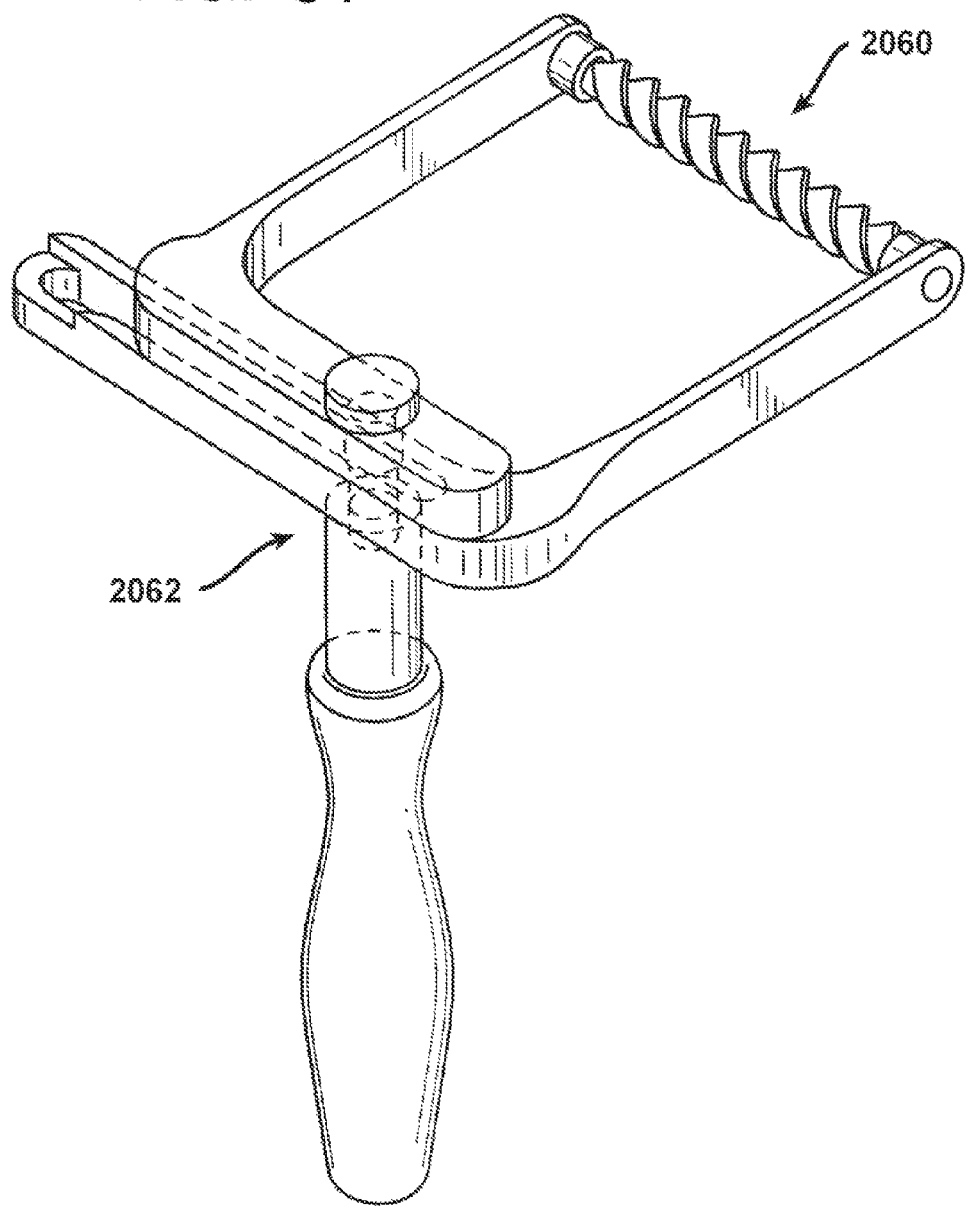
FIG. 64 is a perspective view of a cutting tool and guide handle for resecting a femur.
Figure 65A:
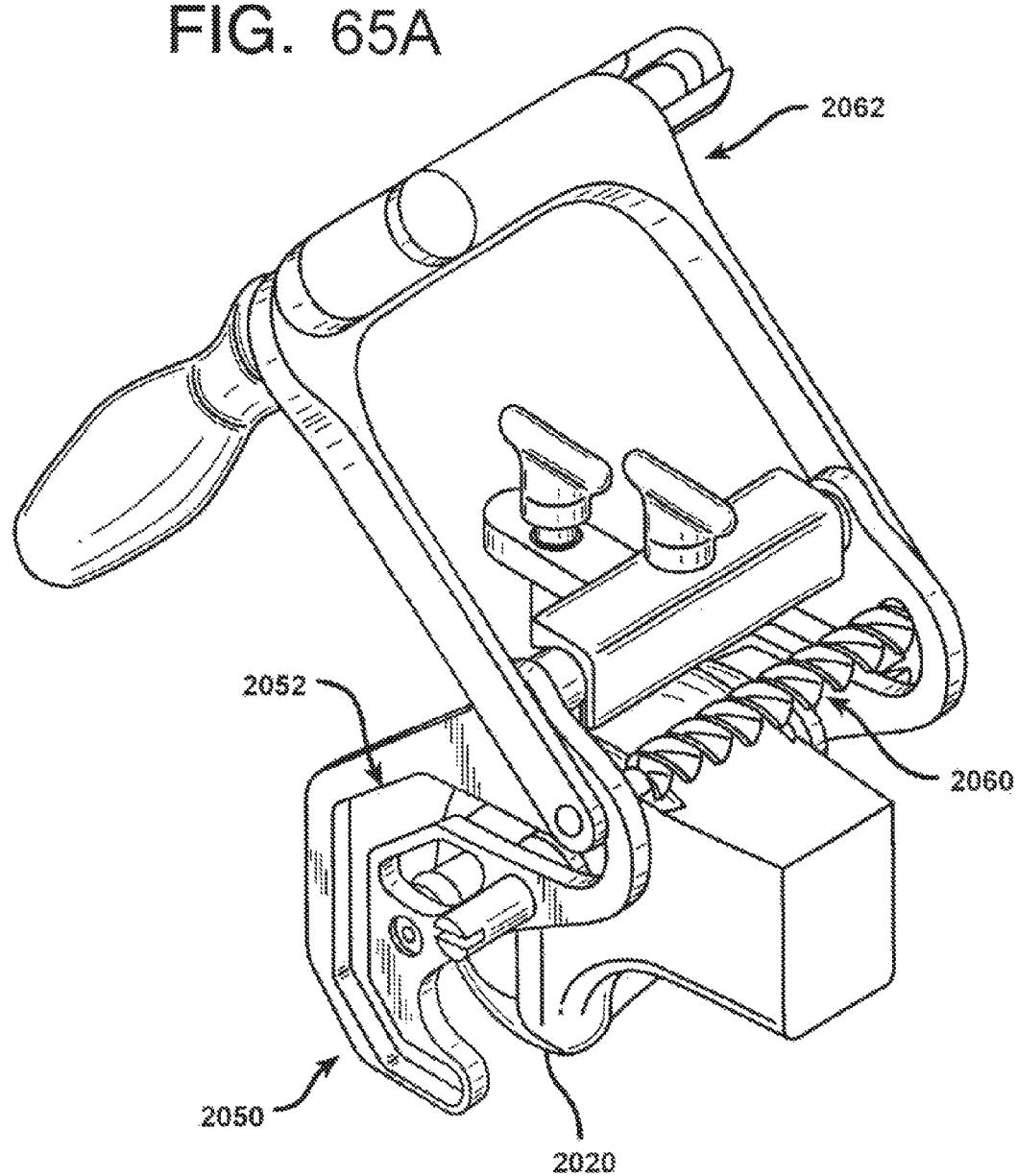
FIG. 65A is a perspective view of the cutting tool interconnected with the cutting guide shown in FIG. 64.

FIGS. 61A and 1B show the first step in this technique where the intramedullary rod 2030 is introduced into the IM canal of the femur 2020 while the alignment guide 2040 and cutting guide 2050 are assembled and then adjusted to the proper relative locations and orientations. FIGS. 62A and 62B show the cutting guide 2050 and the alignment guide 2040 positioned about the femur 2020. The cutting guide 2050 is then fixed to the femur 2020 using cannulated fixation screws and fixation nails. The alignment guide 2040 and intramedullary rod 2030 are then removed. FIGS. 63A and 63B show the cutting guide 2050 fixed to the distal femur 2020 (fixation nails not shown) and the milling tool 2060. FIG. 64 shows the milling tool 2060 and the milling handle 2062. FIGS. 65A and 65B show the milling tool 2060 and milling handle 2062 properly articulated with the cutting guide 2050 prior to initiating the cutting process. The cutting process includes attaching a driver (a DC or AC drill) to the milling tool 2060 and to manually direct the milling tool 2060 and milling handle 2062 through the cutting path 2052 of the cutting guide 2050.

This technique works well in cadaveric evaluations. Interestingly, there is an inability of the milling tool to cut the collateral ligaments or the posterior cruciate ligament, likely due to the amount of surface area of the milling tool in contact with the ligament. An oscillating sawblade brings finely pointed teeth, teeth whose leading tips are directed at 90 degrees to the ligament fibers, directly into contact with the ligaments, and thus a very small force is required for the very small surface area of the teeth to be forced through the ligament. Another way of stating this is that the local pressure induced by the teeth is very high even when motivated by very small forces due the extremely small surface area of contact between the teeth and the ligament. The milling tool, on the other hand, has teeth which are essentially smooth, and which have much larger areas in contact with the ligament, and are oriented tangentially to the fibers and body of the ligament so that even at the maximum force levels induced by manually pushing the milling handle and milling tool into a ligament (perhaps 25 to 50 lbs.), the ligaments are not cut.

It should be noted that conventional milling was used in evaluations. Conventional milling, in the case of this instrumentation, dictates that the milling bit rotates in the opposite of the direction from the cutting direction to maximize both control during cutting and the smoothness of the resulting surfaces. Climb milling, the opposite of conventional milling, is potentially problematic and may be avoided by utilizing a one way clutch between the milling tool and the drill driving the milling tool thus avoiding even accidental use of climb milling.

FIGS. 66-69 show a variation on the methods and apparatus of the parent applications which improves the accuracy and ease of use of the instruments. FIGS. 66A and 66B show the alignment guide 2140 connected to a drill guide 2142. The drill guide 2142 has hole locators 2144 for locating positioning hole(s) in the medial and lateral sides of the femur 2020 that correspond to the fixation features (nubs or cannulated screws) of the cutting guide, as will be described.

Figure 67A:
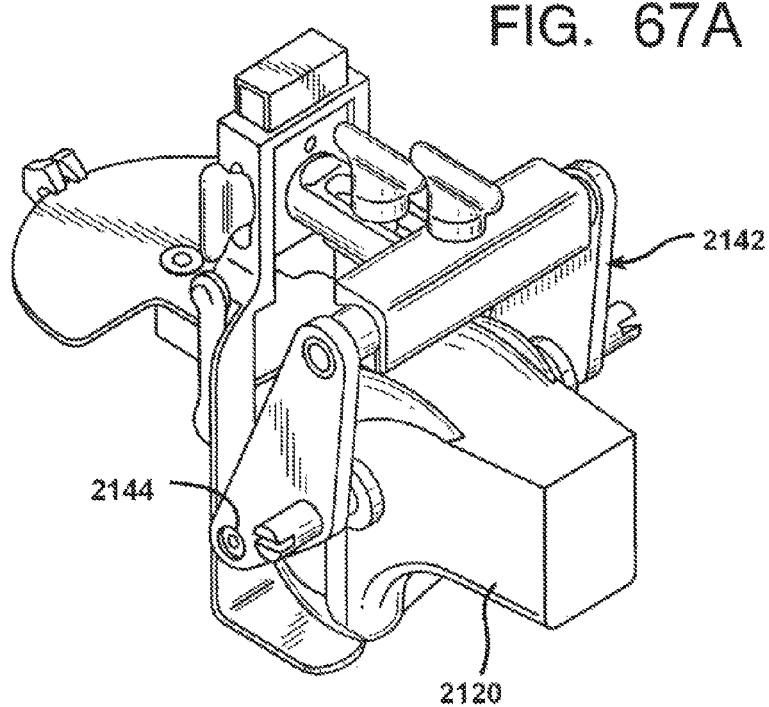
FIG. 67A is a perspective view of the positioning and drill guide apparatus shown in FIG. 66 positioned on a femur to be resected.
Figure 67B:
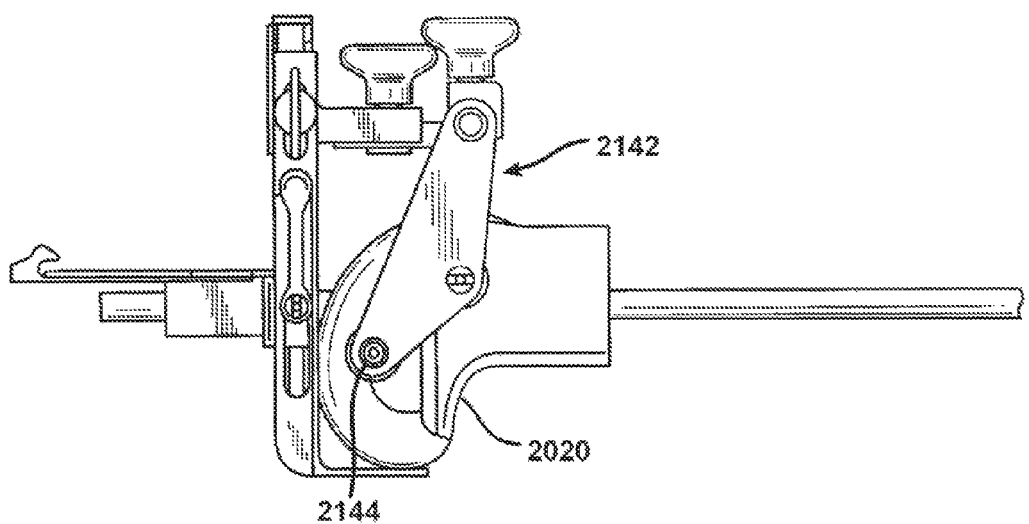
FIG. 67B is a side view thereof.

FIGS. 67A and 67B show the drill guide 2142 located about the sides of the distal femur 2020. At this point a drill is used to drill through the hole locators 2144 in the drill guide 2142 to create positioning hole(s) in the medial and lateral sides of the femur. It should be noted that it is possible to place only the distal-most positioning hole in the femur using the drill guide 2142, and then to rely on an extramedullary reference to determine the appropriate flexion-extension alignment for the anterior-most fixation point.

Figure 69:
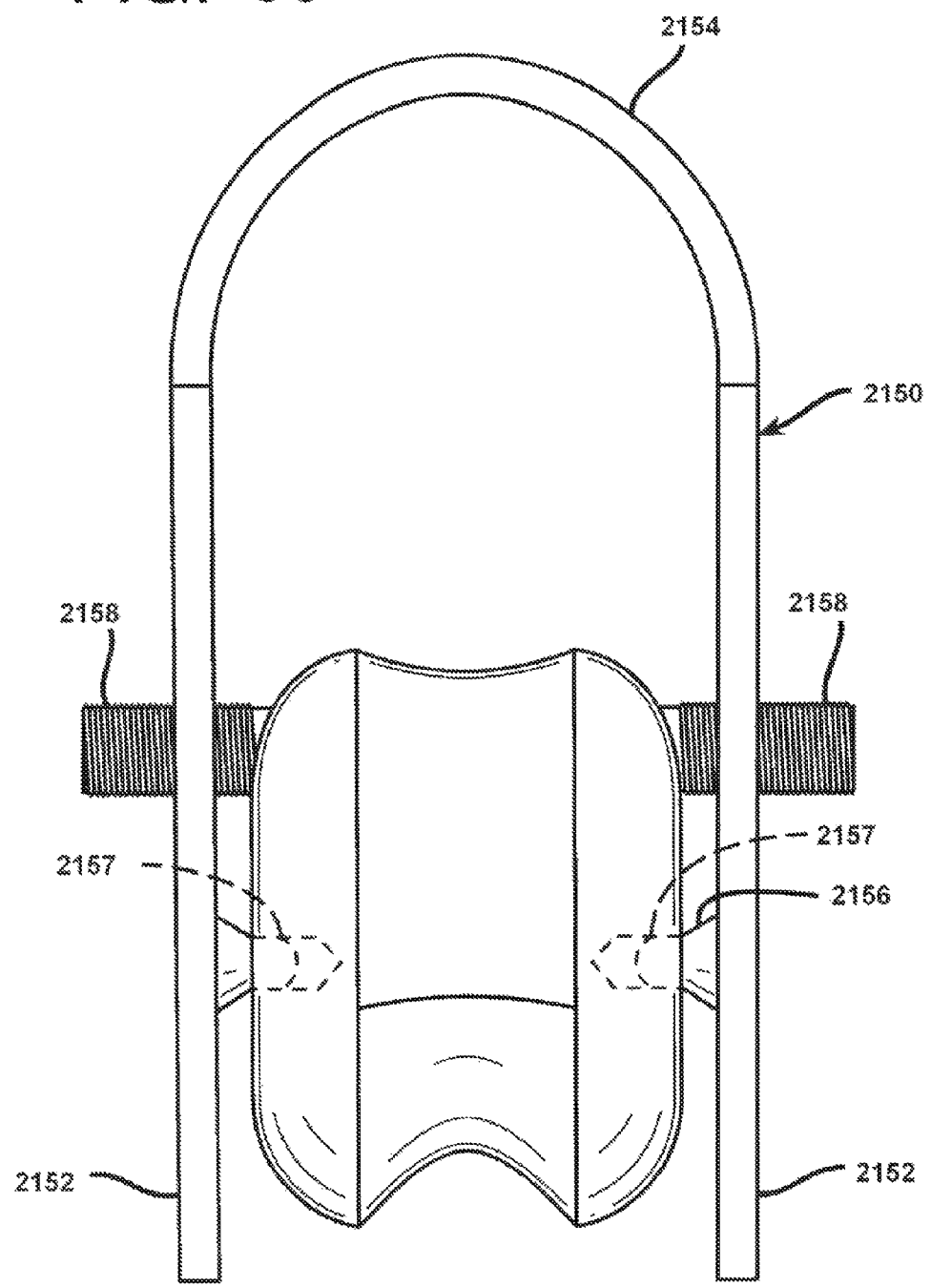
FIG. 69 is a front view of the cutting guide shown in FIG. 68 attached to a femur to be resected.

FIG. 68 shows the cutting guide 2150 of this embodiment, having side plates 2152 with a cutting path described therein, and an upper bridge 2154 interconnecting the cutting plates 2152. To position the cutting guide 2150 on a femur to be resected 2020, the side plates are spread apart to allow for the introduction of fixation nubs 2156 into the positioning holes 2157 created previously in femur 2020. FIG. 69 shows the fixation nubs 2156 engaged in the positioning holes 2157, and additionally, cannulated fixation screws 2158 fixed to the medial and lateral sides of the femur. The step of cutting the distal femur 2020 is essentially identical to the techniques shown in FIG. 65.

Figure 70:
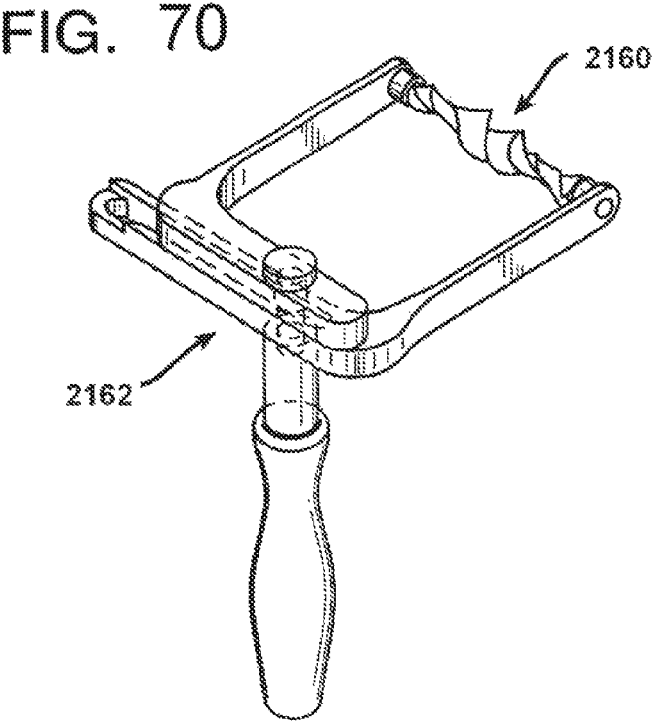
FIG. 70 is a perspective view of a cutting tool and handle wherein the cutting tool has a curvilinear profile.
Figure 71:
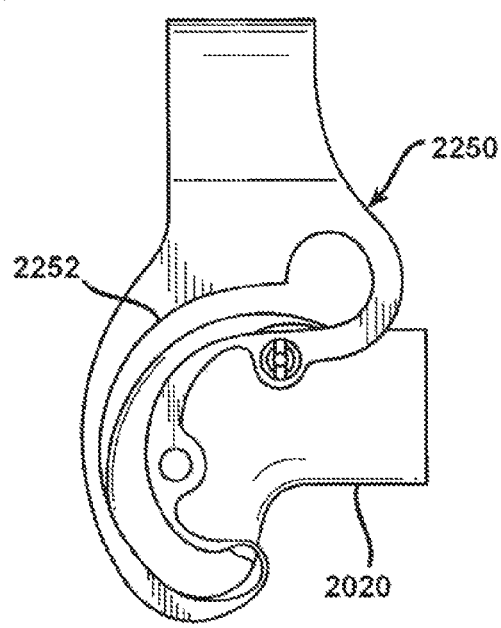
FIG. 71 is a side view of a cutting guide having a curved cutting path attached to a femur to be resected.
Figure 72:
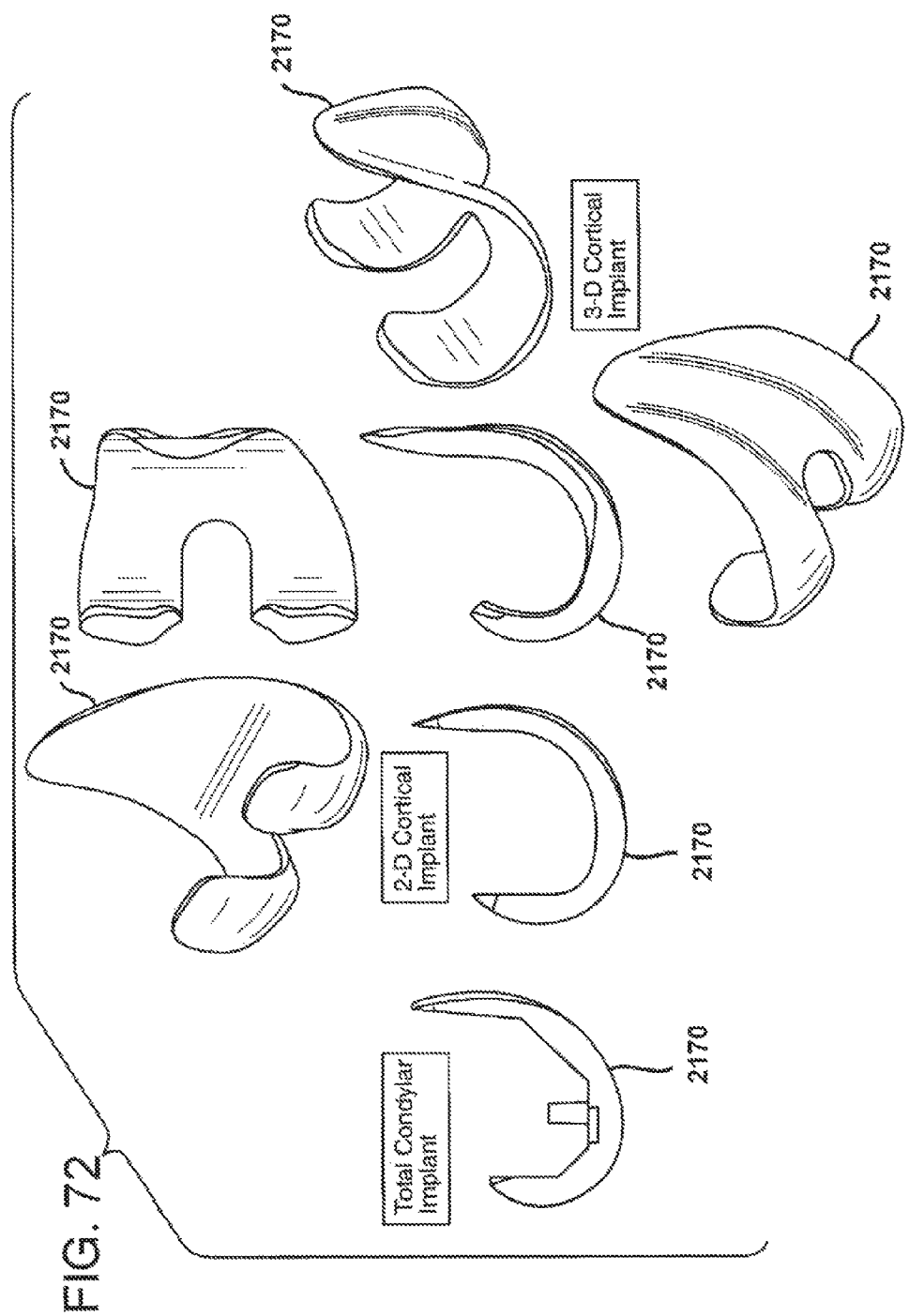
FIG. 72 shows a number of perspective and side views of an implant having a curved attachment face.

FIG. 70 shows a milling tool 2160 and handle 2162 wherein the cutting blade has a curvilinear profile instead of a linear profile. This allows for shaping the profile of the resection. FIG. 71 shows a cutting guide 2250 with a curved cutting path 2252, so that a curved cutting path can be used to resect the femur. Using the cutting guide 2250 with the curved cutting path 2252, together with the curvilinear profile milling tool 2160 shown in FIG. 70 allows for the resected femur 2020 to have a curved profile and a curved path. Shown in FIG. 72 are examples of a cortical femoral components 2170 with linear paths, with curved and linear paths, with curved paths, and with curved paths and curved profiles.

Figure 73B:
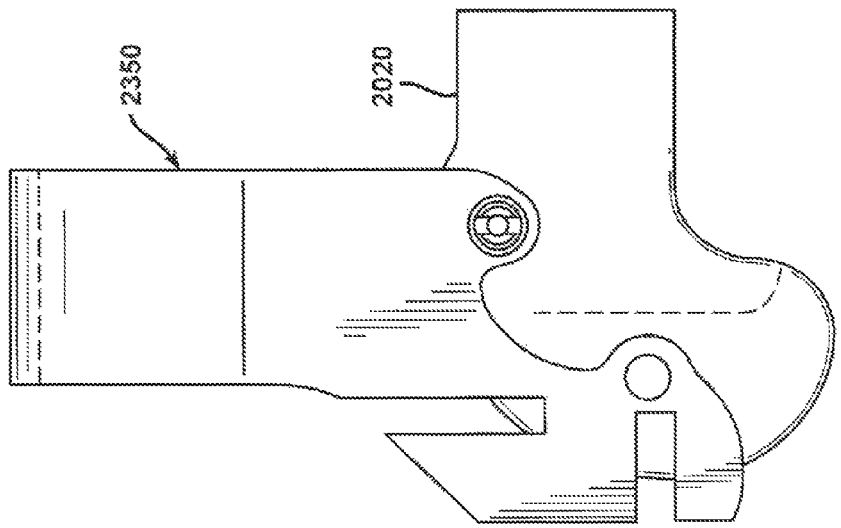
FIGS. 73A and 73B show front and side views of a cutting guide for positioning a cutting block for use with an oscillating saw for resecting a femur.
Figure 73A:
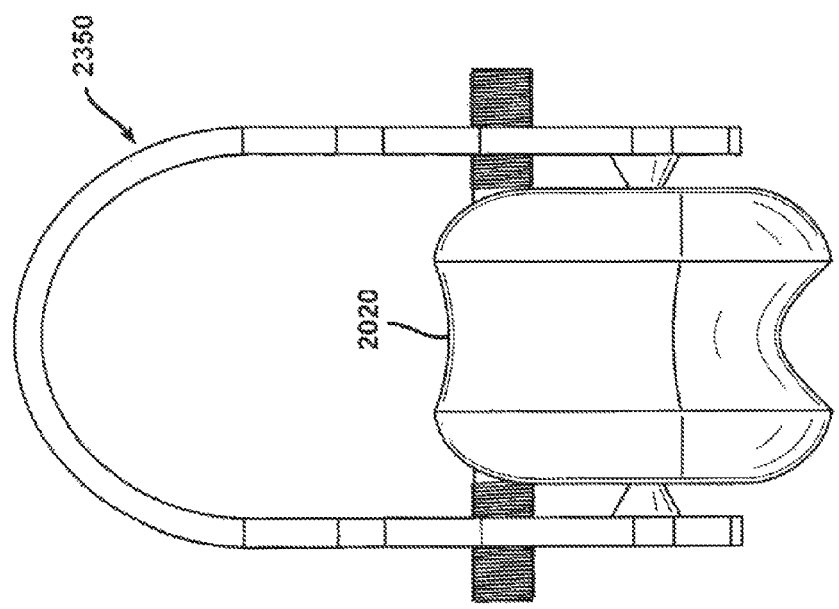
Figure 74B:
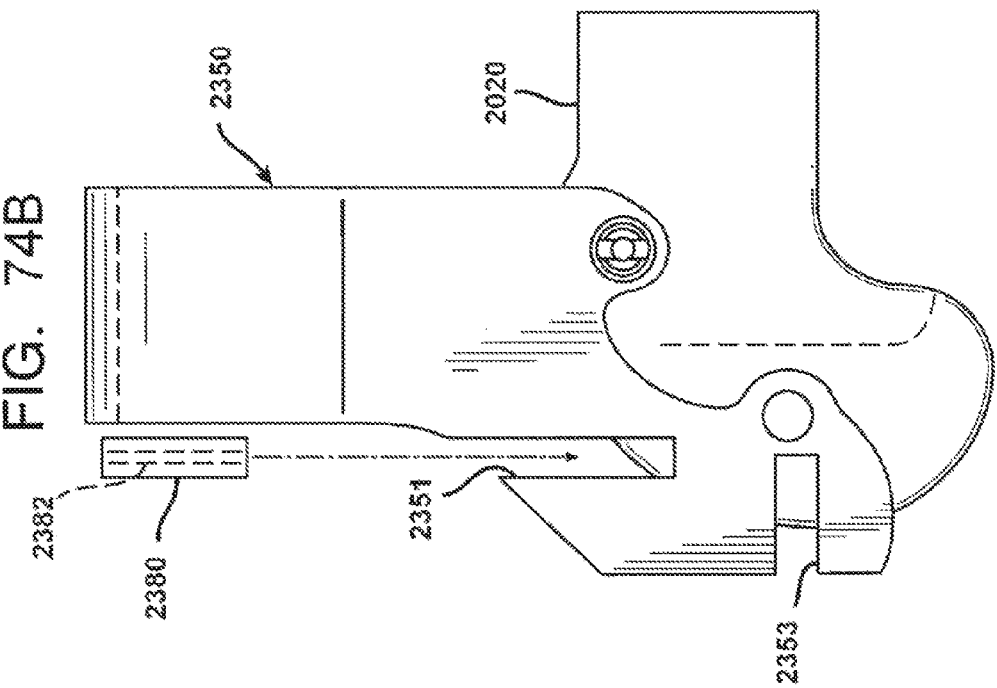
FIGS. 74A and 74B show front and side views of a distal cutting guide for use with the cutting guide shown in FIG. 73.
Figure 74A:
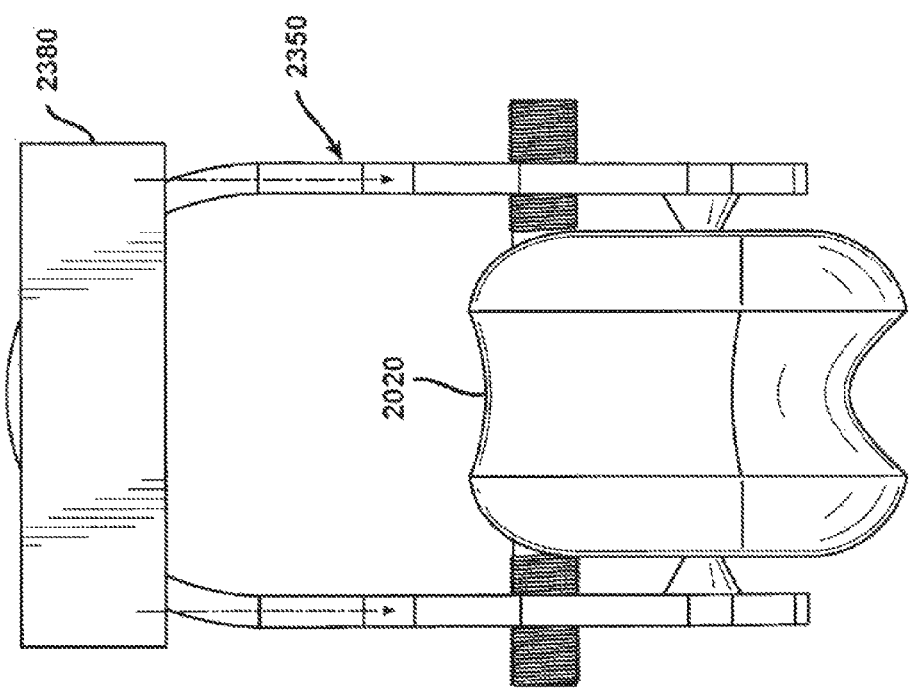
Figure 75A:
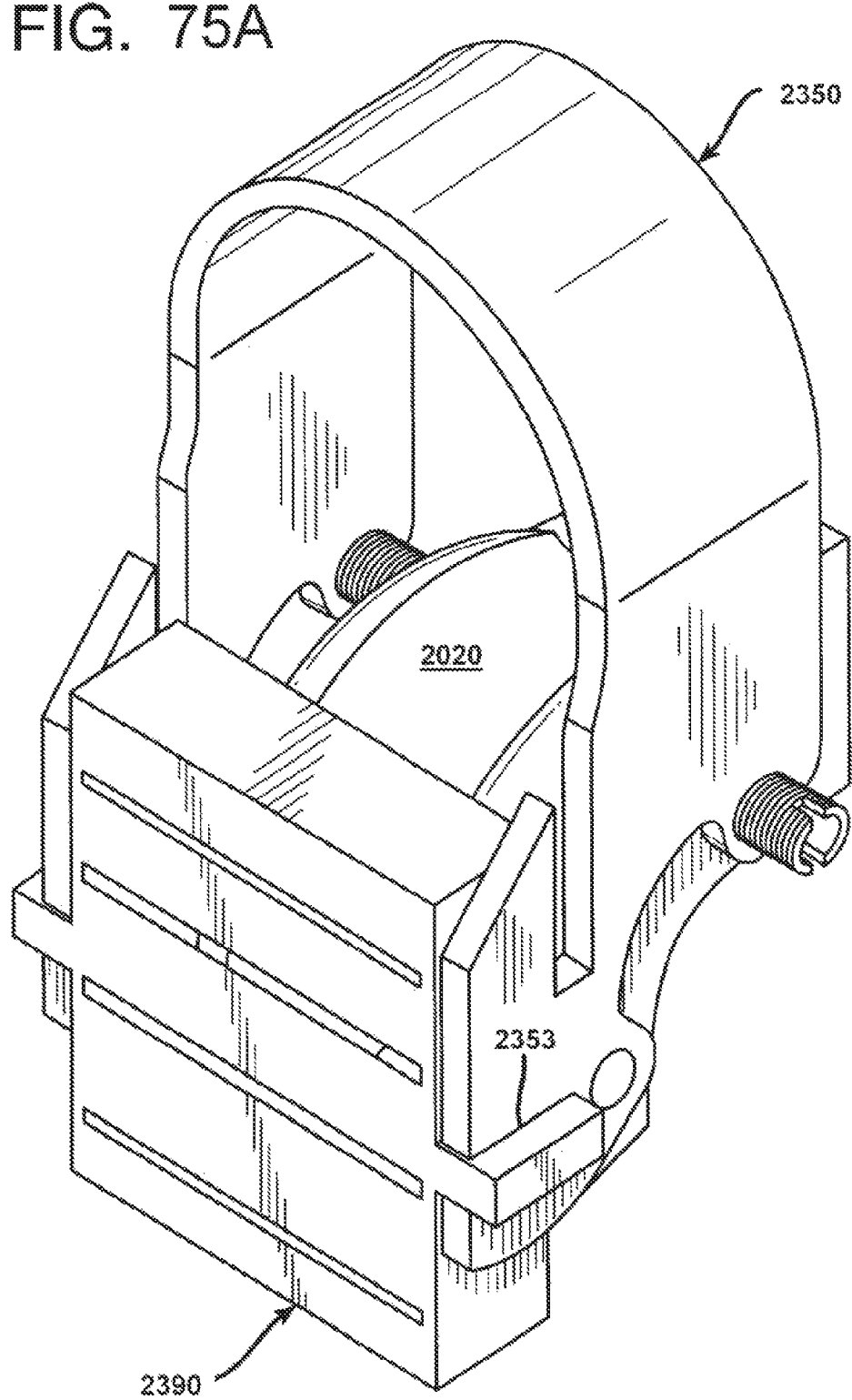
FIG. 75A is a perspective view of a cutting block interconnected with the cutting guide shown in FIG. 74, and FIGS. 75B and 75C are side and front views thereof.

Referring now to FIGS. 73-75, it can be seen that similar techniques can be applied to the use of an oscillating sawblade and a conventional cutting block. FIGS. 73A and 73B show a modified cutting guide 2350 attached to the distal femur 2020 in a manner similar to the milling cutting guide 2150 shown in FIG. 69. FIGS. 74A and 74B show a distal resection cutting guide 2380 being attached to the cutting guide 2350 by positioning the distal resection cutting guide 2380 in slot 2351. An oscillating saw is inserted into the slot 2382 of the distal resection cutting guide 2380 and the distal resection is completed. As shown in FIGS. 75A, 75B, and 75C, after the completion of the distal resection and removal of the distal resection cutting guide 2380, a 4 in 1 cutting guide block 2390 can be inserted into slot 2353 until it contacts the distal resection surface of the femur 2020. The remaining femoral resections could then be completed as is known in the art. This technique provides an advantage over other 5 in 1 oscillating sawblade techniques in two ways. First, the accuracy of cutting guide placement in significantly improved and second, the leading edges of the sawblade slots in the cutting guides may be brought into direct contact with the bone to be cut thus avoiding excessive cantilevering of the sawblade resulting in sub-optimal cuts.

Figure 76:
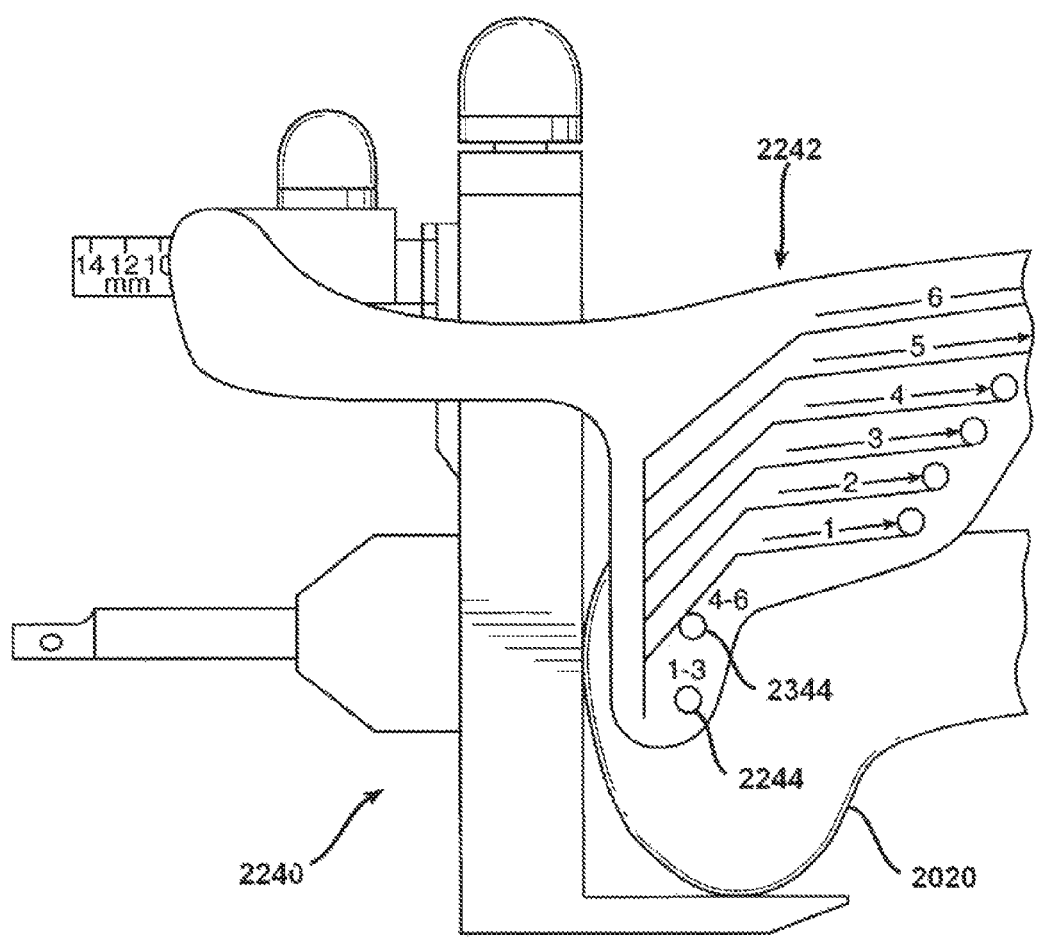
FIG. 76 is a side view of the positioning and drill guide apparatus shown in FIG. 66 showing size markings thereon.
Figure 77:
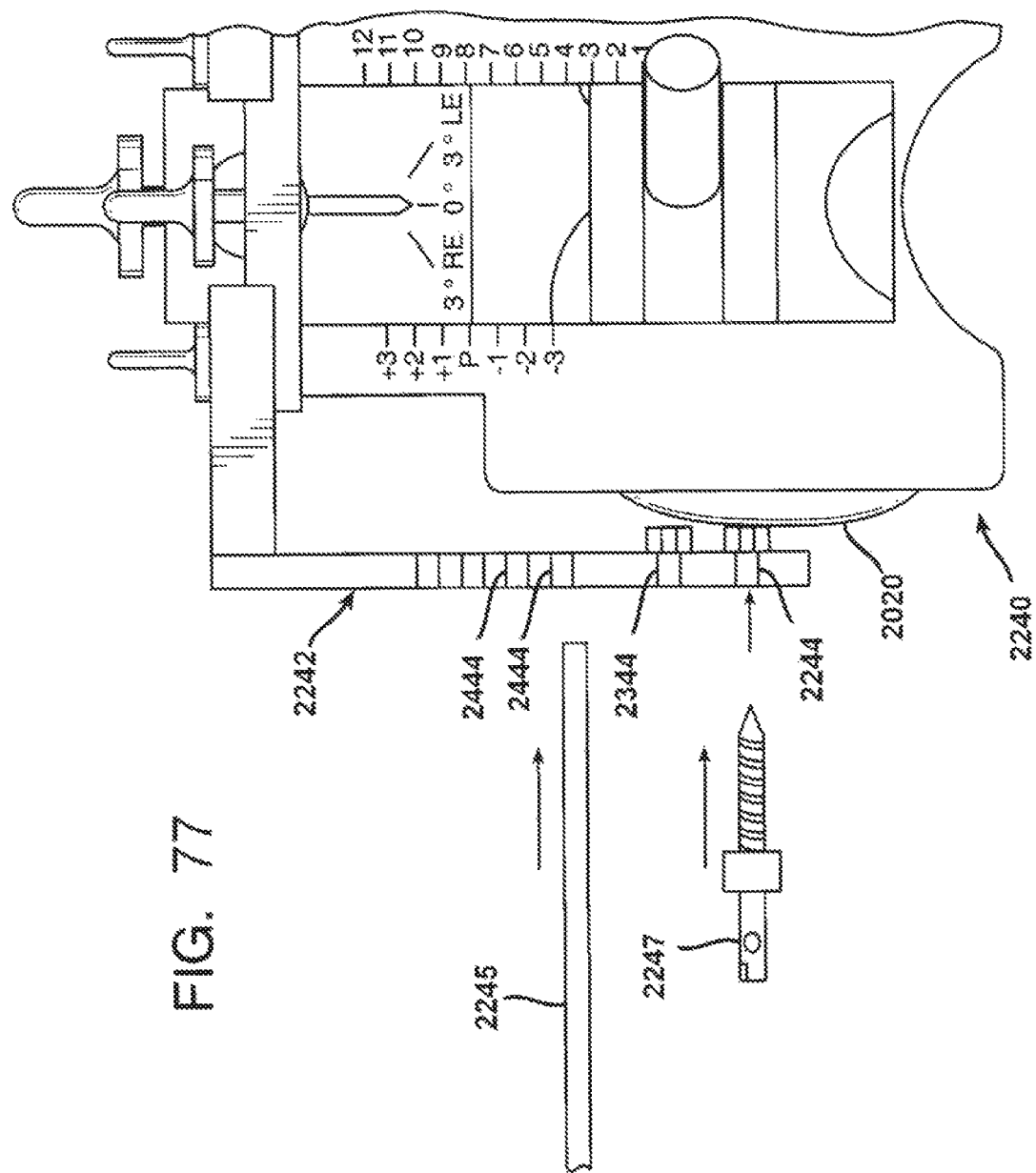
FIG. 77 is a back view thereof.

FIG. 76 is a close up side view of the alignment guide and drill guide shown in FIG. 66. The alignment guide 2240 interconnects with the drill guide 2242. The drill guide includes a plurality of drill hole locators 2244, 2344 and size markings. FIG. 77 is a back view of the alignment guide 2240 and drill guide 2242 shown in FIG. 76. Also shown in FIG. 77 are drill hole locators 2244, 2344, fixation drill 2247, and sizing rod 2245 for extending through sizing apertures 2444. The sizing rod 2245 can be placed from the medial side of the femur to the lateral side in the exact position of the anteriormost tip of the implant corresponding to the size intended for that hole. In this way, the drill holes for cutting guide placement are directly linked to the anterior size reference and the alignment guides reference of the posterior condyles thus minimizing any form of tolerance stacking and allowing for the easy implementation of simultaneous anterior and posterior referencing and adjustment.

Figure 78:
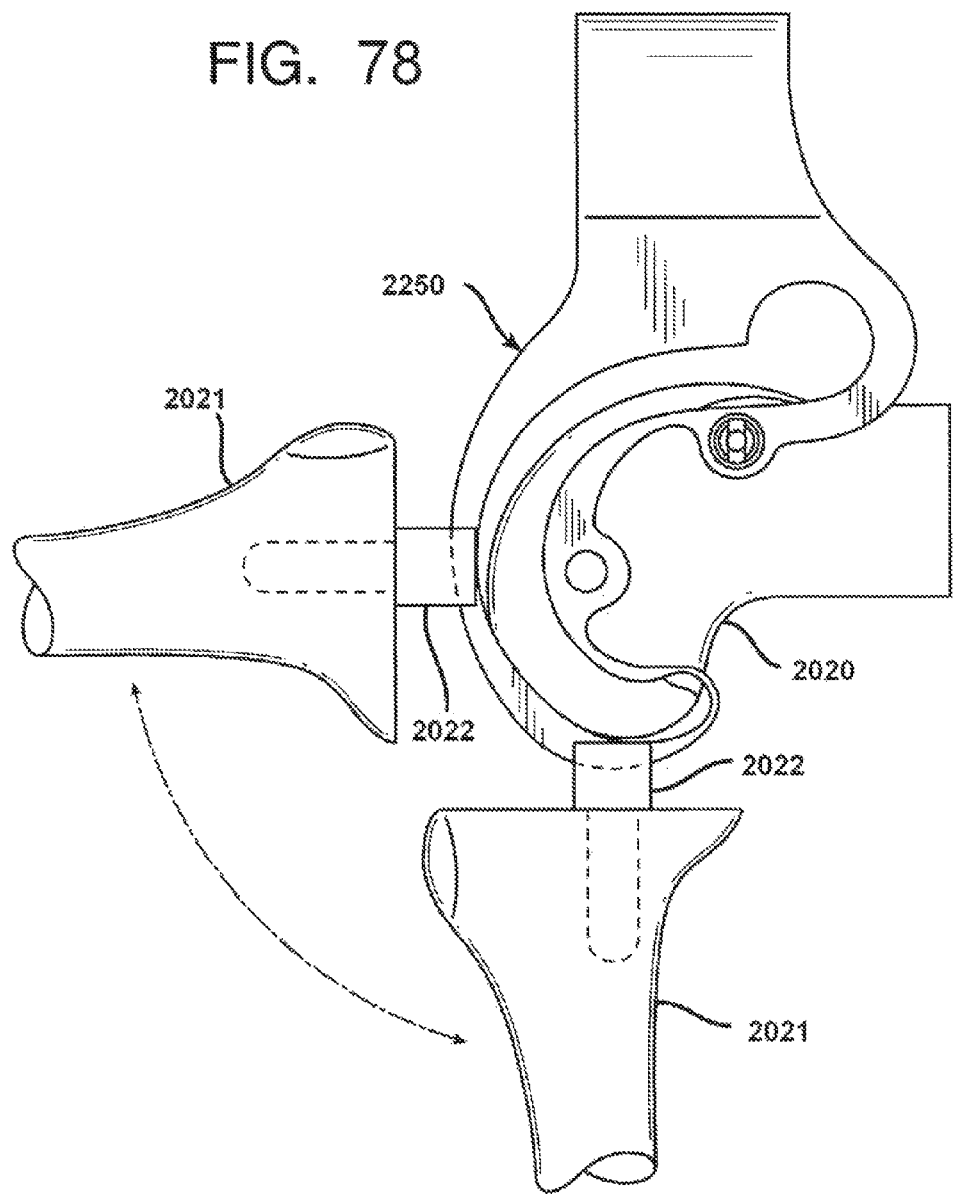
FIG. 78 is a side view of the cutting guide having a curved cutting path shown in FIG. 71 used in connection with ligament balancing.
Figure 79:
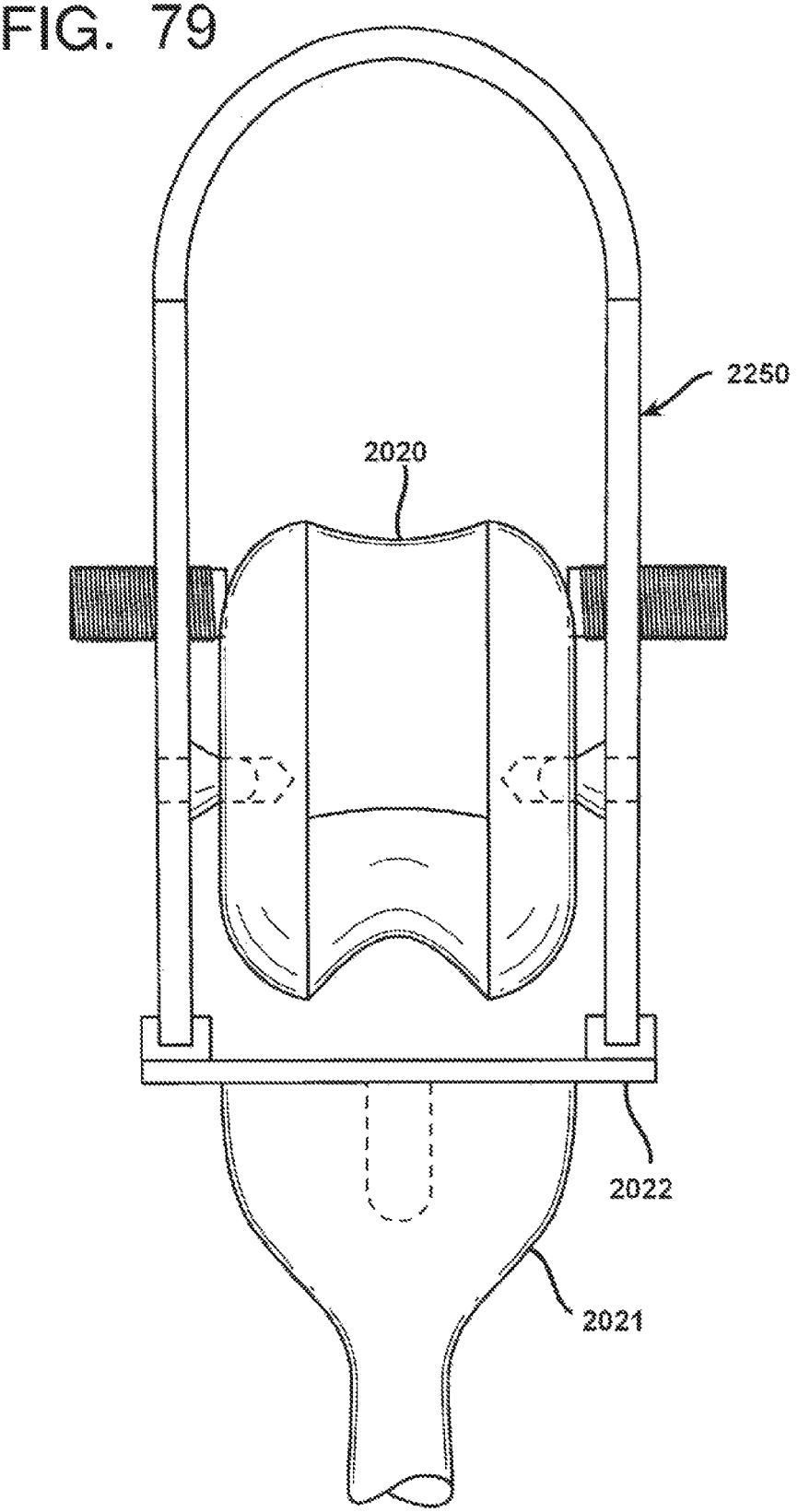
FIGS. 79 and 80 are front and perspective views thereof.
Figure 80:
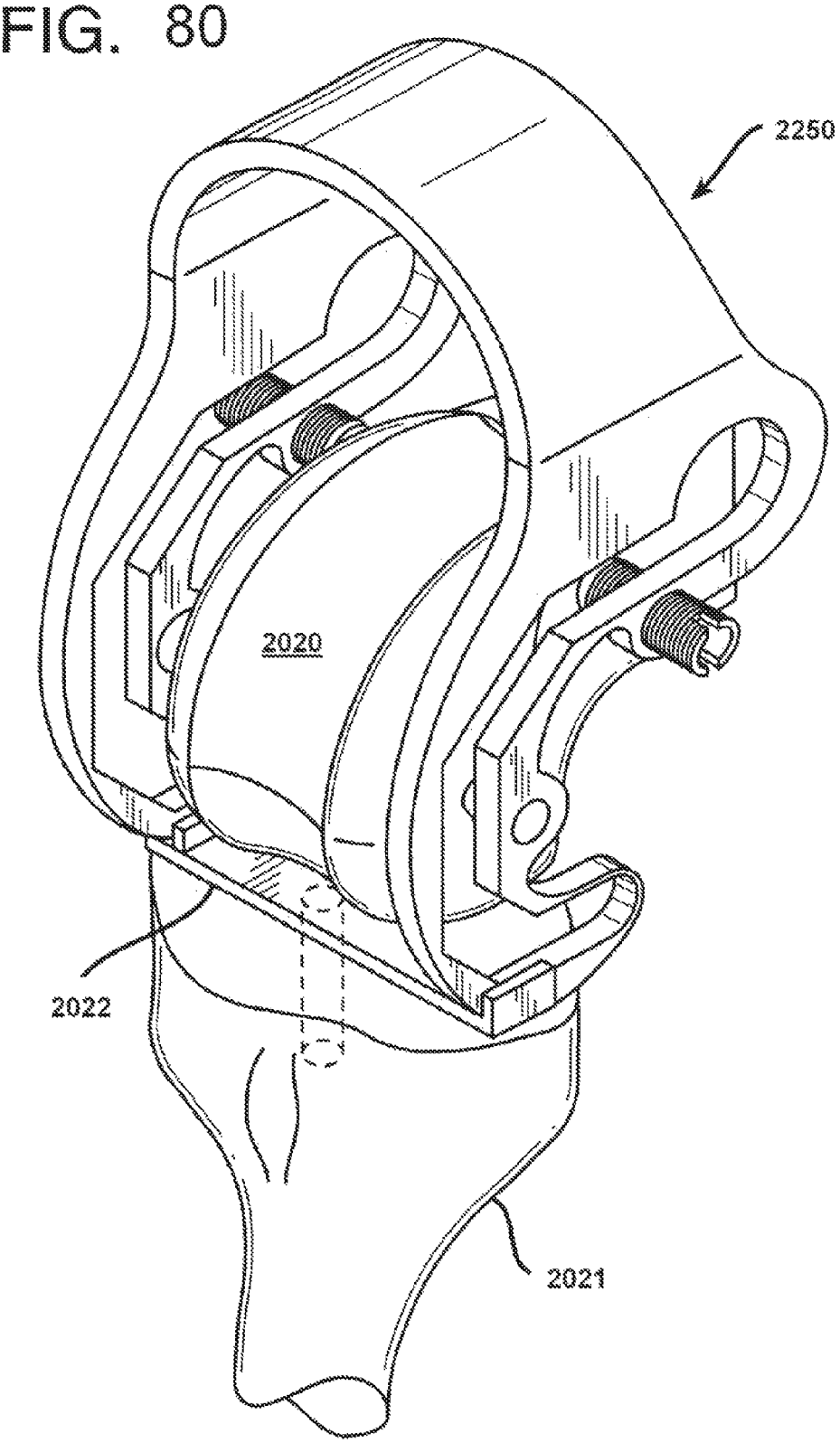

FIGS. 78-80 relate to method of ligament balancing using the cutting guide 2250 shown in FIG. 71. Soft tissue balancing for TKA is considered to be crucial in the use of mobile bearing designs. The re-popularization of this technique has spurred the development and commercialization of some very intricate instrumentation systems that are very prone to surgeon misuse due to their complexity. Another drawback of these systems is that they balance the tissues in flexion and extension, but do not allow continuous reference of the soft tissue balance throughout the range of motion similar to that achieved by trial reduction. By creating the edges of the cutting guide 250 (or even a trailing guide including no cutting guide or cutting guide attachment features) in a profile or geometry that simulates the geometry of the implant and having that geometry act or articulate with a referencing means on the cut proximal tibia 2021 and reference bar 2022 attached thereto, an effective trial reduction of soft tissue balance may be attained prior to any femoral resection.

Figure 81:
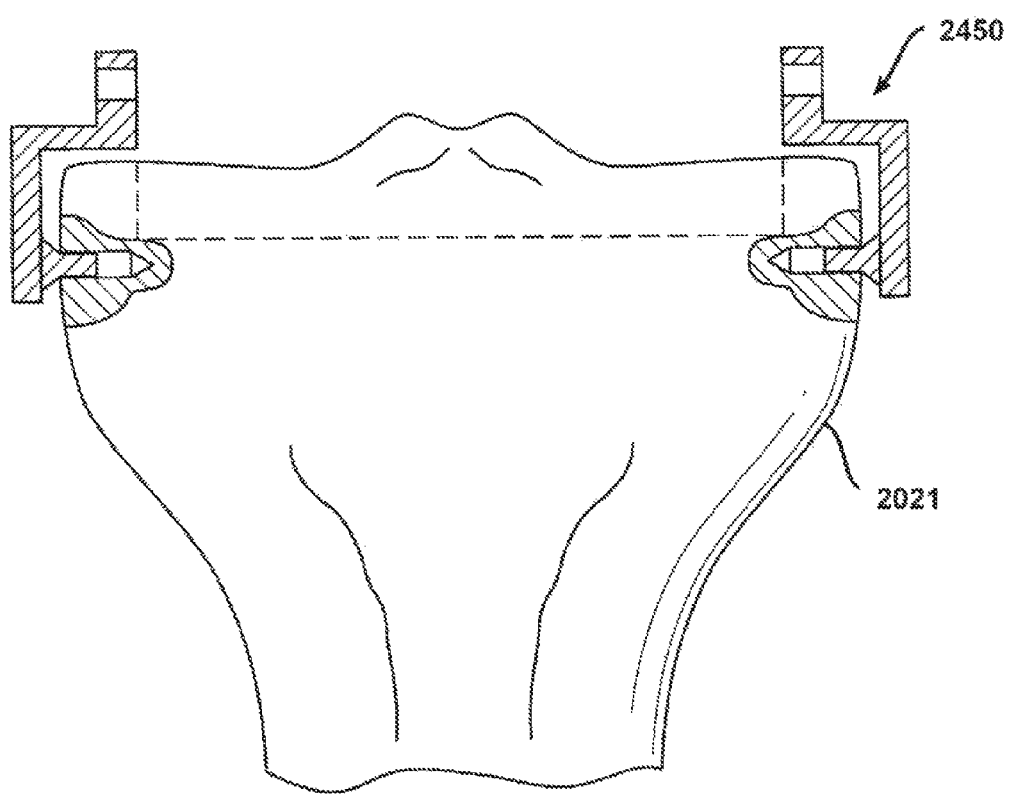
FIGS. 81 and 82 are front and side views of a cutting guide attached to a tibia.
Figure 82:
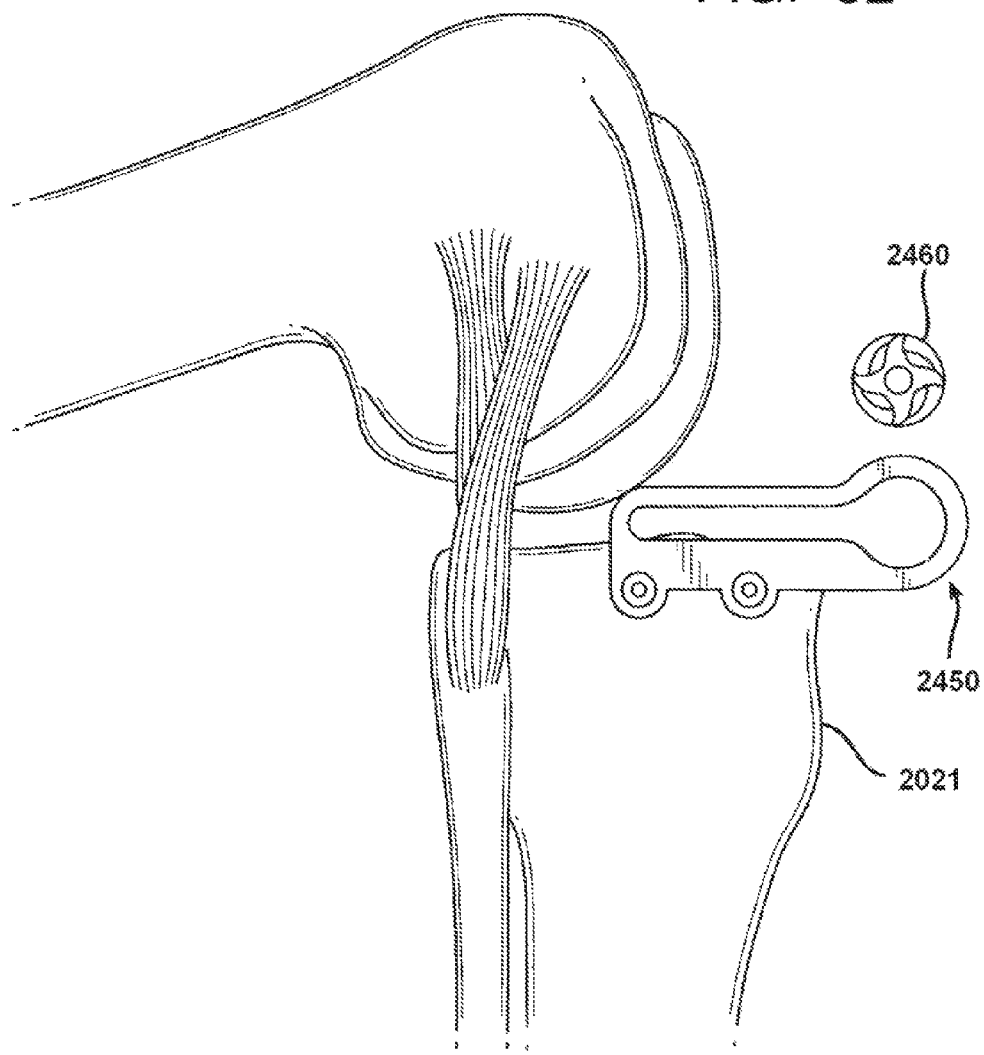

The cutting guide surfaces of the cutting guide need not be coplanar with the surfaces to be created in a bone, but may instead be parallel, but offset. Also the cutting guides may be located over the surfaces of the bone to be cut, but not necessarily located about the sides of the entire bone to be cut. As shown in FIG. 81 a cutting guide 2450 may be applied to the tibia or other bones. In addition, the cutting guide shown in FIGS. 81 and 82 is intentional depicted as only being capable of completing the anterior portion of the tibial resection; this is intended to demonstrate that, when planar cuts are desired, the milled surface can be used to guide the remaining resection of an oscillating sawblade thus preserving the accuracy of the milling technique while minimizing the precision errors of the oscillating sawblade.

The complete disclosures of the patents, patent applications, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. A method of performing primary total knee arthroplasty surgery on a diseased knee joint of a human patient, comprising:
    placing a femoral alignment guide on a femur so that the femoral alignment guide simultaneously contacts at least five points on the femur including one point on a non-resected anterior cortex of the femur and four points on non-resected articular surfaces of the femur, including two points on a non-resected lateral femoral condyle and two points on a non-resected medial femoral condyle;
    creating at least four holes in the femur by passing one or more elongate fixation elements through the femoral alignment guide and into the femur prior to creating a planar resected surface on the femur, the femoral alignment guide including at least four cannulae through which the holes in the femur are created;
    removing the femoral alignment guide and then guiding an oscillating sawblade using a distal femoral cutting block to make a planar distal resected surface on the femur and subsequently guiding the oscillating sawblade using a second femoral cutting block placed in contact with the planar distal resected surface to make planar anterior chamfer and posterior chamfer resected surfaces on the femur, wherein the distal femoral cutting block and the second femoral cutting block mechanically reference a plurality of the holes created in the femur after removing the femoral alignment guide;
    placing a tibial alignment guide on a proximal end of a tibia so that the tibial alignment guide simultaneously contacts at least five points on the tibia including one point on a non-resected anterior cortex of the tibia and four points on non-resected articular surfaces of the tibia, including two points on a non-resected lateral tibial condyle and two points on a non-resected medial tibial condyle;
    creating a plurality of holes in the tibia by passing one or more elongate fixation elements through the tibial alignment guide and into the tibia prior to creating a planar resected surface on the tibia, the tibial alignment guide including a plurality of apertures through which the holes in the tibia are created;
    removing the tibial alignment guide and then guiding an oscillating sawblade using a proximal tibial cutting block to make a planar proximal resected surface on the tibia, wherein the tibial cutting block mechanically references the holes created in the tibia to position the tibial cutting block substantially along a medial half of the anterior cortex of the tibia after removing the tibial alignment guide and such that a lateral most end of the proximal tibial cutting block used to make the proximal resected surface on the tibia is located medially of a lateral most point of contact between the tibial alignment guide and the non-resected articular surfaces of the tibia, and the proximal tibial cutting block is not mechanically interconnected to any other cutting blocks while it guides the oscillating sawblade; and
    implanting a femoral total knee arthroplasty implant with fixation surfaces configured to face the planar distal resected surface and the planar anterior chamfer and posterior chamfer resected surfaces on the femur and implanting a tibial total knee arthroplasty implant with a fixation surface configured to face the planar proximal resected surface on the tibia, wherein neither the femoral alignment guide nor the tibial alignment guide is mechanically interconnected to an intramedullary rod or a tibial referencing tensor linkage while the holes are created in the femur and the tibia using the femoral alignment guide and the tibial alignment guide.

2. The method of claim 1, wherein the distal femoral cutting block is positioned such that a lateral most end of the distal femoral cutting block used to make the distal resected surface on the femur is located medially of a lateral most point of contact between the femoral alignment guide and the non-resected articular surfaces of the femur.

3. The method of claim 1, wherein neither the femoral alignment guide nor the tibial alignment guide have a slot used to guide an oscillating saw blade during the total knee arthroplasty procedure.

4. The method of claim 1, wherein the elongate fixation elements are selected from the group consisting of: screws, cannulated screws, drills, nails and pins.

5. The method of claim 1, wherein creating holes in the femur creates the holes in the femoral cortex.

6. The method of claim 1, wherein creating holes in the tibia creates the holes in the tibial cortex.

7. The method of claim 1, wherein a location and orientation of the holes in the tibia are mechanically referenced to determine a location and orientation of the tibial total knee arthroplasty implant in a plurality of degrees of freedom including anterior-posterior location, medial-lateral location and internal-external rotational orientation.

8. The method of claim 1, wherein the step of guiding the oscillating sawblade using a second femoral cutting block further includes creating an anterior resected surface and a posterior resected surface on the femur using the second femoral cutting block.

9. The method of claim 1, wherein creating holes in the femur creates two pairs of holes in the femur.

10. The method of claim 1, wherein creating holes in the tibia creates two pairs of holes in the tibia.

11. The method of claim 1, wherein at least two of the at least four cannulae in the femoral alignment guide include pin guides positioned therein and wherein creating at least two of the holes in the femur includes passing one or more of the elongate fixation elements through the pin guides.

12. The method of claim 11, wherein the pin guides are at least one of fixed within the cannulae or configured to be extended through the cannulae.

13. The method of claim 1, wherein the cannulae in the tibial alignment guide include pin guides positioned therein and wherein creating holes in the tibia includes passing one or more of the elongate fixation elements through the pin guides.

14. The method of claim 13, wherein the pin guides are at least one of fixed within the cannulae or configured to be extended through the cannulae.

15. A method of performing primary total knee arthroplasty surgery on a diseased knee joint of a human patient, comprising:
    placing a femoral alignment guide on a femur so that the femoral alignment guide simultaneously contacts at least five points on the femur including one point on a non-resected anterior cortex of the femur and four points on non-resected articular surfaces of the femur, including two points on a non-resected lateral femoral condyle and two points on a non-resected medial femoral condyle;

creating at least four holes in the femur by passing one or more elongate fixation elements through the femoral alignment guide and into the femur prior to creating a planar resected surface on the femur, the femoral alignment guide including at least four cannulae through which the holes in the femur are created, wherein at least two of the at least four cannulae in the femoral alignment guide include pin guides positioned therein and wherein creating at least two of the holes in the femur includes passing one or more of the elongate fixation elements through the pin guides;

removing the femoral alignment guide and then guiding an oscillating sawblade using a distal femoral cutting block to make a planar distal resected surface on the femur and subsequently guiding the oscillating sawblade using a second femoral cutting block placed in contact with the planar distal resected surface to make planar anterior chamfer and posterior chamfer resected surfaces on the femur, wherein the distal femoral cutting block and the second femoral cutting block mechanically reference a plurality of the holes created in the femur after removing the femoral alignment guide;

placing a tibial alignment guide on a proximal end of a tibia so that the tibial alignment guide simultaneously contacts at least five points on the tibia including one point on a non-resected anterior cortex of the tibia and four points on non-resected articular surfaces of the tibia, including two points on a non-resected lateral tibial condyle and two points on a non-resected medial tibial condyle;

creating a plurality of holes in the tibia by passing one or more elongate fixation elements through the tibial alignment guide and into the tibia prior to creating a planar resected surface on the tibia, the tibial alignment guide including a plurality of apertures through which the holes in the tibia are created, wherein the cannulae in the tibial alignment guide include pin guides positioned therein and wherein creating holes in the tibia includes passing one or more of the elongate fixation elements through the pin guides;

removing the tibial alignment guide and then guiding an oscillating sawblade using a proximal tibial cutting block to make a planar proximal resected surface on the tibia, wherein the tibial cutting block mechanically references the holes created in the tibia to position the tibial cutting block substantially along a medial half of the anterior cortex of the tibia after removing the tibial alignment guide and such that a lateral most end of the proximal tibial cutting block used to make the proximal resected surface on the tibia is located medially of a lateral most point of contact between the tibial alignment guide and the non-resected articular surfaces of the tibia, and the proximal tibial cutting block is not mechanically interconnected to any other cutting blocks while it guides the oscillating sawblade; and implanting a femoral total knee arthroplasty implant with fixation surfaces configured to face the planar distal resected surface and the planar anterior chamfer and posterior chamfer resected surfaces on the femur and implanting a tibial total knee arthroplasty implant with a fixation surface configured to face the planar proximal resected surface on the tibia, wherein neither the femoral alignment guide nor the tibial alignment guide is mechanically interconnected to an intramedullary rod or a tibial referencing tensor linkage while the holes are created in the femur and the tibia using the femoral alignment guide and the tibial alignment guide.

16. The method of claim 15, wherein the distal femoral cutting block is positioned such that a lateral most end of the distal femoral cutting block used to make the distal resected surface on the femur is located medially of a lateral most point of contact between the femoral alignment guide and the non-resected articular surfaces of the femur.

17. The method of claim 15, wherein neither the femoral alignment guide nor the tibial alignment guide have a slot used to guide an oscillating saw blade during the total knee arthroplasty procedure.

18. The method of claim 15, wherein the elongate fixation elements are selected from the group consisting of: screws, cannulated screws, drills, nails and pins.

19. The method of claim 15, wherein creating holes in the femur creates the holes in the femoral cortex.

20. The method of claim 15, wherein creating holes in the tibia creates the holes in the tibial cortex.

21. The method of claim 15, wherein a location and orientation of the holes in the tibia are mechanically referenced to determine a location and orientation of the tibial total knee arthroplasty implant in a plurality of degrees of freedom including anterior-posterior location, medial-lateral location and internal-external rotational orientation.

22. The method of claim 15, wherein the step of guiding the oscillating sawblade using a second femoral cutting block further includes creating an anterior resected surface and a posterior resected surface on the femur using the second femoral cutting block.

23. The method of claim 15, wherein creating holes in the femur creates two pairs of holes in the femur.

24. The method of claim 15, wherein creating holes in the tibia creates two pairs of holes in the tibia.

25. The method of claim 15, wherein the pin guides are at least one of fixed within the cannulae or configured to be extended through the cannulae.

* * * * *